US011539243B2

(12) United States Patent
Katajamaki et al.

(10) Patent No.: US 11,539,243 B2
(45) Date of Patent: Dec. 27, 2022

(54) SYSTEMS AND METHODS FOR MINIATURIZED ANTENNA FOR WIRELESS POWER TRANSMISSIONS

(71) Applicant: Energous Corporation, San Jose, CA (US)

(72) Inventors: Tuomo Katajamaki, San Jose, CA (US); Yunhong Liu, San Jose, CA (US)

(73) Assignee: Energous Corporation, San Jose, CA (US)

( * ) Notice: Subject to any disclaimer, the term of this patent is extended or adjusted under 35 U.S.C. 154(b) by 423 days.

(21) Appl. No.: 16/775,214

(22) Filed: Jan. 28, 2020

(65) Prior Publication Data
US 2020/0244104 A1 Jul. 30, 2020

Related U.S. Application Data

(60) Provisional application No. 62/797,808, filed on Jan. 28, 2019.

(51) Int. Cl.
*H01Q 1/27* (2006.01)
*H02J 50/10* (2016.01)
(Continued)

(52) U.S. Cl.
CPC .............. *H02J 50/10* (2016.02); *A61P 35/00* (2018.01); *C07K 16/2809* (2013.01);
(Continued)

(58) Field of Classification Search
CPC .. H02J 50/10; H02J 7/02; H02J 50/20; H01Q 1/2291; H01Q 9/0407; H01Q 9/285;
(Continued)

(56) References Cited

U.S. PATENT DOCUMENTS

| 787,412 A | 4/1905 | Tesla |
| 2,811,624 A | 10/1957 | Haagensen |

(Continued)

FOREIGN PATENT DOCUMENTS

| CN | 201278367 Y | 7/2009 |
| CN | 102292896 A | 12/2011 |

(Continued)

OTHER PUBLICATIONS

Hill, "Hearing Aid Sizes", Hearingdirect.com, Mar. 2014, entire document (Year: 2014).*

(Continued)

*Primary Examiner* — David E Lotter
(74) *Attorney, Agent, or Firm* — Morgan, Lewis & Bockius LLP

(57) ABSTRACT

A wireless power receiving system includes two or more electrically small antenna arms and a common antenna ground. The two or more electrically small antenna arms are connected to the same common antenna ground and are close enough to one another to be strongly coupled. In some embodiments, the two or more electrically small antenna arms are tuned to the same functional frequency so that they load one another to create self-resonance. The wireless power receiving system receives the transmitted wireless power wave emitting from a wireless power transmitter without added lossy matching components.

13 Claims, 12 Drawing Sheets

(51) Int. Cl.

| | | |
|---|---|---|
| *H01Q 1/22* | (2006.01) | |
| *H01Q 9/04* | (2006.01) | |
| *H01Q 9/28* | (2006.01) | |
| *H01Q 9/40* | (2006.01) | |
| *H01Q 13/10* | (2006.01) | |
| *H04B 5/00* | (2006.01) | |
| *H04R 25/00* | (2006.01) | |
| *A61P 35/00* | (2006.01) | |
| *C07K 16/28* | (2006.01) | |
| *A61K 39/00* | (2006.01) | |

(52) U.S. Cl.
CPC ...... *C07K 16/2827* (2013.01); *C07K 16/2887* (2013.01); *C07K 16/2896* (2013.01); *H01Q 1/2291* (2013.01); *H01Q 9/0407* (2013.01); *H01Q 9/285* (2013.01); *H01Q 9/40* (2013.01); *H01Q 13/106* (2013.01); *H04B 5/0037* (2013.01); *H04R 25/00* (2013.01); *A61K 2039/505* (2013.01); *C07K 2317/24* (2013.01); *C07K 2317/31* (2013.01); *C07K 2317/56* (2013.01); *C07K 2317/73* (2013.01); *C07K 2317/732* (2013.01); *C07K 2317/734* (2013.01); *C07K 2317/77* (2013.01); *C07K 2317/92* (2013.01); *H04R 2225/31* (2013.01)

(58) Field of Classification Search
CPC ...... H01Q 9/40; H01Q 13/106; H04B 5/0037; H04R 25/00; H04R 2225/31; H04R 2225/51
See application file for complete search history.

(56) References Cited

U.S. PATENT DOCUMENTS

| | | |
|---|---|---|
| 2,863,148 A | 12/1958 | Gammon et al. |
| 3,167,775 A | 1/1965 | Guertler |
| 3,434,678 A | 3/1969 | Brown et al. |
| 3,696,384 A | 10/1972 | Lester |
| 3,754,269 A | 8/1973 | Gavin |
| 4,101,895 A | 7/1978 | Jones, Jr. |
| 4,360,741 A | 11/1982 | Fitzsimmons et al. |
| 4,944,036 A | 7/1990 | Hyatt |
| 4,995,010 A | 2/1991 | Knight |
| 5,142,292 A | 8/1992 | Chang |
| 5,200,759 A | 4/1993 | McGinnis |
| 5,211,471 A | 5/1993 | Rohrs |
| 5,276,455 A | 1/1994 | Fitzsimmons et al. |
| 5,548,292 A | 8/1996 | Hirshfield et al. |
| 5,556,749 A | 9/1996 | Mitsuhashi et al. |
| 5,568,088 A | 10/1996 | Dent et al. |
| 5,631,572 A | 5/1997 | Sheen et al. |
| 5,646,633 A | 7/1997 | Dahlberg |
| 5,697,063 A | 12/1997 | Kishigami et al. |
| 5,712,642 A | 1/1998 | Hulderman |
| 5,936,527 A | 8/1999 | Isaacman et al. |
| 5,982,139 A | 11/1999 | Parise |
| 6,046,708 A | 4/2000 | MacDonald, Jr. et al. |
| 6,061,025 A | 5/2000 | Jackson et al. |
| 6,127,799 A | 10/2000 | Krishnan |
| 6,127,942 A | 10/2000 | Welle |
| 6,163,296 A | 12/2000 | Lier et al. |
| 6,176,433 B1 | 1/2001 | Uesaka et al. |
| 6,271,799 B1 | 8/2001 | Rief |
| 6,289,237 B1 | 9/2001 | Mickle et al. |
| 6,329,908 B1 | 12/2001 | Frecska |
| 6,400,586 B2 | 6/2002 | Raddi et al. |
| 6,421,235 B2 | 7/2002 | Ditzik |
| 6,437,685 B2 | 8/2002 | Hanaki |
| 6,456,253 B1 | 9/2002 | Rummeli et al. |
| 6,476,795 B1 | 11/2002 | Derocher et al. |
| 6,501,414 B2 | 12/2002 | Amdt et al. |
| 6,583,723 B2 | 6/2003 | Watanabe et al. |
| 6,597,897 B2 | 7/2003 | Tang |
| 6,615,074 B2 | 9/2003 | Mickle et al. |
| 6,650,376 B1 | 11/2003 | Obitsu |
| 6,664,920 B1 | 12/2003 | Mott et al. |
| 6,680,700 B2 | 1/2004 | Hilgers |
| 6,798,716 B1 | 9/2004 | Charych |
| 6,803,744 B1 | 10/2004 | Sabo |
| 6,853,197 B1 | 2/2005 | McFarland |
| 6,856,291 B2 | 2/2005 | Mickle et al. |
| 6,911,945 B2 | 6/2005 | Korva |
| 6,960,968 B2 | 11/2005 | Odendaal et al. |
| 6,967,462 B1 | 11/2005 | Landis |
| 6,988,026 B2 | 1/2006 | Breed et al. |
| 7,003,350 B2 | 2/2006 | Denker et al. |
| 7,012,572 B1 | 3/2006 | Schaffner et al. |
| 7,027,311 B2 | 4/2006 | Vanderelli et al. |
| 7,068,234 B2 | 6/2006 | Sievenpiper |
| 7,068,991 B2 | 6/2006 | Parise |
| 7,079,079 B2 | 7/2006 | Jo et al. |
| 7,183,748 B1 | 2/2007 | Unno et al. |
| 7,191,013 B1 | 3/2007 | Miranda et al. |
| 7,193,644 B2 | 3/2007 | Carter |
| 7,196,663 B2 | 3/2007 | Bolzer et al. |
| 7,205,749 B2 | 4/2007 | Hagen et al. |
| 7,215,296 B2 | 5/2007 | Abramov et al. |
| 7,222,356 B1 | 5/2007 | Yonezawa et al. |
| 7,274,334 B2 | 9/2007 | O'Riordan et al. |
| 7,274,336 B2 | 9/2007 | Carson |
| 7,351,975 B2 | 4/2008 | Brady et al. |
| 7,359,730 B2 | 4/2008 | Dennis et al. |
| 7,372,408 B2 | 5/2008 | Gaucher |
| 7,392,068 B2 | 6/2008 | Dayan |
| 7,403,803 B2 | 7/2008 | Mickle et al. |
| 7,443,057 B2 | 10/2008 | Nunally |
| 7,451,839 B2 | 11/2008 | Perlman |
| 7,463,201 B2 | 12/2008 | Chiang et al. |
| 7,471,247 B2 | 12/2008 | Saily |
| 7,535,195 B1 | 5/2009 | Horovitz et al. |
| 7,614,556 B2 | 11/2009 | Overhultz et al. |
| 7,639,994 B2 | 12/2009 | Greene et al. |
| 7,643,312 B2 | 1/2010 | Vanderelli et al. |
| 7,652,577 B1 | 1/2010 | Madhow et al. |
| 7,679,576 B2 | 3/2010 | Riedel et al. |
| 7,702,771 B2 | 4/2010 | Ewing et al. |
| 7,786,419 B2 | 8/2010 | Hyde et al. |
| 7,812,771 B2 | 10/2010 | Greene et al. |
| 7,830,312 B2 | 11/2010 | Choudhury et al. |
| 7,844,306 B2 | 11/2010 | Shearer et al. |
| 7,868,482 B2 | 1/2011 | Greene et al. |
| 7,898,105 B2 | 3/2011 | Greene et al. |
| 7,904,117 B2 | 3/2011 | Doan et al. |
| 7,911,386 B1 | 3/2011 | Ito et al. |
| 7,925,308 B2 | 4/2011 | Greene et al. |
| 7,948,208 B2 | 5/2011 | Partovi et al. |
| 8,049,676 B2 | 11/2011 | Yoon et al. |
| 8,055,003 B2 | 11/2011 | Mittleman et al. |
| 8,070,595 B2 | 12/2011 | Alderucci et al. |
| 8,072,380 B2 | 12/2011 | Crouch |
| 8,092,301 B2 | 1/2012 | Alderucci et al. |
| 8,099,140 B2 | 1/2012 | Arai |
| 8,115,448 B2 | 2/2012 | John |
| 8,159,090 B2 | 4/2012 | Greene et al. |
| 8,159,364 B2 | 4/2012 | Zeine |
| 8,180,286 B2 | 5/2012 | Yamasuge |
| 8,184,454 B2 | 5/2012 | Mao |
| 8,228,194 B2 | 7/2012 | Mickle |
| 8,234,509 B2 | 7/2012 | Gioscia et al. |
| 8,264,101 B2 | 9/2012 | Hyde et al. |
| 8,264,291 B2 | 9/2012 | Morita |
| 8,276,325 B2 | 10/2012 | Clifton et al. |
| 8,278,784 B2 | 10/2012 | Cook et al. |
| 8,284,101 B2 | 10/2012 | Fusco |
| 8,310,201 B1 | 11/2012 | Wright |
| 8,338,991 B2 | 12/2012 | Von Novak et al. |
| 8,362,745 B2 | 1/2013 | Tinaphong |
| 8,380,255 B2 | 2/2013 | Shearer et al. |
| 8,384,600 B2 | 2/2013 | Huang et al. |
| 8,410,953 B2 | 4/2013 | Zeine |
| 8,411,963 B2 | 4/2013 | Luff |

(56) References Cited

U.S. PATENT DOCUMENTS

| | | |
|---|---|---|
| 8,432,062 B2 | 4/2013 | Greene et al. |
| 8,432,071 B2 | 4/2013 | Huang et al. |
| 8,446,248 B2 | 5/2013 | Zeine |
| 8,447,234 B2 | 5/2013 | Cook et al. |
| 8,451,189 B1 | 5/2013 | Fluhler |
| 8,452,235 B2 | 5/2013 | Kirby et al. |
| 8,457,656 B2 | 6/2013 | Perkins et al. |
| 8,461,817 B2 | 6/2013 | Martin et al. |
| 8,467,733 B2 | 6/2013 | Leabman |
| 8,497,601 B2 | 7/2013 | Hall et al. |
| 8,497,658 B2 | 7/2013 | Von Novak et al. |
| 8,552,597 B2 | 8/2013 | Song et al. |
| 8,558,661 B2 | 10/2013 | Zeine |
| 8,560,026 B2 | 10/2013 | Chanterac |
| 8,564,485 B2 | 10/2013 | Milosavljevic et al. |
| 8,604,746 B2 | 12/2013 | Lee |
| 8,614,643 B2 | 12/2013 | Leabman |
| 8,621,245 B2 | 12/2013 | Shearer et al. |
| 8,626,249 B2 | 1/2014 | Kuusilinna et al. |
| 8,629,576 B2 | 1/2014 | Levine |
| 8,653,966 B2 | 2/2014 | Rao et al. |
| 8,674,551 B2 | 3/2014 | Low et al. |
| 8,686,685 B2 | 4/2014 | Moshfeghi |
| 8,686,905 B2 | 4/2014 | Shtrom |
| 8,712,355 B2 | 4/2014 | Black et al. |
| 8,712,485 B2 | 4/2014 | Tam |
| 8,718,773 B2 | 5/2014 | Wills et al. |
| 8,729,737 B2 | 5/2014 | Schatz et al. |
| 8,736,228 B1 | 5/2014 | Freed et al. |
| 8,760,113 B2 | 6/2014 | Keating |
| 8,770,482 B2 | 7/2014 | Ackermann et al. |
| 8,772,960 B2 | 7/2014 | Yoshida |
| 8,823,319 B2 | 9/2014 | Von Novak, III et al. |
| 8,832,646 B1 | 9/2014 | Wendling |
| 8,854,176 B2 | 10/2014 | Zeine |
| 8,860,364 B2 | 10/2014 | Low et al. |
| 8,897,770 B1 | 11/2014 | Frolov et al. |
| 8,903,456 B2 | 12/2014 | Chu et al. |
| 8,917,057 B2 | 12/2014 | Hui |
| 8,923,189 B2 | 12/2014 | Leabman |
| 8,928,544 B2 | 1/2015 | Massie et al. |
| 8,937,408 B2 | 1/2015 | Ganem et al. |
| 8,946,940 B2 | 2/2015 | Kim et al. |
| 8,963,486 B2 | 2/2015 | Kirby et al. |
| 8,970,070 B2 | 3/2015 | Sada et al. |
| 8,989,053 B1 | 3/2015 | Skaaksrud et al. |
| 9,000,616 B2 | 4/2015 | Greene et al. |
| 9,001,622 B2 | 4/2015 | Perry |
| 9,006,934 B2 | 4/2015 | Kozakai et al. |
| 9,021,277 B2 | 4/2015 | Shearer et al. |
| 9,030,161 B2 | 5/2015 | Lu et al. |
| 9,059,598 B2 | 6/2015 | Kang et al. |
| 9,059,599 B2 | 6/2015 | Won et al. |
| 9,077,188 B2 | 7/2015 | Moshfeghi |
| 9,083,595 B2 | 7/2015 | Rakib et al. |
| 9,088,216 B2 | 7/2015 | Garrity et al. |
| 9,124,125 B2 | 9/2015 | Leabman et al. |
| 9,130,397 B2 | 9/2015 | Leabman et al. |
| 9,130,602 B2 | 9/2015 | Cook |
| 9,142,998 B2 | 9/2015 | Yu et al. |
| 9,143,000 B2 | 9/2015 | Leabman et al. |
| 9,143,010 B2 | 9/2015 | Urano |
| 9,153,074 B2 | 10/2015 | Zhou et al. |
| 9,178,389 B2 | 11/2015 | Hwang |
| 9,225,196 B2 | 12/2015 | Huang et al. |
| 9,240,469 B2 | 1/2016 | Sun et al. |
| 9,242,411 B2 | 1/2016 | Kritchman et al. |
| 9,244,500 B2 | 1/2016 | Cain et al. |
| 9,252,628 B2 | 2/2016 | Leabman et al. |
| 9,270,344 B2 | 2/2016 | Rosenberg |
| 9,276,329 B2 | 3/2016 | Jones et al. |
| 9,282,582 B1 | 3/2016 | Dunsbergen et al. |
| 9,294,840 B1 | 3/2016 | Anderson et al. |
| 9,297,896 B1 | 3/2016 | Andrews |
| 9,318,898 B2 | 4/2016 | John |
| 9,368,020 B1 | 6/2016 | Bell et al. |
| 9,401,977 B1 | 7/2016 | Gaw |
| 9,409,490 B2 | 8/2016 | Kawashima |
| 9,419,335 B2 | 8/2016 | Pintos |
| 9,438,045 B1 | 9/2016 | Leabman |
| 9,438,046 B1 | 9/2016 | Leabman |
| 9,444,283 B2 | 9/2016 | Son et al. |
| 9,450,449 B1 | 9/2016 | Leabman et al. |
| 9,461,502 B2 | 10/2016 | Lee et al. |
| 9,520,725 B2 | 12/2016 | Masaoka et al. |
| 9,520,748 B2 | 12/2016 | Hyde et al. |
| 9,522,270 B2 | 12/2016 | Perryman et al. |
| 9,532,748 B2 | 1/2017 | Denison et al. |
| 9,537,354 B2 | 1/2017 | Bell et al. |
| 9,537,357 B2 | 1/2017 | Leabman |
| 9,537,358 B2 | 1/2017 | Leabman |
| 9,538,382 B2 | 1/2017 | Bell et al. |
| 9,544,640 B2 | 1/2017 | Lau |
| 9,559,553 B2 | 1/2017 | Bae |
| 9,564,773 B2 | 2/2017 | Pogorelik et al. |
| 9,571,974 B2 | 2/2017 | Choi et al. |
| 9,590,317 B2 | 3/2017 | Zimmerman et al. |
| 9,590,444 B2 | 3/2017 | Walley |
| 9,620,996 B2 | 4/2017 | Zeine |
| 9,647,328 B2 | 5/2017 | Dobric |
| 9,706,137 B2 | 7/2017 | Scanlon et al. |
| 9,711,999 B2 | 7/2017 | Hietala et al. |
| 9,723,635 B2 | 8/2017 | Nambord et al. |
| 9,793,758 B2 | 10/2017 | Leabman |
| 9,793,764 B2 | 10/2017 | Perry |
| 9,800,172 B1 | 10/2017 | Leabman |
| 9,806,564 B2 | 10/2017 | Leabman |
| 9,819,230 B2 | 11/2017 | Petras et al. |
| 9,825,674 B1 | 11/2017 | Leabman |
| 9,843,229 B2 | 12/2017 | Leabman |
| 9,847,669 B2 | 12/2017 | Leabman |
| 9,847,677 B1 | 12/2017 | Leabman |
| 9,853,361 B2 | 12/2017 | Chen et al. |
| 9,853,692 B1 | 12/2017 | Bell et al. |
| 9,859,758 B1 | 1/2018 | Leabman |
| 9,866,279 B2 | 1/2018 | Bell et al. |
| 9,867,032 B2 | 1/2018 | Verma et al. |
| 9,871,301 B2 | 1/2018 | Contopanagos |
| 9,876,380 B1 | 1/2018 | Leabman et al. |
| 9,876,394 B1 | 1/2018 | Leabman |
| 9,876,536 B1 | 1/2018 | Bell et al. |
| 9,882,394 B1 | 1/2018 | Bell et al. |
| 9,887,584 B1 | 2/2018 | Bell et al. |
| 9,893,555 B1 | 2/2018 | Leabman et al. |
| 9,893,564 B2 | 2/2018 | de Rochemont |
| 9,899,744 B1 | 2/2018 | Contopanagos et al. |
| 9,899,844 B1 | 2/2018 | Bell et al. |
| 9,899,861 B1 | 2/2018 | Leabman et al. |
| 9,916,485 B1 | 3/2018 | Lilly et al. |
| 9,917,477 B1 | 3/2018 | Bell et al. |
| 9,923,386 B1 | 3/2018 | Leabman et al. |
| 9,939,864 B1 | 4/2018 | Bell et al. |
| 9,965,009 B1 | 5/2018 | Bell et al. |
| 9,966,765 B1 | 5/2018 | Leabman |
| 9,966,784 B2 | 5/2018 | Leabman |
| 9,967,743 B1 | 5/2018 | Bell et al. |
| 9,973,008 B1 | 5/2018 | Leabman |
| 10,003,211 B1 | 6/2018 | Leabman et al. |
| 10,008,777 B1 | 6/2018 | Broyde et al. |
| 10,014,728 B1 | 7/2018 | Leabman |
| 10,027,159 B2 | 7/2018 | Hosseini |
| 10,038,337 B1 | 7/2018 | Leabman et al. |
| 10,050,462 B1 | 8/2018 | Leabman et al. |
| 10,056,782 B1 | 8/2018 | Leabman |
| 10,063,064 B1 | 8/2018 | Bell et al. |
| 10,068,703 B1 | 9/2018 | Contopanagos |
| 10,075,008 B1 | 9/2018 | Bell et al. |
| 10,090,699 B1 | 10/2018 | Leabman |
| 10,090,886 B1 | 10/2018 | Bell et al. |
| 10,103,552 B1 | 10/2018 | Leabman et al. |
| 10,110,046 B1 | 10/2018 | Esquibel et al. |
| 10,122,219 B1 | 11/2018 | Hosseini et al. |
| 10,124,754 B1 | 11/2018 | Leabman |
| 10,128,686 B1 | 11/2018 | Leabman et al. |

(56) References Cited

U.S. PATENT DOCUMENTS

| | | |
|---|---|---|
| 10,134,260 B1 | 11/2018 | Bell et al. |
| 10,135,112 B1 | 11/2018 | Hosseini |
| 10,135,294 B1 | 11/2018 | Leabman |
| 10,141,771 B1 | 11/2018 | Hosseini et al. |
| 10,148,097 B1 | 12/2018 | Leabman et al. |
| 10,153,645 B1 | 12/2018 | Bell et al. |
| 10,153,653 B1 | 12/2018 | Bell et al. |
| 10,153,660 B1 | 12/2018 | Leabman et al. |
| 10,158,257 B2 | 12/2018 | Leabman |
| 10,158,259 B1 | 12/2018 | Leabman |
| 10,164,478 B2 | 12/2018 | Leabman |
| 10,170,917 B1 | 1/2019 | Bell et al. |
| 10,181,756 B2 | 1/2019 | Bae et al. |
| 10,186,892 B2 | 1/2019 | Hosseini et al. |
| 10,193,396 B1 | 1/2019 | Bell et al. |
| 10,199,835 B2 | 2/2019 | Bell |
| 10,199,849 B1 | 2/2019 | Bell |
| 10,205,239 B1 | 2/2019 | Contopanagos et al. |
| 10,211,674 B1 | 2/2019 | Leabman et al. |
| 10,223,717 B1 | 3/2019 | Bell |
| 10,224,758 B2 | 3/2019 | Leabman et al. |
| 10,224,982 B1 | 3/2019 | Leabman |
| 10,230,266 B1 | 3/2019 | Leabman et al. |
| 10,243,414 B1 | 3/2019 | Leabman et al. |
| 10,256,657 B2 | 4/2019 | Hosseini et al. |
| 10,256,677 B2 | 4/2019 | Hosseini et al. |
| 10,263,432 B1 | 4/2019 | Leabman et al. |
| 10,263,476 B2 | 4/2019 | Leabman |
| 10,270,261 B2 | 4/2019 | Bell et al. |
| 10,277,054 B2 | 4/2019 | Hosseini |
| 10,291,055 B1 | 5/2019 | Bell et al. |
| 10,291,056 B2 | 5/2019 | Bell et al. |
| 10,291,066 B1 | 5/2019 | Leabman |
| 10,291,294 B2 | 5/2019 | Leabman |
| 10,298,024 B2 | 5/2019 | Leabman |
| 10,298,133 B2 | 5/2019 | Leabman |
| 10,305,315 B2 | 5/2019 | Leabman et al. |
| 10,312,715 B2 | 6/2019 | Leabman |
| 10,320,446 B2 | 6/2019 | Hosseini |
| 10,333,332 B1 | 6/2019 | Hosseini |
| 10,355,534 B2 | 7/2019 | Johnston et al. |
| 10,389,161 B2 | 8/2019 | Hosseini et al. |
| 10,396,588 B2 | 8/2019 | Leabman |
| 10,396,604 B2 | 8/2019 | Bell et al. |
| 10,439,442 B2 | 10/2019 | Hosseini et al. |
| 10,439,448 B2 | 10/2019 | Bell et al. |
| 10,447,093 B2 | 10/2019 | Hosseini |
| 10,476,312 B2 | 11/2019 | Johnston et al. |
| 10,483,768 B2 | 11/2019 | Bell et al. |
| 10,490,346 B2 | 11/2019 | Contopanagos |
| 10,491,029 B2 | 11/2019 | Hosseini |
| 10,498,144 B2 | 12/2019 | Leabman et al. |
| 10,511,097 B2 | 12/2019 | Kornaros et al. |
| 10,511,196 B2 | 12/2019 | Hosseini |
| 10,516,289 B2 | 12/2019 | Leabman et al. |
| 10,516,301 B2 | 12/2019 | Leabman |
| 10,523,033 B2 | 12/2019 | Leabman |
| 10,523,058 B2 | 12/2019 | Leabman |
| 10,554,052 B2 | 2/2020 | Bell et al. |
| 10,594,165 B2 | 3/2020 | Hosseini |
| 10,615,647 B2 | 4/2020 | Johnston et al. |
| 10,667,061 B2 * | 5/2020 | Ozden ................. H04R 25/505 |
| 10,680,319 B2 | 6/2020 | Hosseini et al. |
| 2001/0027876 A1 | 10/2001 | Tsukamoto et al. |
| 2002/0001307 A1 | 1/2002 | Nguyen et al. |
| 2002/0024471 A1 | 2/2002 | Ishitobi |
| 2002/0028655 A1 | 3/2002 | Rosener et al. |
| 2002/0034958 A1 | 3/2002 | Oberschmidt et al. |
| 2002/0054330 A1 | 5/2002 | Jinbo et al. |
| 2002/0065052 A1 | 5/2002 | Pande et al. |
| 2002/0072784 A1 | 6/2002 | Sheppard et al. |
| 2002/0095980 A1 | 7/2002 | Breed et al. |
| 2002/0103447 A1 | 8/2002 | Terry |
| 2002/0123776 A1 | 9/2002 | Von Arx |
| 2002/0133592 A1 | 9/2002 | Matsuda |
| 2002/0171594 A1 | 11/2002 | Fang |
| 2002/0172223 A1 | 11/2002 | Stilp |
| 2003/0005759 A1 | 1/2003 | Breed et al. |
| 2003/0038750 A1 | 2/2003 | Chen |
| 2003/0058187 A1 | 3/2003 | Billiet et al. |
| 2003/0076274 A1 | 4/2003 | Phelan et al. |
| 2003/0179152 A1 | 9/2003 | Watada et al. |
| 2003/0179573 A1 | 9/2003 | Chun |
| 2003/0192053 A1 | 10/2003 | Sheppard et al. |
| 2004/0019624 A1 | 1/2004 | Sukegawa |
| 2004/0020100 A1 | 2/2004 | O'Brian et al. |
| 2004/0036657 A1 | 2/2004 | Forster et al. |
| 2004/0066251 A1 | 4/2004 | Eleftheriades et al. |
| 2004/0107641 A1 | 6/2004 | Walton et al. |
| 2004/0113543 A1 | 6/2004 | Daniels |
| 2004/0119675 A1 | 6/2004 | Washio et al. |
| 2004/0130425 A1 | 7/2004 | Dayan et al. |
| 2004/0130442 A1 | 7/2004 | Breed |
| 2004/0142733 A1 | 7/2004 | Parise |
| 2004/0145342 A1 | 7/2004 | Lyon |
| 2004/0155832 A1 | 8/2004 | Yuanzhu |
| 2004/0196190 A1 | 10/2004 | Mendolia et al. |
| 2004/0203979 A1 | 10/2004 | Attar et al. |
| 2004/0207559 A1 | 10/2004 | Milosavljevic |
| 2004/0218759 A1 | 11/2004 | Yacobi |
| 2004/0241402 A1 | 12/2004 | Kawate |
| 2004/0259604 A1 | 12/2004 | Mickle et al. |
| 2004/0263124 A1 | 12/2004 | Wieck et al. |
| 2005/0007276 A1 | 1/2005 | Barrick et al. |
| 2005/0030118 A1 | 2/2005 | Wang |
| 2005/0046584 A1 | 3/2005 | Breed |
| 2005/0055316 A1 | 3/2005 | Williams |
| 2005/0077872 A1 | 4/2005 | Single |
| 2005/0093766 A1 | 5/2005 | Turner |
| 2005/0116683 A1 | 6/2005 | Cheng |
| 2005/0117660 A1 | 6/2005 | Vialle et al. |
| 2005/0134517 A1 | 6/2005 | Gottl |
| 2005/0171411 A1 | 8/2005 | KenKnight |
| 2005/0198673 A1 | 9/2005 | Kit et al. |
| 2005/0227619 A1 | 10/2005 | Lee et al. |
| 2005/0232469 A1 | 10/2005 | Schofield |
| 2005/0237249 A1 | 10/2005 | Nagel |
| 2005/0237258 A1 | 10/2005 | Abramov et al. |
| 2005/0282591 A1 | 12/2005 | Shaff |
| 2006/0013335 A1 | 1/2006 | Leabman |
| 2006/0019712 A1 | 1/2006 | Choi |
| 2006/0030279 A1 | 2/2006 | Leabman et al. |
| 2006/0033674 A1 | 2/2006 | Essig, Jr. et al. |
| 2006/0056855 A1 | 3/2006 | Nakagawa et al. |
| 2006/0071308 A1 | 4/2006 | Tang et al. |
| 2006/0092079 A1 | 5/2006 | de Rochemont |
| 2006/0094425 A1 | 5/2006 | Mickle et al. |
| 2006/0113955 A1 | 6/2006 | Nunally |
| 2006/0119532 A1 | 6/2006 | Yun et al. |
| 2006/0136004 A1 | 6/2006 | Cowan et al. |
| 2006/0160517 A1 | 7/2006 | Yoon |
| 2006/0183473 A1 | 8/2006 | Ukon |
| 2006/0190063 A1 | 8/2006 | Kanzius |
| 2006/0192913 A1 | 8/2006 | Shutou et al. |
| 2006/0199620 A1 | 9/2006 | Greene et al. |
| 2006/0238365 A1 | 10/2006 | Vecchione et al. |
| 2006/0266564 A1 | 11/2006 | Perlman et al. |
| 2006/0266917 A1 | 11/2006 | Baldis et al. |
| 2006/0278706 A1 | 12/2006 | Hatakayama et al. |
| 2006/0284593 A1 | 12/2006 | Nagy et al. |
| 2006/0287094 A1 | 12/2006 | Mahaffey et al. |
| 2007/0007821 A1 | 1/2007 | Rossetti |
| 2007/0019693 A1 | 1/2007 | Graham |
| 2007/0021140 A1 | 1/2007 | Keyes |
| 2007/0060185 A1 | 3/2007 | Simon et al. |
| 2007/0070490 A1 | 3/2007 | Tsunoda et al. |
| 2007/0090997 A1 | 4/2007 | Brown et al. |
| 2007/0093269 A1 | 4/2007 | Leabman et al. |
| 2007/0097653 A1 | 5/2007 | Gilliland et al. |
| 2007/0103110 A1 | 5/2007 | Sagoo |
| 2007/0106894 A1 | 5/2007 | Zhang |
| 2007/0109121 A1 | 5/2007 | Cohen |
| 2007/0139000 A1 | 6/2007 | Kozuma |
| 2007/0149162 A1 | 6/2007 | Greene et al. |

(56) References Cited

U.S. PATENT DOCUMENTS

| | | |
|---|---|---|
| 2007/0164868 A1 | 7/2007 | Deavours et al. |
| 2007/0173196 A1 | 7/2007 | Gallic |
| 2007/0173214 A1 | 7/2007 | Mickle et al. |
| 2007/0178857 A1 | 8/2007 | Greene et al. |
| 2007/0178945 A1 | 8/2007 | Cook et al. |
| 2007/0182367 A1 | 8/2007 | Partovi |
| 2007/0191074 A1 | 8/2007 | Harrist et al. |
| 2007/0191075 A1 | 8/2007 | Greene et al. |
| 2007/0197281 A1 | 8/2007 | Stronach |
| 2007/0210960 A1 | 9/2007 | Rofougaran et al. |
| 2007/0222681 A1 | 9/2007 | Greene et al. |
| 2007/0228833 A1 | 10/2007 | Stevens et al. |
| 2007/0229261 A1 | 10/2007 | Zimmerman et al. |
| 2007/0240297 A1 | 10/2007 | Yang et al. |
| 2007/0257634 A1 | 11/2007 | Leschin et al. |
| 2007/0273486 A1 | 11/2007 | Shiotsu |
| 2007/0291165 A1 | 12/2007 | Wang |
| 2007/0296639 A1 | 12/2007 | Hook et al. |
| 2007/0298846 A1 | 12/2007 | Greene et al. |
| 2008/0014897 A1 | 1/2008 | Cook et al. |
| 2008/0024376 A1 | 1/2008 | Norris et al. |
| 2008/0048917 A1 | 2/2008 | Achour et al. |
| 2008/0062062 A1 | 3/2008 | Borau et al. |
| 2008/0062255 A1 | 3/2008 | Gal |
| 2008/0067874 A1 | 3/2008 | Tseng |
| 2008/0074324 A1 | 3/2008 | Puzella et al. |
| 2008/0089277 A1 | 4/2008 | Aledander et al. |
| 2008/0110263 A1 | 5/2008 | Klessel et al. |
| 2008/0113816 A1 | 5/2008 | Mahaffey et al. |
| 2008/0122297 A1 | 5/2008 | Arai |
| 2008/0123383 A1 | 5/2008 | Shionoiri |
| 2008/0129536 A1 | 6/2008 | Randall et al. |
| 2008/0140278 A1 | 6/2008 | Breed |
| 2008/0169910 A1 | 7/2008 | Greene et al. |
| 2008/0197802 A1 | 8/2008 | Onishi |
| 2008/0204342 A1 | 8/2008 | Kharadly |
| 2008/0204350 A1 | 8/2008 | Tam et al. |
| 2008/0210762 A1 | 9/2008 | Osada et al. |
| 2008/0211458 A1 | 9/2008 | Lawther et al. |
| 2008/0233890 A1 | 9/2008 | Baker |
| 2008/0248758 A1 | 10/2008 | Schedelbeck et al. |
| 2008/0248846 A1 | 10/2008 | Stronach et al. |
| 2008/0258993 A1 | 10/2008 | Gummalla et al. |
| 2008/0266191 A1 | 10/2008 | Hilgers |
| 2008/0278378 A1 | 11/2008 | Chang et al. |
| 2008/0309452 A1 | 12/2008 | Zeine |
| 2009/0002493 A1 | 1/2009 | Kates |
| 2009/0010316 A1 | 1/2009 | Rofougaran et al. |
| 2009/0019183 A1 | 1/2009 | Wu et al. |
| 2009/0036065 A1 | 2/2009 | Siu |
| 2009/0039828 A1 | 2/2009 | Jakubowski |
| 2009/0047998 A1 | 2/2009 | Alberth, Jr. |
| 2009/0058354 A1 | 3/2009 | Harrison |
| 2009/0058361 A1 | 3/2009 | John |
| 2009/0058731 A1 | 3/2009 | Geary et al. |
| 2009/0060012 A1 | 3/2009 | Gresset et al. |
| 2009/0067198 A1 | 3/2009 | Graham et al. |
| 2009/0067208 A1 | 3/2009 | Martin et al. |
| 2009/0073066 A1 | 3/2009 | Jordon et al. |
| 2009/0096412 A1 | 4/2009 | Huang |
| 2009/0096413 A1 | 4/2009 | Partovi |
| 2009/0102292 A1 | 4/2009 | Cook et al. |
| 2009/0102296 A1 | 4/2009 | Greene et al. |
| 2009/0108679 A1 | 4/2009 | Porwal |
| 2009/0122847 A1 | 5/2009 | Nysen et al. |
| 2009/0128262 A1 | 5/2009 | Lee et al. |
| 2009/0157911 A1 | 6/2009 | Aihara |
| 2009/0174604 A1 | 7/2009 | Keskitalo |
| 2009/0180653 A1 | 7/2009 | Sjursen et al. |
| 2009/0200985 A1 | 8/2009 | Zane et al. |
| 2009/0206791 A1 | 8/2009 | Jung |
| 2009/0207090 A1 | 8/2009 | Pettus et al. |
| 2009/0207092 A1 | 8/2009 | Nysen et al. |
| 2009/0218884 A1 | 9/2009 | Soar |
| 2009/0218891 A1 | 9/2009 | McCollough |
| 2009/0219903 A1 | 9/2009 | Alamouti et al. |
| 2009/0243397 A1 | 10/2009 | Cook et al. |
| 2009/0256752 A1 | 10/2009 | Akkermans et al. |
| 2009/0264069 A1 | 10/2009 | Yamasuge |
| 2009/0271048 A1 | 10/2009 | Wakamatsu |
| 2009/0280866 A1 | 11/2009 | Lo et al. |
| 2009/0281678 A1 | 11/2009 | Wakamatsu |
| 2009/0284082 A1 | 11/2009 | Mohammadian |
| 2009/0284083 A1 | 11/2009 | Karalis et al. |
| 2009/0284220 A1 | 11/2009 | Toncich et al. |
| 2009/0284227 A1 | 11/2009 | Mohammadian et al. |
| 2009/0284325 A1 | 11/2009 | Rossiter et al. |
| 2009/0286475 A1 | 11/2009 | Toncich et al. |
| 2009/0286476 A1 | 11/2009 | Toncich et al. |
| 2009/0291634 A1 | 11/2009 | Saarisalo |
| 2009/0299175 A1 | 12/2009 | Bernstein et al. |
| 2009/0308936 A1 | 12/2009 | Nitzan et al. |
| 2009/0312046 A1 | 12/2009 | Clevenger et al. |
| 2009/0315412 A1 | 12/2009 | Yamamoto et al. |
| 2009/0322281 A1 | 12/2009 | Kamijo et al. |
| 2010/0001683 A1 | 1/2010 | Huang et al. |
| 2010/0007307 A1 | 1/2010 | Baarman et al. |
| 2010/0007569 A1 | 1/2010 | Sim et al. |
| 2010/0019686 A1 | 1/2010 | Gutierrez, Jr. |
| 2010/0019908 A1 | 1/2010 | Cho et al. |
| 2010/0026605 A1 | 2/2010 | Yang et al. |
| 2010/0027379 A1 | 2/2010 | Saulnier et al. |
| 2010/0029383 A1 | 2/2010 | Dai |
| 2010/0033021 A1 | 2/2010 | Bennett |
| 2010/0033390 A1 | 2/2010 | Alamouti et al. |
| 2010/0034238 A1 | 2/2010 | Bennett |
| 2010/0041453 A1 | 2/2010 | Grimm, Jr. |
| 2010/0044123 A1 | 2/2010 | Perlman et al. |
| 2010/0054200 A1 | 3/2010 | Tsai |
| 2010/0060534 A1 | 3/2010 | Oodachi |
| 2010/0066631 A1 | 3/2010 | Puzella et al. |
| 2010/0075607 A1 | 3/2010 | Hosoya |
| 2010/0079005 A1 | 4/2010 | Hyde et al. |
| 2010/0079011 A1 | 4/2010 | Hyde et al. |
| 2010/0082193 A1 | 4/2010 | Chiappetta |
| 2010/0087227 A1 | 4/2010 | Francos et al. |
| 2010/0090524 A1 | 4/2010 | Obayashi |
| 2010/0090656 A1 | 4/2010 | Shearer et al. |
| 2010/0109443 A1 | 5/2010 | Cook et al. |
| 2010/0117596 A1 | 5/2010 | Cook et al. |
| 2010/0117926 A1 | 5/2010 | DeJean, II |
| 2010/0119234 A1 | 5/2010 | Suematsu et al. |
| 2010/0123618 A1 | 5/2010 | Martin et al. |
| 2010/0123624 A1 | 5/2010 | Minear et al. |
| 2010/0124040 A1 | 5/2010 | Diebel et al. |
| 2010/0127660 A1 | 5/2010 | Cook et al. |
| 2010/0142418 A1 | 6/2010 | Nishioka et al. |
| 2010/0142509 A1 | 6/2010 | Zhu et al. |
| 2010/0148723 A1 | 6/2010 | Cook et al. |
| 2010/0151808 A1 | 6/2010 | Toncich et al. |
| 2010/0156721 A1 | 6/2010 | Alamouti et al. |
| 2010/0156741 A1 | 6/2010 | Vazquez et al. |
| 2010/0164296 A1 | 7/2010 | Kurs et al. |
| 2010/0164433 A1 | 7/2010 | Janefalker et al. |
| 2010/0167664 A1 | 7/2010 | Szini |
| 2010/0171461 A1 | 7/2010 | Baarman et al. |
| 2010/0171676 A1 | 7/2010 | Tani et al. |
| 2010/0174629 A1 | 7/2010 | Taylor et al. |
| 2010/0176934 A1 | 7/2010 | Chou et al. |
| 2010/0181961 A1 | 7/2010 | Novak et al. |
| 2010/0181964 A1 | 7/2010 | Huggins et al. |
| 2010/0194206 A1 | 8/2010 | Burdo et al. |
| 2010/0201189 A1 | 8/2010 | Kirby et al. |
| 2010/0201201 A1 | 8/2010 | Mobarhan et al. |
| 2010/0201314 A1 | 8/2010 | Toncich et al. |
| 2010/0207572 A1 | 8/2010 | Kirby et al. |
| 2010/0210233 A1 | 8/2010 | Cook et al. |
| 2010/0213895 A1 | 8/2010 | Keating et al. |
| 2010/0214177 A1 | 8/2010 | Parsche |
| 2010/0222010 A1 | 9/2010 | Ozaki et al. |
| 2010/0225270 A1 | 9/2010 | Jacobs et al. |
| 2010/0227570 A1 | 9/2010 | Hendin |
| 2010/0231470 A1 | 9/2010 | Lee et al. |
| 2010/0237709 A1 | 9/2010 | Hall et al. |

(56) References Cited

U.S. PATENT DOCUMENTS

| | | |
|---|---|---|
| 2010/0244576 A1 | 9/2010 | Hillan et al. |
| 2010/0253281 A1 | 10/2010 | Li |
| 2010/0256831 A1 | 10/2010 | Abramo et al. |
| 2010/0259110 A1 | 10/2010 | Kurs et al. |
| 2010/0259447 A1 | 10/2010 | Crouch |
| 2010/0264747 A1 | 10/2010 | Hall et al. |
| 2010/0277003 A1 | 11/2010 | Von Novak et al. |
| 2010/0277121 A1 | 11/2010 | Hall et al. |
| 2010/0279606 A1 | 11/2010 | Hillan et al. |
| 2010/0289341 A1 | 11/2010 | Ozaki et al. |
| 2010/0295372 A1 | 11/2010 | Hyde et al. |
| 2010/0308767 A1 | 12/2010 | Rofougaran et al. |
| 2010/0309079 A1 | 12/2010 | Rofougaran et al. |
| 2010/0309088 A1 | 12/2010 | Hyvonen et al. |
| 2010/0315045 A1 | 12/2010 | Zeine |
| 2010/0316163 A1 | 12/2010 | Forenza et al. |
| 2010/0327766 A1 | 12/2010 | Recker et al. |
| 2010/0328044 A1 | 12/2010 | Waffenschmidt et al. |
| 2010/0332401 A1 | 12/2010 | Prahlad et al. |
| 2011/0013198 A1 | 1/2011 | Shirley |
| 2011/0018360 A1 | 1/2011 | Baarman et al. |
| 2011/0028114 A1 | 2/2011 | Kerselaers |
| 2011/0031928 A1 | 2/2011 | Soar |
| 2011/0032149 A1 | 2/2011 | Leabman |
| 2011/0032866 A1 | 2/2011 | Leabman |
| 2011/0034190 A1 | 2/2011 | Leabman |
| 2011/0034191 A1 | 2/2011 | Leabman |
| 2011/0043047 A1 | 2/2011 | Karalis et al. |
| 2011/0043163 A1 | 2/2011 | Baarman et al. |
| 2011/0043327 A1 | 2/2011 | Baarman et al. |
| 2011/0050166 A1 | 3/2011 | Cook et al. |
| 2011/0055037 A1 | 3/2011 | Hayashigawa et al. |
| 2011/0056215 A1 | 3/2011 | Ham |
| 2011/0057607 A1 | 3/2011 | Carobolante |
| 2011/0057853 A1 | 3/2011 | Kim et al. |
| 2011/0062788 A1 | 3/2011 | Chen et al. |
| 2011/0074342 A1 | 3/2011 | MacLaughlin |
| 2011/0074349 A1 | 3/2011 | Ghovanloo |
| 2011/0074620 A1 | 3/2011 | Wintermantel |
| 2011/0078092 A1 | 3/2011 | Kim et al. |
| 2011/0090126 A1 | 4/2011 | Szini et al. |
| 2011/0109167 A1 | 5/2011 | Park et al. |
| 2011/0114401 A1 | 5/2011 | Kanno et al. |
| 2011/0115303 A1 | 5/2011 | Baarman et al. |
| 2011/0115432 A1 | 5/2011 | El-Maleh |
| 2011/0115605 A1 | 5/2011 | Dimig et al. |
| 2011/0121660 A1 | 5/2011 | Azancot et al. |
| 2011/0122018 A1 | 5/2011 | Tarng et al. |
| 2011/0122026 A1 | 5/2011 | DeLaquil et al. |
| 2011/0127845 A1 | 6/2011 | Walley et al. |
| 2011/0127952 A1 | 6/2011 | Walley et al. |
| 2011/0133655 A1 | 6/2011 | Recker et al. |
| 2011/0133691 A1 | 6/2011 | Hautanen |
| 2011/0148578 A1 | 6/2011 | Aloi et al. |
| 2011/0148595 A1 | 6/2011 | Miller et al. |
| 2011/0151789 A1 | 6/2011 | Viglione et al. |
| 2011/0154429 A1 | 6/2011 | Stantchev |
| 2011/0156493 A1 | 6/2011 | Bennett |
| 2011/0156494 A1 | 6/2011 | Mashinsky |
| 2011/0156640 A1 | 6/2011 | Moshfeghi |
| 2011/0163128 A1 | 7/2011 | Taguchi et al. |
| 2011/0175455 A1 | 7/2011 | Hashiguchi |
| 2011/0175461 A1 | 7/2011 | Tinaphong |
| 2011/0181120 A1 | 7/2011 | Liu et al. |
| 2011/0182245 A1 | 7/2011 | Malkamaki et al. |
| 2011/0184842 A1 | 7/2011 | Melen |
| 2011/0188207 A1 | 8/2011 | Won et al. |
| 2011/0193688 A1 | 8/2011 | Forsell |
| 2011/0194543 A1 | 8/2011 | Zhao et al. |
| 2011/0195722 A1 | 8/2011 | Walter et al. |
| 2011/0199046 A1 | 8/2011 | Tsai et al. |
| 2011/0215086 A1 | 9/2011 | Yeh |
| 2011/0217923 A1 | 9/2011 | Ma |
| 2011/0220634 A1 | 9/2011 | Yeh |
| 2011/0221389 A1 | 9/2011 | Won et al. |
| 2011/0222272 A1 | 9/2011 | Yeh |
| 2011/0227725 A1 | 9/2011 | Muirhead |
| 2011/0243040 A1 | 10/2011 | Khan et al. |
| 2011/0243050 A1 | 10/2011 | Yanover |
| 2011/0244913 A1 | 10/2011 | Kim et al. |
| 2011/0248573 A1 | 10/2011 | Kanno et al. |
| 2011/0248575 A1 | 10/2011 | Kim et al. |
| 2011/0249678 A1 | 10/2011 | Bonicatto |
| 2011/0254377 A1 | 10/2011 | Widmer et al. |
| 2011/0254503 A1 | 10/2011 | Widmer et al. |
| 2011/0259953 A1 | 10/2011 | Baarman et al. |
| 2011/0273977 A1 | 11/2011 | Shapira et al. |
| 2011/0278941 A1 | 11/2011 | Krishna et al. |
| 2011/0279226 A1 | 11/2011 | Chen et al. |
| 2011/0281535 A1 | 11/2011 | Low et al. |
| 2011/0282415 A1 | 11/2011 | Eckhoff et al. |
| 2011/0285213 A1 | 11/2011 | Kowalewski |
| 2011/0286374 A1 | 11/2011 | Shin et al. |
| 2011/0291489 A1 | 12/2011 | Tsai et al. |
| 2011/0302078 A1 | 12/2011 | Failing |
| 2011/0304216 A1 | 12/2011 | Baarman |
| 2011/0304437 A1 | 12/2011 | Beeler |
| 2011/0304521 A1 | 12/2011 | Ando et al. |
| 2012/0007441 A1 | 1/2012 | John |
| 2012/0013196 A1 | 1/2012 | Kim et al. |
| 2012/0013198 A1 | 1/2012 | Uramoto et al. |
| 2012/0013296 A1 | 1/2012 | Heydari et al. |
| 2012/0019419 A1 | 1/2012 | Prat et al. |
| 2012/0043887 A1 | 2/2012 | Mesibov |
| 2012/0051109 A1 | 3/2012 | Kim et al. |
| 2012/0051294 A1 | 3/2012 | Guillouard |
| 2012/0056486 A1 | 3/2012 | Endo et al. |
| 2012/0056741 A1 | 3/2012 | Zhu et al. |
| 2012/0068906 A1 | 3/2012 | Asher et al. |
| 2012/0074891 A1 | 3/2012 | Anderson et al. |
| 2012/0075072 A1 | 3/2012 | Pappu |
| 2012/0080944 A1 | 4/2012 | Recker et al. |
| 2012/0080957 A1 | 4/2012 | Cooper et al. |
| 2012/0086284 A1 | 4/2012 | Capanella et al. |
| 2012/0086615 A1 | 4/2012 | Norair |
| 2012/0095617 A1 | 4/2012 | Martin et al. |
| 2012/0098350 A1 | 4/2012 | Campanella et al. |
| 2012/0098485 A1 | 4/2012 | Kang et al. |
| 2012/0099675 A1 | 4/2012 | Kitamura et al. |
| 2012/0103562 A1 | 5/2012 | Clayton |
| 2012/0104849 A1 | 5/2012 | Jackson |
| 2012/0105252 A1 | 5/2012 | Wang |
| 2012/0112532 A1 | 5/2012 | Kesler et al. |
| 2012/0119914 A1 | 5/2012 | Uchida |
| 2012/0126743 A1 | 5/2012 | Rivers, Jr. |
| 2012/0132647 A1 | 5/2012 | Beverly et al. |
| 2012/0133214 A1 | 5/2012 | Yun et al. |
| 2012/0142291 A1 | 6/2012 | Rath et al. |
| 2012/0146426 A1 | 6/2012 | Sabo |
| 2012/0146576 A1 | 6/2012 | Partovi |
| 2012/0146577 A1 | 6/2012 | Tanabe |
| 2012/0147802 A1 | 6/2012 | Ukita et al. |
| 2012/0149307 A1 | 6/2012 | Terada et al. |
| 2012/0150670 A1 | 6/2012 | Taylor et al. |
| 2012/0153894 A1 | 6/2012 | Widmer et al. |
| 2012/0157019 A1 | 6/2012 | Li |
| 2012/0161531 A1 | 6/2012 | Kim et al. |
| 2012/0161544 A1 | 6/2012 | Kashiwagi et al. |
| 2012/0169276 A1 | 7/2012 | Wang |
| 2012/0169278 A1 | 7/2012 | Choi |
| 2012/0173418 A1 | 7/2012 | Beardsmore et al. |
| 2012/0179004 A1 | 7/2012 | Roesicke et al. |
| 2012/0181973 A1 | 7/2012 | Lyden |
| 2012/0182427 A1 | 7/2012 | Marshall |
| 2012/0188142 A1 | 7/2012 | Shashi et al. |
| 2012/0187851 A1 | 8/2012 | Huggins et al. |
| 2012/0193999 A1 | 8/2012 | Zeine |
| 2012/0200399 A1 | 8/2012 | Chae |
| 2012/0201153 A1 | 8/2012 | Bharadia et al. |
| 2012/0201173 A1 | 8/2012 | Jian et al. |
| 2012/0206299 A1 | 8/2012 | Valdes-Garcia |
| 2012/0211214 A1 | 8/2012 | Phan |
| 2012/0212071 A1 | 8/2012 | Miyabayashi et al. |
| 2012/0212072 A1 | 8/2012 | Miyabayashi et al. |

(56) References Cited

U.S. PATENT DOCUMENTS

| | | |
|---|---|---|
| 2012/0214462 A1 | 8/2012 | Chu et al. |
| 2012/0214536 A1 | 8/2012 | Kim et al. |
| 2012/0228392 A1 | 9/2012 | Cameron et al. |
| 2012/0228956 A1 | 9/2012 | Kamata |
| 2012/0231856 A1 | 9/2012 | Lee et al. |
| 2012/0235636 A1 | 9/2012 | Partovi |
| 2012/0242283 A1 | 9/2012 | Kim et al. |
| 2012/0248886 A1 | 10/2012 | Kesler et al. |
| 2012/0248888 A1 | 10/2012 | Kesler et al. |
| 2012/0248891 A1 | 10/2012 | Drennen |
| 2012/0249051 A1 | 10/2012 | Son et al. |
| 2012/0262002 A1 | 10/2012 | Widmer et al. |
| 2012/0265272 A1 | 10/2012 | Judkins |
| 2012/0267900 A1 | 10/2012 | Huffman et al. |
| 2012/0268238 A1 | 10/2012 | Park et al. |
| 2012/0274154 A1 | 11/2012 | DeLuca |
| 2012/0280650 A1 | 11/2012 | Kim et al. |
| 2012/0286582 A1 | 11/2012 | Kim et al. |
| 2012/0292993 A1 | 11/2012 | Mettler et al. |
| 2012/0293021 A1 | 11/2012 | Teggatz et al. |
| 2012/0293119 A1 | 11/2012 | Park et al. |
| 2012/0299389 A1 | 11/2012 | Lee et al. |
| 2012/0299540 A1 | 11/2012 | Perry |
| 2012/0299541 A1 | 11/2012 | Perry |
| 2012/0299542 A1 | 11/2012 | Perry |
| 2012/0300588 A1 | 11/2012 | Perry |
| 2012/0300592 A1 | 11/2012 | Perry |
| 2012/0300593 A1 | 11/2012 | Perry |
| 2012/0306284 A1 | 12/2012 | Lee et al. |
| 2012/0306433 A1 | 12/2012 | Kim et al. |
| 2012/0306705 A1 | 12/2012 | Sakurai et al. |
| 2012/0306707 A1 | 12/2012 | Yang et al. |
| 2012/0306720 A1 | 12/2012 | Tanmi et al. |
| 2012/0307873 A1 | 12/2012 | Kim et al. |
| 2012/0309295 A1 | 12/2012 | Maguire |
| 2012/0309308 A1 | 12/2012 | Kim et al. |
| 2012/0309332 A1 | 12/2012 | Liao |
| 2012/0313446 A1 | 12/2012 | Park et al. |
| 2012/0313449 A1 | 12/2012 | Kurs |
| 2012/0313835 A1 | 12/2012 | Gebretnsae |
| 2012/0326660 A1 | 12/2012 | Lu et al. |
| 2013/0002550 A1 | 1/2013 | Zalewski |
| 2013/0005252 A1 | 1/2013 | Lee et al. |
| 2013/0018439 A1 | 1/2013 | Chow et al. |
| 2013/0024059 A1 | 1/2013 | Miller et al. |
| 2013/0026981 A1 | 1/2013 | Van Der Lee |
| 2013/0026982 A1 | 1/2013 | Rothenbaum |
| 2013/0032589 A1 | 2/2013 | Chung |
| 2013/0033571 A1 | 2/2013 | Steen |
| 2013/0038124 A1 | 2/2013 | Newdoll et al. |
| 2013/0038402 A1 | 2/2013 | Karalis et al. |
| 2013/0043738 A1 | 2/2013 | Park et al. |
| 2013/0044035 A1 | 2/2013 | Zhuang |
| 2013/0049471 A1 | 2/2013 | Oleynik |
| 2013/0049475 A1 | 2/2013 | Kim et al. |
| 2013/0049484 A1 | 2/2013 | Weissentern et al. |
| 2013/0057078 A1 | 3/2013 | Lee |
| 2013/0057205 A1 | 3/2013 | Lee et al. |
| 2013/0057210 A1 | 3/2013 | Negaard et al. |
| 2013/0057364 A1 | 3/2013 | Kesler et al. |
| 2013/0058379 A1 | 3/2013 | Kim et al. |
| 2013/0062959 A1 | 3/2013 | Lee et al. |
| 2013/0063082 A1 | 3/2013 | Lee et al. |
| 2013/0063143 A1 | 3/2013 | Adalsteinsson et al. |
| 2013/0063266 A1 | 3/2013 | Yunker et al. |
| 2013/0069444 A1 | 3/2013 | Waffenschmidt et al. |
| 2013/0076308 A1 | 3/2013 | Niskala et al. |
| 2013/0077650 A1 | 3/2013 | Traxler et al. |
| 2013/0078918 A1 | 3/2013 | Crowley et al. |
| 2013/0082651 A1 | 4/2013 | Park et al. |
| 2013/0082653 A1 | 4/2013 | Lee et al. |
| 2013/0083774 A1 | 4/2013 | Son et al. |
| 2013/0088082 A1 | 4/2013 | Kang et al. |
| 2013/0088090 A1 | 4/2013 | Wu |
| 2013/0088192 A1 | 4/2013 | Eaton |
| 2013/0088331 A1 | 4/2013 | Cho |
| 2013/0093388 A1 | 4/2013 | Partovi |
| 2013/0099389 A1 | 4/2013 | Hong et al. |
| 2013/0099586 A1 | 4/2013 | Kato |
| 2013/0106197 A1 | 5/2013 | Bae et al. |
| 2013/0107023 A1 | 5/2013 | Tanaka et al. |
| 2013/0119777 A1 | 5/2013 | Rees |
| 2013/0119778 A1 | 5/2013 | Jung |
| 2013/0119929 A1 | 5/2013 | Partovi |
| 2013/0120052 A1 | 5/2013 | Siska |
| 2013/0120205 A1 | 5/2013 | Thomson et al. |
| 2013/0120206 A1 | 5/2013 | Biancotto et al. |
| 2013/0120217 A1 | 5/2013 | Ueda et al. |
| 2013/0130621 A1 | 5/2013 | Kim et al. |
| 2013/0132010 A1 | 5/2013 | Winger et al. |
| 2013/0134923 A1 | 5/2013 | Smith |
| 2013/0137455 A1 | 5/2013 | Xia |
| 2013/0141037 A1 | 6/2013 | Jenwatanavet et al. |
| 2013/0148341 A1 | 6/2013 | Williams |
| 2013/0149975 A1 | 6/2013 | Yu et al. |
| 2013/0154387 A1 | 6/2013 | Lee et al. |
| 2013/0155748 A1 | 6/2013 | Sundstrom |
| 2013/0157729 A1 | 6/2013 | Tabe |
| 2013/0162335 A1 | 6/2013 | Kim et al. |
| 2013/0169061 A1 | 7/2013 | Microshnichenko et al. |
| 2013/0169219 A1 | 7/2013 | Gray |
| 2013/0169348 A1 | 7/2013 | Shi |
| 2013/0171939 A1 | 7/2013 | Tian et al. |
| 2013/0175877 A1 | 7/2013 | Abe et al. |
| 2013/0178253 A1 | 7/2013 | Karaoguz |
| 2013/0181881 A1 | 7/2013 | Christie et al. |
| 2013/0187475 A1 | 7/2013 | Vendik |
| 2013/0190031 A1 | 7/2013 | Persson et al. |
| 2013/0193769 A1 | 8/2013 | Mehta et al. |
| 2013/0197320 A1 | 8/2013 | Albert et al. |
| 2013/0200064 A1 | 8/2013 | Alexander |
| 2013/0207477 A1 | 8/2013 | Nam et al. |
| 2013/0207604 A1 | 8/2013 | Zeine |
| 2013/0207879 A1 | 8/2013 | Rada et al. |
| 2013/0210357 A1 | 8/2013 | Qin et al. |
| 2013/0221757 A1 | 8/2013 | Cho et al. |
| 2013/0222201 A1 | 8/2013 | Ma et al. |
| 2013/0234530 A1 | 9/2013 | Miyauchi |
| 2013/0234536 A1 | 9/2013 | Chemishkian et al. |
| 2013/0234658 A1 | 9/2013 | Endo et al. |
| 2013/0241306 A1 | 9/2013 | Aber et al. |
| 2013/0241468 A1 | 9/2013 | Moshfeghi |
| 2013/0241474 A1 | 9/2013 | Moshfeghi |
| 2013/0249478 A1 | 9/2013 | Hirano |
| 2013/0249479 A1 | 9/2013 | Partovi |
| 2013/0249682 A1 | 9/2013 | Van Wiemeersch et al. |
| 2013/0250102 A1 | 9/2013 | Scanlon et al. |
| 2013/0254578 A1 | 9/2013 | Huang et al. |
| 2013/0264997 A1 | 10/2013 | Lee et al. |
| 2013/0268782 A1 | 10/2013 | Tam et al. |
| 2013/0270923 A1 | 10/2013 | Cook et al. |
| 2013/0278076 A1 | 10/2013 | Proud |
| 2013/0278209 A1 | 10/2013 | Von Novak |
| 2013/0285464 A1 | 10/2013 | Miwa |
| 2013/0285477 A1 | 10/2013 | Lo et al. |
| 2013/0285606 A1 | 10/2013 | Ben-Shalom et al. |
| 2013/0288600 A1 | 10/2013 | Kuusilinna et al. |
| 2013/0288617 A1 | 10/2013 | Kim et al. |
| 2013/0293423 A1 | 11/2013 | Moshfeghi |
| 2013/0300356 A1 | 11/2013 | Yang |
| 2013/0307751 A1 | 11/2013 | Yu-Juin et al. |
| 2013/0310020 A1 | 11/2013 | Kazuhiro |
| 2013/0311798 A1 | 11/2013 | Sultenfuss |
| 2013/0328417 A1 | 12/2013 | Takeuchi |
| 2013/0334883 A1 | 12/2013 | Kim et al. |
| 2013/0339108 A1 | 12/2013 | Ryder et al. |
| 2013/0343208 A1 | 12/2013 | Sexton et al. |
| 2013/0343251 A1 | 12/2013 | Zhang |
| 2013/0343585 A1 | 12/2013 | Bennett et al. |
| 2014/0001846 A1 | 1/2014 | Mosebrook |
| 2014/0001875 A1 | 1/2014 | Nahidipour |
| 2014/0001876 A1 | 1/2014 | Fujiwara et al. |
| 2014/0006017 A1 | 1/2014 | Sen |

(56) References Cited

U.S. PATENT DOCUMENTS

| | | |
|---|---|---|
| 2014/0008992 A1* | 1/2014 | Leabman ............... A41D 1/02 307/104 |
| 2014/0008993 A1 | 1/2014 | Leabman |
| 2014/0009108 A1 | 1/2014 | Leabman |
| 2014/0009110 A1 | 1/2014 | Lee |
| 2014/0011531 A1 | 1/2014 | Burstrom et al. |
| 2014/0015336 A1 | 1/2014 | Weber et al. |
| 2014/0015344 A1 | 1/2014 | Mohamadi |
| 2014/0021907 A1 | 1/2014 | Yun et al. |
| 2014/0021908 A1 | 1/2014 | McCool |
| 2014/0035524 A1 | 2/2014 | Zeine |
| 2014/0035526 A1 | 2/2014 | Tripathi et al. |
| 2014/0035786 A1 | 2/2014 | Ley |
| 2014/0043248 A1 | 2/2014 | Yeh |
| 2014/0049422 A1 | 2/2014 | Von Novak et al. |
| 2014/0054971 A1 | 2/2014 | Kissin |
| 2014/0055098 A1 | 2/2014 | Lee et al. |
| 2014/0057618 A1 | 2/2014 | Zirwas et al. |
| 2014/0062395 A1 | 3/2014 | Kwon et al. |
| 2014/0082435 A1 | 3/2014 | Kitgawa |
| 2014/0086125 A1 | 3/2014 | Polo et al. |
| 2014/0086592 A1 | 3/2014 | Nakahara et al. |
| 2014/0091756 A1 | 4/2014 | Ofstein et al. |
| 2014/0091968 A1 | 4/2014 | Harel et al. |
| 2014/0091974 A1 | 4/2014 | Desclos et al. |
| 2014/0103869 A1 | 4/2014 | Radovic |
| 2014/0104157 A1 | 4/2014 | Burns |
| 2014/0111147 A1 | 4/2014 | Soar |
| 2014/0111153 A1 | 4/2014 | Kwon et al. |
| 2014/0113689 A1 | 4/2014 | Lee |
| 2014/0117946 A1 | 5/2014 | Muller et al. |
| 2014/0118140 A1 | 5/2014 | Amis |
| 2014/0128107 A1 | 5/2014 | An |
| 2014/0132210 A1 | 5/2014 | Partovi |
| 2014/0133279 A1 | 5/2014 | Khuri-Yakub |
| 2014/0139034 A1 | 5/2014 | Sankar et al. |
| 2014/0139039 A1 | 5/2014 | Cook et al. |
| 2014/0139180 A1 | 5/2014 | Kim et al. |
| 2014/0141838 A1 | 5/2014 | Cai et al. |
| 2014/0142876 A1 | 5/2014 | John et al. |
| 2014/0143933 A1 | 5/2014 | Low et al. |
| 2014/0145879 A1 | 5/2014 | Pan |
| 2014/0145884 A1 | 5/2014 | Dang et al. |
| 2014/0152117 A1 | 6/2014 | Sanker |
| 2014/0159651 A1 | 6/2014 | Von Novak et al. |
| 2014/0159652 A1 | 6/2014 | Hall et al. |
| 2014/0159662 A1 | 6/2014 | Furui |
| 2014/0159667 A1 | 6/2014 | Kim et al. |
| 2014/0169385 A1 | 6/2014 | Hadani et al. |
| 2014/0175893 A1 | 6/2014 | Sengupta et al. |
| 2014/0176054 A1 | 6/2014 | Porat et al. |
| 2014/0176061 A1 | 6/2014 | Cheatham, III et al. |
| 2014/0176082 A1 | 6/2014 | Visser |
| 2014/0177399 A1 | 6/2014 | Teng et al. |
| 2014/0183964 A1 | 7/2014 | Walley |
| 2014/0184148 A1 | 7/2014 | Van Der Lee et al. |
| 2014/0184155 A1 | 7/2014 | Cha |
| 2014/0184163 A1 | 7/2014 | Das et al. |
| 2014/0184170 A1 | 7/2014 | Jeong |
| 2014/0191568 A1 | 7/2014 | Partovi |
| 2014/0191818 A1 | 7/2014 | Waffenschmidt et al. |
| 2014/0194092 A1 | 7/2014 | Wanstedt et al. |
| 2014/0194095 A1 | 7/2014 | Wanstedt et al. |
| 2014/0197691 A1 | 7/2014 | Wang |
| 2014/0203629 A1 | 7/2014 | Hoffman et al. |
| 2014/0206384 A1 | 7/2014 | Kim et al. |
| 2014/0210281 A1 | 7/2014 | Ito et al. |
| 2014/0217955 A1 | 8/2014 | Lin |
| 2014/0217967 A1 | 8/2014 | Zeine et al. |
| 2014/0225805 A1 | 8/2014 | Pan et al. |
| 2014/0232320 A1 | 8/2014 | Ento July et al. |
| 2014/0232610 A1 | 8/2014 | Shigemoto et al. |
| 2014/0239733 A1 | 8/2014 | Mach et al. |
| 2014/0241231 A1 | 8/2014 | Zeine |
| 2014/0245036 A1 | 8/2014 | Oishi |
| 2014/0246416 A1 | 9/2014 | White |
| 2014/0247152 A1 | 9/2014 | Proud |
| 2014/0252813 A1 | 9/2014 | Lee et al. |
| 2014/0252866 A1 | 9/2014 | Walsh et al. |
| 2014/0265725 A1 | 9/2014 | Angle et al. |
| 2014/0265727 A1 | 9/2014 | Berte |
| 2014/0265943 A1 | 9/2014 | Angle et al. |
| 2014/0266025 A1 | 9/2014 | Jakubowski |
| 2014/0266946 A1 | 9/2014 | Bily et al. |
| 2014/0273819 A1 | 9/2014 | Nadakuduti et al. |
| 2014/0273892 A1 | 9/2014 | Nourbakhsh |
| 2014/0281655 A1 | 9/2014 | Angle et al. |
| 2014/0292090 A1 | 10/2014 | Cordeiro et al. |
| 2014/0292451 A1 | 10/2014 | Zimmerman |
| 2014/0300452 A1 | 10/2014 | Rofe et al. |
| 2014/0312706 A1 | 10/2014 | Fiorello et al. |
| 2014/0325218 A1 | 10/2014 | Shimizu et al. |
| 2014/0327320 A1 | 11/2014 | Muhs et al. |
| 2014/0327390 A1 | 11/2014 | Park et al. |
| 2014/0333142 A1 | 11/2014 | Desrosiers |
| 2014/0346860 A1 | 11/2014 | Aubry et al. |
| 2014/0354063 A1 | 12/2014 | Leabman et al. |
| 2014/0354221 A1 | 12/2014 | Leabman et al. |
| 2014/0355718 A1 | 12/2014 | Guan et al. |
| 2014/0357309 A1 | 12/2014 | Leabman et al. |
| 2014/0368048 A1 | 12/2014 | Leabman et al. |
| 2014/0368161 A1 | 12/2014 | Leabman et al. |
| 2014/0368405 A1 | 12/2014 | Ek et al. |
| 2014/0375139 A1 | 12/2014 | Tsukamoto |
| 2014/0375253 A1 | 12/2014 | Leabman et al. |
| 2014/0375255 A1 | 12/2014 | Leabman et al. |
| 2014/0375258 A1 | 12/2014 | Arkhipenkov |
| 2014/0375261 A1 | 12/2014 | Manova-Elssibony et al. |
| 2014/0376646 A1 | 12/2014 | Leabman et al. |
| 2015/0001949 A1 | 1/2015 | Leabman et al. |
| 2015/0002086 A1 | 1/2015 | Matos et al. |
| 2015/0003207 A1 | 1/2015 | Lee et al. |
| 2015/0008980 A1 | 1/2015 | Kim et al. |
| 2015/0011160 A1 | 1/2015 | Uurgovan et al. |
| 2015/0015180 A1 | 1/2015 | Miller et al. |
| 2015/0015182 A1 | 1/2015 | Brandtman et al. |
| 2015/0015192 A1 | 1/2015 | Leabamn |
| 2015/0015194 A1 | 1/2015 | Leabman et al. |
| 2015/0015195 A1 | 1/2015 | Leabman et al. |
| 2015/0021990 A1 | 1/2015 | Myer et al. |
| 2015/0022008 A1 | 1/2015 | Leabman et al. |
| 2015/0022009 A1 | 1/2015 | Leabman et al. |
| 2015/0022010 A1 | 1/2015 | Leabman et al. |
| 2015/0022194 A1 | 1/2015 | Almalki et al. |
| 2015/0023204 A1 | 1/2015 | Wil et al. |
| 2015/0028688 A1 | 1/2015 | Masaoka |
| 2015/0028694 A1 | 1/2015 | Leabman et al. |
| 2015/0028697 A1 | 1/2015 | Leabman et al. |
| 2015/0028875 A1 | 1/2015 | Irie et al. |
| 2015/0029397 A1 | 1/2015 | Leabman et al. |
| 2015/0035378 A1 | 2/2015 | Calhoun et al. |
| 2015/0035715 A1 | 2/2015 | Kim et al. |
| 2015/0039482 A1 | 2/2015 | Fuinaga |
| 2015/0041459 A1 | 2/2015 | Leabman et al. |
| 2015/0042264 A1 | 2/2015 | Leabman et al. |
| 2015/0042265 A1 | 2/2015 | Leabman et al. |
| 2015/0044977 A1 | 2/2015 | Ramasamy et al. |
| 2015/0046526 A1 | 2/2015 | Bush et al. |
| 2015/0061404 A1 | 3/2015 | Lamenza et al. |
| 2015/0076917 A1 | 3/2015 | Leabman et al. |
| 2015/0076927 A1 | 3/2015 | Leabman et al. |
| 2015/0077036 A1 | 3/2015 | Leabman et al. |
| 2015/0077037 A1 | 3/2015 | Leabman et al. |
| 2015/0091520 A1 | 4/2015 | Blum et al. |
| 2015/0091706 A1 | 4/2015 | Chemishkian et al. |
| 2015/0097442 A1 | 4/2015 | Muurinen |
| 2015/0097663 A1 | 4/2015 | Sloo et al. |
| 2015/0102681 A1 | 4/2015 | Leabman et al. |
| 2015/0102764 A1 | 4/2015 | Leabman et al. |
| 2015/0102769 A1 | 4/2015 | Leabman et al. |
| 2015/0102942 A1 | 4/2015 | Houser et al. |
| 2015/0102973 A1 | 4/2015 | Hand et al. |
| 2015/0108848 A1 | 4/2015 | Joehren |
| 2015/0109181 A1 | 4/2015 | Hyde et al. |

(56) References Cited

U.S. PATENT DOCUMENTS

| | | |
|---|---|---|
| 2015/0115877 A1 | 4/2015 | Aria et al. |
| 2015/0115878 A1 | 4/2015 | Park |
| 2015/0116153 A1 | 4/2015 | Chen et al. |
| 2015/0123483 A1 | 5/2015 | Leabman et al. |
| 2015/0123496 A1 | 5/2015 | Leabman et al. |
| 2015/0128733 A1 | 5/2015 | Taylor et al. |
| 2015/0130285 A1 | 5/2015 | Leabman et al. |
| 2015/0130293 A1 | 5/2015 | Hajimiri et al. |
| 2015/0137612 A1 | 5/2015 | Yamakawa et al. |
| 2015/0148664 A1 | 5/2015 | Stolka et al. |
| 2015/0155737 A1 | 6/2015 | Mayo |
| 2015/0155738 A1 | 6/2015 | Leabman et al. |
| 2015/0162662 A1 | 6/2015 | Chen et al. |
| 2015/0162751 A1 | 6/2015 | Leabman et al. |
| 2015/0162779 A1 | 6/2015 | Lee et al. |
| 2015/0171512 A1 | 6/2015 | Chen et al. |
| 2015/0171513 A1 | 6/2015 | Chen et al. |
| 2015/0171656 A1 | 6/2015 | Leabman et al. |
| 2015/0171658 A1 | 6/2015 | Manova-Elssibony et al. |
| 2015/0171931 A1 | 6/2015 | Won et al. |
| 2015/0177326 A1 | 6/2015 | Chakraborty et al. |
| 2015/0180133 A1 | 6/2015 | Hunt |
| 2015/0180249 A1 | 6/2015 | Jeon et al. |
| 2015/0180284 A1 | 6/2015 | Kang et al. |
| 2015/0181117 A1 | 6/2015 | Park et al. |
| 2015/0187491 A1 | 7/2015 | Yanagawa |
| 2015/0188352 A1 | 7/2015 | Peek et al. |
| 2015/0199665 A1 | 7/2015 | Chu |
| 2015/0201385 A1 | 7/2015 | Mercer et al. |
| 2015/0207333 A1 | 7/2015 | Baarman et al. |
| 2015/0207542 A1 | 7/2015 | Zeine |
| 2015/0222126 A1 | 8/2015 | Leabman et al. |
| 2015/0233987 A1 | 8/2015 | Von Novak, III et al. |
| 2015/0234144 A1 | 8/2015 | Cameron et al. |
| 2015/0236520 A1 | 8/2015 | Baarman |
| 2015/0244070 A1 | 8/2015 | Cheng et al. |
| 2015/0244080 A1 | 8/2015 | Gregoire |
| 2015/0244187 A1 | 8/2015 | Horie |
| 2015/0244201 A1 | 8/2015 | Chu |
| 2015/0244341 A1 | 8/2015 | Ritter et al. |
| 2015/0249484 A1 | 9/2015 | Mach et al. |
| 2015/0255989 A1 | 9/2015 | Walley et al. |
| 2015/0256097 A1 | 9/2015 | Gudan et al. |
| 2015/0260835 A1 | 9/2015 | Widmer et al. |
| 2015/0262465 A1 | 9/2015 | Pritchett |
| 2015/0263534 A1 | 9/2015 | Lee et al. |
| 2015/0263548 A1 | 9/2015 | Cooper |
| 2015/0270618 A1 | 9/2015 | Zhu et al. |
| 2015/0270622 A1 | 9/2015 | Takasaki et al. |
| 2015/0270741 A1 | 9/2015 | Leabman et al. |
| 2015/0278558 A1 | 10/2015 | Priev et al. |
| 2015/0280429 A1 | 10/2015 | Makita et al. |
| 2015/0280484 A1 | 10/2015 | Radziemski et al. |
| 2015/0288074 A1 | 10/2015 | Harper et al. |
| 2015/0288438 A1 | 10/2015 | Maltsev et al. |
| 2015/0311585 A1 | 10/2015 | Church et al. |
| 2015/0312721 A1 | 10/2015 | Singh |
| 2015/0318729 A1 | 11/2015 | Leabman |
| 2015/0326024 A1 | 11/2015 | Bell et al. |
| 2015/0326025 A1 | 11/2015 | Bell et al. |
| 2015/0326051 A1 | 11/2015 | Bell et al. |
| 2015/0326063 A1 | 11/2015 | Leabman et al. |
| 2015/0326068 A1 | 11/2015 | Bell et al. |
| 2015/0326069 A1 | 11/2015 | Petras et al. |
| 2015/0326070 A1 | 11/2015 | Petras et al. |
| 2015/0326071 A1 | 11/2015 | Contopanagos |
| 2015/0326072 A1 | 11/2015 | Petras et al. |
| 2015/0326142 A1 | 11/2015 | Petras et al. |
| 2015/0326143 A1 | 11/2015 | Petras et al. |
| 2015/0327085 A1 | 11/2015 | Hadani |
| 2015/0333528 A1 | 11/2015 | Leabman |
| 2015/0333529 A1 | 11/2015 | Leabman |
| 2015/0333573 A1 | 11/2015 | Leabman |
| 2015/0333800 A1 | 11/2015 | Perry et al. |
| 2015/0339497 A1 | 11/2015 | Kurian |
| 2015/0340759 A1 | 11/2015 | Bridgelall et al. |
| 2015/0340903 A1 | 11/2015 | Bell et al. |
| 2015/0340909 A1 | 11/2015 | Bell et al. |
| 2015/0340910 A1 | 11/2015 | Petras et al. |
| 2015/0340911 A1 | 11/2015 | Bell et al. |
| 2015/0341087 A1 | 11/2015 | Moore et al. |
| 2015/0349574 A1 | 12/2015 | Leabman |
| 2015/0358222 A1 | 12/2015 | Berger et al. |
| 2015/0365137 A1 | 12/2015 | Miller et al. |
| 2015/0365138 A1 | 12/2015 | Miller et al. |
| 2016/0005068 A1 | 1/2016 | Im et al. |
| 2016/0012695 A1 | 1/2016 | Bell et al. |
| 2016/0013560 A1 | 1/2016 | Daniels |
| 2016/0013656 A1 | 1/2016 | Bell et al. |
| 2016/0013677 A1 | 1/2016 | Bell et al. |
| 2016/0013678 A1 | 1/2016 | Bell et al. |
| 2016/0013855 A1 | 1/2016 | Campos |
| 2016/0020636 A1 | 1/2016 | Khlat |
| 2016/0020647 A1 | 1/2016 | Leabman et al. |
| 2016/0020649 A1 | 1/2016 | Bell et al. |
| 2016/0020830 A1 | 1/2016 | Bell et al. |
| 2016/0028403 A1 | 1/2016 | McCaughan et al. |
| 2016/0033254 A1 | 2/2016 | Zeine et al. |
| 2016/0042206 A1 | 2/2016 | Pesavento et al. |
| 2016/0043571 A1 | 2/2016 | Kesler et al. |
| 2016/0054396 A1 | 2/2016 | Bell et al. |
| 2016/0054440 A1 | 2/2016 | Younis |
| 2016/0056635 A1 | 2/2016 | Bell |
| 2016/0056640 A1 | 2/2016 | Mao |
| 2016/0056669 A1 | 2/2016 | Bell |
| 2016/0056966 A1 | 2/2016 | Bell |
| 2016/0065005 A1 | 3/2016 | Won et al. |
| 2016/0079799 A1 | 3/2016 | Khlat |
| 2016/0087483 A1 | 3/2016 | Hietala et al. |
| 2016/0087486 A1 | 3/2016 | Pogorelik et al. |
| 2016/0094091 A1 | 3/2016 | Shin et al. |
| 2016/0094092 A1 | 3/2016 | Davlantes et al. |
| 2016/0099601 A1 | 4/2016 | Leabman et al. |
| 2016/0099602 A1 | 4/2016 | Leabman et al. |
| 2016/0099609 A1 | 4/2016 | Leabman et al. |
| 2016/0099610 A1 | 4/2016 | Leabman et al. |
| 2016/0099611 A1 | 4/2016 | Leabman et al. |
| 2016/0099612 A1 | 4/2016 | Leabman et al. |
| 2016/0099613 A1 | 4/2016 | Leabman et al. |
| 2016/0099614 A1 | 4/2016 | Leabman et al. |
| 2016/0099755 A1 | 4/2016 | Leabman et al. |
| 2016/0099756 A1 | 4/2016 | Leabman et al. |
| 2016/0099757 A1 | 4/2016 | Leabman et al. |
| 2016/0099758 A1 | 4/2016 | Leabman et al. |
| 2016/0100124 A1 | 4/2016 | Leabman et al. |
| 2016/0100312 A1 | 4/2016 | Bell et al. |
| 2016/0112787 A1 | 4/2016 | Rich |
| 2016/0126749 A1 | 5/2016 | Shichino et al. |
| 2016/0126752 A1 | 5/2016 | Vuori et al. |
| 2016/0126776 A1 | 5/2016 | Kim et al. |
| 2016/0141908 A1 | 5/2016 | Jaki et al. |
| 2016/0164563 A1 | 6/2016 | Khawand et al. |
| 2016/0181849 A1 | 6/2016 | Govindaraj |
| 2016/0181854 A1 | 6/2016 | Leabman |
| 2016/0181867 A1 | 6/2016 | Daniel et al. |
| 2016/0181873 A1 | 6/2016 | Mitcheson et al. |
| 2016/0191121 A1 | 6/2016 | Bell |
| 2016/0197522 A1 | 7/2016 | Zeine et al. |
| 2016/0202343 A1 | 7/2016 | Okutsu |
| 2016/0204622 A1 | 7/2016 | Leabman |
| 2016/0204642 A1 | 7/2016 | Oh |
| 2016/0218545 A1 | 7/2016 | Schroeder et al. |
| 2016/0233582 A1 | 8/2016 | Piskun |
| 2016/0238365 A1 | 8/2016 | Wixey et al. |
| 2016/0240908 A1 | 8/2016 | Strong |
| 2016/0248276 A1 | 8/2016 | Hong et al. |
| 2016/0294225 A1 | 10/2016 | Blum et al. |
| 2016/0299210 A1 | 10/2016 | Zeine |
| 2016/0301240 A1 | 10/2016 | Zeine |
| 2016/0322868 A1 | 11/2016 | Akuzawa et al. |
| 2016/0323000 A1 | 11/2016 | Liu et al. |
| 2016/0336804 A1 | 11/2016 | Son et al. |
| 2016/0339258 A1 | 11/2016 | Perryman et al. |
| 2016/0344098 A1 | 11/2016 | Ming |

(56) References Cited

U.S. PATENT DOCUMENTS

| | | |
|---|---|---|
| 2016/0359367 A1 | 12/2016 | Rothschild |
| 2016/0380464 A1 | 12/2016 | Chin et al. |
| 2016/0380466 A1 | 12/2016 | Yang et al. |
| 2017/0005481 A1 | 1/2017 | Von Novak, III |
| 2017/0005516 A9 | 1/2017 | Leabman et al. |
| 2017/0005524 A1 | 1/2017 | Akuzawa et al. |
| 2017/0005530 A1 | 1/2017 | Zeine et al. |
| 2017/0012448 A1 | 1/2017 | Miller et al. |
| 2017/0025887 A1 | 1/2017 | Hyun et al. |
| 2017/0025903 A1 | 1/2017 | Song et al. |
| 2017/0026087 A1 | 1/2017 | Tanabe |
| 2017/0040700 A1 | 2/2017 | Leung |
| 2017/0043675 A1 | 2/2017 | Jones et al. |
| 2017/0047784 A1 | 2/2017 | Jung et al. |
| 2017/0187225 A1 | 2/2017 | Hosseini |
| 2017/0063168 A1 | 3/2017 | Uchida |
| 2017/0077733 A1 | 3/2017 | Jeong et al. |
| 2017/0077735 A1 | 3/2017 | Leabman |
| 2017/0077764 A1 | 3/2017 | Bell et al. |
| 2017/0077765 A1 | 3/2017 | Bell et al. |
| 2017/0077979 A1 | 3/2017 | Papa et al. |
| 2017/0077995 A1 | 3/2017 | Leabman |
| 2017/0085120 A1 | 3/2017 | Leabman et al. |
| 2017/0085127 A1 | 3/2017 | Leabman |
| 2017/0085437 A1 | 3/2017 | Condeixa et al. |
| 2017/0092115 A1 | 3/2017 | Sloo et al. |
| 2017/0104263 A1 | 4/2017 | Hosseini |
| 2017/0110886 A1 | 4/2017 | Reynolds et al. |
| 2017/0110888 A1 | 4/2017 | Leabman |
| 2017/0110889 A1 | 4/2017 | Bell |
| 2017/0110914 A1 | 4/2017 | Bell |
| 2017/0127196 A1* | 5/2017 | Blum .................... H04R 25/554 |
| 2017/0134686 A9 | 5/2017 | Leabman |
| 2017/0141582 A1 | 5/2017 | Adolf et al. |
| 2017/0141583 A1 | 5/2017 | Adolf et al. |
| 2017/0163076 A1 | 6/2017 | Park et al. |
| 2017/0168595 A1 | 6/2017 | Sakaguchi et al. |
| 2017/0179763 A9 | 6/2017 | Leabman |
| 2017/0179771 A1 | 6/2017 | Leabman |
| 2017/0180884 A1* | 6/2017 | Ozden .................... H04R 25/554 |
| 2017/0187198 A1 | 6/2017 | Leabman |
| 2017/0187222 A1 | 6/2017 | Hosseini |
| 2017/0187223 A1 | 6/2017 | Hosseini |
| 2017/0187228 A1 | 6/2017 | Hosseini |
| 2017/0187248 A1 | 6/2017 | Leabman |
| 2017/0214422 A1 | 7/2017 | Na et al. |
| 2017/0236638 A1* | 8/2017 | Mayo .................... H01F 38/14 307/104 |
| 2017/0274787 A1 | 9/2017 | Salter et al. |
| 2017/0338695 A1 | 11/2017 | Port |
| 2018/0040929 A1 | 2/2018 | Chappelle |
| 2018/0048178 A1 | 2/2018 | Leabman |
| 2018/0090992 A1 | 3/2018 | Shrivastava et al. |
| 2018/0123400 A1 | 5/2018 | Leabman |
| 2018/0131238 A1 | 5/2018 | Leabman |
| 2018/0159355 A1 | 6/2018 | Leabman |
| 2018/0166924 A1 | 6/2018 | Hosseini |
| 2018/0166925 A1 | 6/2018 | Hosseini |
| 2018/0226840 A1 | 8/2018 | Leabman |
| 2018/0241255 A1 | 8/2018 | Leabman |
| 2018/0262040 A1 | 9/2018 | Contopanagos |
| 2018/0287431 A1 | 10/2018 | Liu et al. |
| 2018/0309314 A1 | 10/2018 | White et al. |
| 2018/0331581 A1* | 11/2018 | Hosseini .................... H02J 7/0042 |
| 2018/0375340 A1 | 12/2018 | Bell et al. |
| 2018/0376235 A1 | 12/2018 | Leabman |
| 2019/0052979 A1* | 2/2019 | Chen .................... H02J 50/23 |
| 2019/0074728 A1 | 3/2019 | Leabman |
| 2019/0131827 A1 | 5/2019 | Johnston |
| 2019/0173323 A1 | 6/2019 | Hosseini |
| 2019/0245389 A1 | 8/2019 | Johnston et al. |
| 2019/0288567 A1 | 9/2019 | Leabman et al. |
| 2019/0296586 A1 | 9/2019 | Moshfeghi |
| 2019/0372384 A1 | 12/2019 | Hosseini et al. |
| 2019/0393729 A1 | 12/2019 | Contopanagos et al. |
| 2019/0393928 A1 | 12/2019 | Leabman |
| 2020/0006988 A1 | 1/2020 | Leabman |
| 2020/0021128 A1 | 1/2020 | Bell et al. |
| 2020/0044488 A1 | 2/2020 | Johnston et al. |
| 2020/0112204 A1 | 4/2020 | Hosseini et al. |
| 2020/0119592 A1 | 4/2020 | Hosseini |
| 2020/0153117 A1 | 5/2020 | Papio-Toda et al. |
| 2020/0203837 A1 | 6/2020 | Komaros et al. |

FOREIGN PATENT DOCUMENTS

| | | |
|---|---|---|
| CN | 102860037 A | 1/2013 |
| CN | 103348563 A | 10/2013 |
| CN | 203826555 U | 9/2014 |
| CN | 104090265 A | 10/2014 |
| CN | 104167773 A | 11/2014 |
| CN | 104347915 A | 2/2015 |
| CN | 105765821 A | 7/2016 |
| CN | 106329116 A | 1/2017 |
| CN | 103380561 B | 9/2017 |
| DE | 200216655 U1 | 2/2002 |
| DE | 102003216953 A1 | 2/2015 |
| EP | 1028482 A2 | 8/2000 |
| EP | 1081506 A1 | 3/2001 |
| EP | 2346136 A1 | 7/2011 |
| EP | 2397973 A1 | 2/2012 |
| EP | 2545635 A2 | 1/2013 |
| EP | 2747195 A1 | 6/2014 |
| EP | 3067983 A1 | 9/2016 |
| EP | 3118970 A1 | 1/2017 |
| EP | 3145052 A1 | 3/2017 |
| GB | 2404497 A | 2/2005 |
| GB | 2556620 A | 6/2018 |
| JP | 2000323916 A | 11/2000 |
| JP | 2002319816 A | 10/2002 |
| JP | 2006157586 A | 6/2006 |
| JP | 2007043432 A | 2/2007 |
| JP | 2008167017 A | 7/2008 |
| JP | 2012016171 A | 1/2012 |
| JP | 2012095226 A | 5/2012 |
| JP | 2012157167 A | 8/2012 |
| JP | 2013162624 A | 8/2013 |
| JP | 2014075927 A | 4/2014 |
| JP | 2014112063 A | 6/2014 |
| JP | 2014176131 A | 9/2014 |
| JP | 2015027345 A | 2/2015 |
| JP | 2015128349 A | 7/2015 |
| JP | 2015128370 A | 7/2015 |
| JP | WO2015177859 A1 | 4/2017 |
| KR | 20060061776 A | 6/2006 |
| KR | 20070044302 A | 4/2007 |
| KR | 100755144 B1 | 9/2007 |
| KR | 20110132059 A | 12/2011 |
| KR | 20110135540 A1 | 12/2011 |
| KR | 20120009843 A | 2/2012 |
| KR | 20120108759 A | 10/2012 |
| KR | 20130026977 A | 3/2013 |
| KR | 20140023409 A | 2/2014 |
| KR | 20140023410 A | 3/2014 |
| KR | 20140085200 A | 7/2014 |
| KR | 20150077678 A | 7/2015 |
| WO | WO 199508125 A1 | 3/1995 |
| WO | WO 199831070 A1 | 7/1998 |
| WO | WO 199952173 A1 | 10/1999 |
| WO | WO 2000111716 A1 | 2/2001 |
| WO | WO 2003091943 A1 | 11/2003 |
| WO | WO 2004077550 A1 | 9/2004 |
| WO | WO 2006122783 A2 | 11/2006 |
| WO | WO 2007070571 A2 | 6/2007 |
| WO | WO 2008024993 A2 | 2/2008 |
| WO | WO 2008156571 A2 | 12/2008 |
| WO | WO 2010022181 A1 | 2/2010 |
| WO | WO 2010039246 A1 | 4/2010 |
| WO | WO 2010138994 A1 | 12/2010 |
| WO | WO 2011112022 A2 | 9/2011 |
| WO | WO 2012177283 A1 | 12/2012 |
| WO | WO 2013031988 A1 | 3/2013 |
| WO | WO 2013035190 A1 | 3/2013 |
| WO | WO 2013038074 A2 | 3/2013 |

(56) References Cited

FOREIGN PATENT DOCUMENTS

| WO | WO 2013042399 A1 | 3/2013 |
|----|------------------|--------|
| WO | WO 2013052950 A1 | 4/2013 |
| WO | WO 2013105920 A2 | 7/2013 |
| WO | WO 2013175596 A1 | 11/2013 |
| WO | WO 2014068992 A1 | 5/2014 |
| WO | WO 2014075103 A1 | 5/2014 |
| WO | WO 2014113093 A1 | 7/2014 |
| WO | WO 2014132258 A1 | 9/2014 |
| WO | WO 2014134996 A1 | 9/2014 |
| WO | WO 2014182788 A2 | 11/2014 |
| WO | WO 2014182788 A3 | 11/2014 |
| WO | WO 2014197472 A1 | 12/2014 |
| WO | WO 2014209587 A1 | 12/2014 |
| WO | WO 2015038773 A1 | 3/2015 |
| WO | WO 2015097809 A1 | 7/2015 |
| WO | WO 2015161323 A1 | 10/2015 |
| WO | WO 2016024869 A1 | 2/2016 |
| WO | WO 2016048512 A1 | 3/2016 |
| WO | WO 2016187357 A1 | 11/2016 |

OTHER PUBLICATIONS

Energous Corp., ISRWO, PCT/US2014/037072, Sep. 12, 2014, 8 pgs.
Energous Corp., IPRP, PCT/US2014/037072, Nov. 10, 2015, 6 pgs.
Energous Corp., ISRWO, PCT/US2014/037109, Apr. 8, 2016, 12 pgs.
Energous Corp., IPRP, PCT/US2014/037109, Apr. 12, 2016, 9 pgs.
Energous Corp., ISRWO, PCT/US2014/037170, Sep. 15, 2014, 11 pgs.
Energous Corp., IPRP, PCT/US2014/037170, Nov. 10, 2015, 8 pgs.
Energous Corp., ISRWO, PCT/US2014/040648, Oct. 10, 2014, 11 pgs.
Energous Corp., IPRP, PCT/US2014/040648, Dec. 8, 2015, 8 pgs.
Energous Corp., ISRWO, PCT/US2014/040697, Oct. 1, 2014, 12 pgs.
Energous Corp., IPRP, PCT/US2014/040697, Dec. 8, 2015, 9 pgs.
Energous Corp., ISRWO, PCT/US2014/040705, Sep. 23, 2014, 8 pgs.
Energous Corp., IPRP, PCT/US2014/040705, Dec. 8, 2015, 6 pgs.
Energous Corp., ISRWO, PCT/US2014/041323, Oct. 1, 2014, 10 pgs.
Energous Corp., IPRP, PCT/US2014/041323, Dec. 22, 2015, 8 pgs.
Energous Corp., ISRWO, PCT/US2014/041342, Jan. 27, 2015, 10 pgs.
Energous Corp., IPRP, PCT/US2014/041342, Dec. 15, 2015, 8 pgs.
Energous Corp., ISRWO, PCT/US2014/041534, Oct. 13, 2014, 10 pgs.
Energous Corp., IPRP, PCT/US2014/041534, Dec. 29, 2015, 7 pgs.
Energous Corp., ISRWO, PCT/US2014/041546, Oct. 16, 2014, 12 pgs.
Energous Corp., IPRP, PCT/US2014/041546, Dec. 29, 2015, 9 pgs.
Energous Corp., ISRWO, PCT/US2014/041558, Oct. 10, 2014, 8 pgs.
Energous Corp., IPRP, PCT/US2014/041558, Dec. 29, 2015, 6 pgs.
Energous Corp., ISRWO, PCT/US2014/044810 Oct. 21, 2014, 12 pgs.
Energous Corp., IPRP, PCT/US2014/044810, Jan. 5, 2016, 10 pgs.
Energous Corp., ISRWO, PCT/US2014/045102, Oct. 28, 2014, 14 pgs.
Energous Corp., IPRP, PCT/US2014/045102, Jan. 12, 2016, 11 pgs.
Energous Corp., ISRWO, PCT/US2014/045119, Oct. 13, 2014, 11 pgs.
Energous Corp., IPRP, PCT/US2014/045119, Jan. 12, 2016, 9 pgs.
Energous Corp., ISRWO, PCT/US2014/045237, Oct. 13, 2014, 16 pgs.
Energous Corp., IPRP, PCT/US2014/045237, Jan. 12, 2016, 12 pgs.
Energous Corp., ISRWO, PCT/US2014/046941, Nov. 6, 2014, 11 pgs.
Energous Corp., IPRP, PCT/US2014/046941, Jan. 19, 2016, 9 pgs.
Energous Corp., ISRWO, PCT/US2014/046956, Nov. 12, 2014, 10 pgs.
Energous Corp., IPRP, PCT/US2014/046956, Jan. 19, 2016, 7 pgs.
Energous Corp., ISRWO, PCT/US2014/046961, Nov. 24, 2014, 16 pgs.
Energous Corp., IPRP, PCT/US2014/046961, Jan 19, 2016, 8 pgs.
Energous Corp., ISRWO, PCT/US2014/047963, Nov. 7, 2014, 13 pgs.
Energous Corp., IPRP, PCT/US2014/047963, Jan. 26, 2016, 10 pgs.
Energous Corp., ISRWO, PCT/US2014/048002, Nov. 13, 2014, 11 pgs.
Energous Corp., IPRP, PCT/US2014/048002, Feb. 12, 2015 8 pgs.
Energous Corp., ISRWO, PCT/US2014/049666, Nov. 10, 2014, 7 pgs.
Energous Corp., IPRP, PCT/US2014/049666, Feb. 9, 2016, 5 pgs.
Energous Corp., ISRWO, PCT/US2014/049669, Nov. 13, 2014, 10 pgs.
Energous Corp., IPRP, PCT/US2014/049669, Feb. 9, 2016, 8 pgs.
Energous Corp., ISRWO, PCT/US2014/049673, Nov. 18, 2014, 10 pgs.
Energous Corp., IPRP, PCT/US2014/049673, Feb. 9, 2016, 6 pgs.
Energous Corp., ISRWO, PCT/US2014/054891, Dec. 18, 2014, 12 pgs.
Energous Corp., IPRP, PCT/US2014/054891, Mar. 15, 2016, 10 pgs.
Energous Corp., ISRWO, PCT/US2014/054897, Feb. 17, 2015, 10 pgs.
Energous Corp., IPRP, PCT/US2014/054897, Mar. 15, 2016, 8 pgs.
Energous Corp., ISRWO, PCT/US2014/054953, Dec. 4, 2014, 7 pgs.
Energous Corp., IPRP, PCT/US2014/054953, Mar. 22, 2016, 5 pgs.
Energous Corp., ISRWO, PCT/US2014/055195, Dec. 22, 2014, 11 pgs.
Energous Corp., IPRP, PCT/US2014/055195, Mar. 22, 2016, 9 pgs.
Energous Corp., ISRWO, PCT/US2014/059317, Feb. 24, 2015, 13 pgs.
Energous Corp., IPRP, PCT/US2014/059317, Apr, 12, 2016, 10 pgs.
Energous Corp., ISRWO, PCT/US2014/059340, Jan. 15, 2015, 13 pgs.
Energous Corp., IPRP, PCT/US2014/059340, Apr. 12, 2016, 11 pgs.
Energous Corp., ISRWO, PCT/US2014/059871, Jan. 23, 2015, 12 pgs.
Energous Corp., IPRP, PCT/US2014/059871, Apr. 12, 2016, 9 pgs.
Energous Corp., ISR, PCT/US2014/062661, Jan. 27, 2015, 3 pgs.
Energous Corp., Written Opinion, PCT/US2014/062661, dated Jan. 27, 2015, 9 pgs.
Energous Corp., IPRP, PCT/US2014/062661, May 3, 2016, 10 pgs.
Energous Corp., ISRWO, PCT/US2014/062672 Jan. 26, 2015, 11 pgs.
Energous Corp., IPRP, PCT/US2014/062672 May 10, 2016, 8 pgs.
Energous Corp., ISRWO, PCT/US2014/062682, Feb. 12, 2015, 10 pgs.
Energous Corp., IPRP, PCT/US2014/062682, May 3, 2016, 8 pgs.
Energous Corp., ISRWO, PCT/US2014/068282, Mar. 19, 2015, 13 pgs.
Energous Corp., IPRP, PCT/US2014/068282, Jun. 7, 2016, 10 pgs.
Energous Corp., ISRWO, PCT/US2014/068568, Mar. 20, 2015, 10 pgs.
Energous Corp., IPRP, PCT/US2014/068568, Jun. 14, 2016, 8 pgs.
Energous Corp., ISRWO, PCT/US2014/068586, Mar. 20, 2015, 11 pgs.
Energous Corp., IPRP, PCT/US2014/068586, Jun. 14, 2016, 8 pgs.
Energous Corp., ISRWO, PCT/US2015/067242, Mar. 16, 2016, 9 pgs.
Energous Corp., IPRP, PCT/US2015/067242, Jun. 27, 2017, 7 pgs.
Energous Corp., ISRWO, PCT/US2015/067243, Mar. 10, 2016, 11 pgs.
Energous Corp., IPRP, PCT/US2015/067243, Jun. 27, 2017, 7 pgs.
Energous Corp., ISRWO, PCT/US2015/067245, Mar. 17, 2016, 8 pgs.
Energous Corp., IPRP, PCT/US2015/067245, Jun. 27, 2017, 7 pgs.
Energous Corp., ISRWO, PCT/US2015/067246, May 11, 2016, 18 pgs.

(56) References Cited

OTHER PUBLICATIONS

Energous Corp., IPRP, PCT/US2015/067246, Jun. 27, 2017, 9 pgs.
Energous Corp., ISRWO, PCT/US2015/067249, Mar. 29, 2016, 8 pgs.
Energous Corp., IPRP, PCT/US2015/067249, Jun. 27, 2017, 7 pgs.
Energous Corp., ISRWO, PCT/US2015/067250, Mar. 30, 2016, 11 pgs.
Energous Corp., IPRP, PCT/US2015/067250, Mar. 30, 2016, 10 pgs.
Energous Corp., ISRWO, PCT/US2015/067271, Mar. 11, 2016, 6 pgs.
Energous Corp., IPRP, PCT/US2015/067271, Jul. 4, 2017, 5 pgs.
Energous Corp., ISRWO, PCT/US2015/067275, Mar. 3, 2016, 8 pgs.
Energous Corp., IPRP, PCT/US2015/067275, Jul. 4, 2017, 7 pgs.
Energous Corp., ISRWO, PCT/US2015/067279, Mar. 11, 2015, 13 pgs.
Energous Corp., IPRP, PCT/US2015/067279, Jul. 4, 2017, 7 pgs.
Energous Corp., ISRWO, PCT/US2015/067282, Jul. 5, 2016, 7 pgs.
Energous Corp., IPRP, PCT/US2015/067282, Jul. 4, 2017, 6 pgs.
Energous Corp., ISRWO, PCT/US2015/067287, Feb. 2, 2016, 8 pgs.
Energous Corp., IPRP, PCT/US2015/067287, Jul. 4, 2017, 6 pgs.
Energous Corp., ISRWO, PCT/US2015/067291, Mar. 4, 2016, 10 pgs.
Energous Corp., IPRP, PCT/US2015/067291, Jul. 4, 2017, 4 pgs.
Energous Corp., ISRWO, PCT/US2015/067294, Mar. 29, 2016, 7 pgs.
Energous Corp., IPRP, PCT/US2015/067294, Jul. 4, 2017, 6 pgs.
Energous Corp., ISRWO, PCT/US2015/067325, Mar. 10, 2016, 9 pgs.
Energous Corp., IPRP, PCT/US2015/067325, Jul. 4, 2017, 8 pgs.
Energous Corp., ISRWO, PCT/US2015/067334, Mar. 3, 2016, 6 pgs.
Energous Corp., IPRP, PCT/US2015/067334, Jul. 4, 2017, 5 pgs.
Energous Corp., ISRWO, PCT/US2016/068495, Mar. 30, 2017, 9 pgs.
Energous Corp., IPRP, PCT/US2016/068495, Jun. 26, 2018, 7 pgs.
Energous Corp., ISRWO, PCT/US2016/068498, May 17, 2017, 8 pgs.
Energous Corp., IPRP, PCT/US2016/068498, Jun. 26, 2018, 6 pgs.
Energous Corp., ISRWO, PCT/US2016/068504, Mar. 30, 2017, 8 pgs.
Energous Corp., IPRP, PCT/US2016/068504, Jun. 26, 2018, 5 pgs.
Energous Corp., ISRWO, PCT/US2016/068551, Mar. 17, 2017, 8 pgs.
Energous Corp., IPRP, PCT/US2016/068551, Jun. 26, 2018, 6 pgs.
Energous Corp., ISRWO, PCT/US2016/068565, Mar. 8, 2017, 11 pgs.
Energous Corp., IPRP, PCT/US2016/068565, Jun. 26, 2018, 9 pgs.
Energous Corp., ISRWO, PCT/US2016/068987, May 8, 2017, 10 pgs.
Energous Corp., IPRP, PCT/US2016/068987, Jul. 3, 2018, 7 pgs.
Energous Corp., ISRWO, PCT/US2016/068993, Mar. 13, 2017, 12 pgs.
Energous Corp., IPRP, PCT/US2016/068993, Jul. 3, 2018, 10 pgs.
Energous Corp., ISRWO, PCT/US2016/069313 Nov. 13, 2017, 10 pgs.
Energous Corp., IPRP, PCT/US2016/069313 Jul. 3, 2018, 7 pgs.
Energous Corp., ISRWO, PCT/US2016/069316 , Mar. 16, 2017, 15 pgs.
Energous Corp., IPRP, PCT/US2016/069316 , Jul. 3, 2018, 12 pgs.
Energous Corp., ISRWO, PCT/US2017/046800, Sep. 11, 2017, 13 pgs.
Energous Corp., IPRP, PCT/US2017/046800, Feb. 12, 2019, 10 pgs.
Energous Corp., ISRWO, PCT/US2017/065886, Apr. 6, 2018, 13 pgs.
Energous Corp., IPRP, PCT/US2017/065886, Jun. 18, 2019, 10 pgs.
Energous Corp., ISRWO, PCT/US2018/012806 , Mar. 23, 2018, 9 pgs.
Energous Corp., IPRP, PCT/US2018/012806 , Jul. 9, 2019, 6 pgs.
Energous Corp., ISRWO, PCT/US2018/025465, Jun. 22, 2018, 9 pgs.
Energous Corp., IPRP, PCT/US2018/025465, Oct. 1, 2019, 8 pgs.
Energous Corp., ISRWO, PCT/US2018/064289, Apr. 25, 2019, 12 pgs.
Energous Corp., ISRWO, PCT/US2018/031768, Jul. 3, 2018, 9 pgs.
Energous Corp., IPRP, PCT/US2018/031768, Nov. 12, 2019, 8 pgs.
Energous Corp., ISRWO, PCT/US2018/031786, Aug. 8, 2018, 9 pgs.
Energous Corp., IPRP, PCT/US2018/031786, Apr. 14, 2020, 7 pgs.
Energous Corp., ISRWO, PCT/US2018/039334, Sep. 11, 2018, 9 pgs.
Energous Corp., IPRP, PCT/US2018/039334, Dec. 24, 2019, 8 pgs.
Energous Corp., ISRWO, PCT/US2018/051082, Dec. 12, 2018, 9 pgs.
Energous Corp., IPRP, PCT/US2018/051082, Mar. 17, 2020, 9 pgs.
Energous Corp., ISRWO, PCT/US2018/058178, Mar. 13, 2019, 10 pgs.
Energous Corp., IPRP, PCT/US2018/058178, May 5, 2020, 7 pgs.
Energous Corp., ISRWO, PCT/US2019/015820, May 14, 2019, 9 pgs.
Energous Corp., ISRWO, PCT/US2019/021817, Apr. 6, 2019, 11 pgs.
Energous Corp., ISRWO, PCT/US2019/039014, Oct. 4, 2019, 15 pgs.
Energous Corp., ISRWO, PCT/US2019/061445, Jan. 7, 2020, 19 pgs.
Order Granting Reexamination Request Control No. 90013793 Aug. 31, 2016, 23 pgs.
*Ossia Inc.* vs *Energous Corp.*, PGR2016-00023—Institution Decision, Nov. 29, 2016, 29 pgs.
*Ossia Inc.* vs *Energous Corp.*, PGR2016-00024—Institution Decision, Nov. 29, 2016, 50 pgs.
*Ossia Inc.* vs *Energous Corp.*, PGR2016-00024—Judgement-Adverse, Jan. 20, 2017, 3 pgs.
ReExam Ordered Control No. 90013793 Feb. 2, 2017, 8 pgs.
*Ossia Inc.* vs *Energous Corp.*, Declaration of Stephen B. Heppe in Support of Petition for Post-Grant Review of U.S. Pat. No. 9,124,125, PGR2016-00024, May 31, 2016, 122 pgs.
*Ossia Inc.* vs *Energous Corp.*, Petition for Post-Grant Review—PGR2016-00023—U.S. Pat. No. 9,124,125, May 31, 2016, 92 pgs.
*Ossia Inc.* vs *Energous Corp.*, Patent Owner Preliminary Response, Sep. 8, 2016, 95 pgs.
*Ossia Inc.* vs *Energous Corp.*, Petition for Post Grant Review—PGR2016-00024—U.S. Pat. No. 9,124,125, May 31, 2016, 86 pgs.
*Ossia Inc.* vs *Energous Corp.*, Declaration of Stephen B. Heppe in Support of Petition for Post-Grant Review of U.S. Pat. No. 9,124,125, PGR2016-00023, May 31, 2016, 144 pgs.
Extended European Search Report, EP14818136.5, dated Jul. 21, 2016, 9 pgs.
Extended European Search Report, EP16189052.0, dated Feb. 10, 2017, 13 pgs.
Extended European Search Report, EP16189319.3, dated Feb. 10, 2017, 11 pgs.
Extended European Search Report, EP14822971.9, dated Feb. 10, 2017, 10 pgs.
Extended European Search Report, EP16189987.7, dated Feb. 9, 2017, 10 pgs.
Extended European Search Report, EP16196205.5, dated Apr. 7, 2017, 9 pgs.
Extended European Search Report, EP16189300.3, dated Mar. 24, 2017, 6 pgs.
Extended European Search Report, EP16189988.5, dated Mar. 13, 2017, 6 pgs.
Extended European Search Report, EP16189982.8, dated Feb. 7, 2017, 11 pgs.
Extended European Search Report, EP16189974.5, dated Mar. 13, 2017, 7 pgs.
Extended European Search Report, EP16193743.8, dated Feb. 8, 2017, 9 pgs.
Extended European Search Report, EP14868901.1, dated Jul. 17, 2017, 6 pgs.

(56) References Cited

OTHER PUBLICATIONS

Extended European Search Report, EP15876036.3, dated May 3, 2018, 9 pgs.
Extended European Search Report, EP16882597.4, dated Aug. 7, 2019, 9 pgs.
Extended European Search Report, EP15874273.4, dated May 11, 2018, 7 pgs.
Extended European Search Report, EP15876033.0, dated Jun. 13, 2018, 10 pgs.
Extended European Search Report, EP15876043.9, dated Aug. 9, 2018, 9 pgs.
Extended European Search Report, EP18204043.6, dated Feb. 14, 2019, 5 pgs.
Extended European Search Report, EP16880153.8, dated Jul. 2, 2019, 9 pgs.
Extended European Search Report, EP17840412.5, dated Jul. 15, 2019, 8 pgs.
Extended European Search Report, EP16880139.7, dated Jul. 12, 2019, 5 pgs.
Extended European Search Report, EP16880158.7, dated Jul. 15, 2019, 8 pgs.
Extended European Search Report, EP16882696.4, dated Jul. 3, 2019, 10 pgs.
Extended European Search Report, EP17882087.4, dated Sep. 17, 2019, 10 pgs.
Extended European Search Report, EP19214719.7, dated Jan. 17, 2020, 9 pgs.
Adamiuk et al. "Compact, Dual-Polarized UWB-Antanna, Embedded in a Dielectric," IEEE Transactions on Antenna and Propagation, IEEE Service Center, Piscataway, NJ, US vol. 56, No. 2, Feb. 1, 2010, 8 pgs.
Gill et al. "A System for Change Detection and Human Recognition in Voxel Space using the Microsoft Kinect Sensor," 2011 IEEE Applied Imagery Pattern Recognition Workshop. 8 pgs.
Han et al. Enhanced Computer Vision with Microsoft Kinect Sensor: A Review, IEEE Transactions on Cybernetics vol. 43, No. 5, pp. 1318-1334, Oct. 3, 2013.
Hsieh et al. "Development of a Retrodirective Wireless Microwave Power Transmission System", IEEE, 2003 pp. 393-396.
Leabman "Adaptive Band-partitioning for Interference Cancellation in Communication System," Thesis Massachusetts Institute of Technology, Feb. 1997, pp. 1-70.
Li et al. High-Efficiency Switching-Mode Charger System Design Considerations with Dynamic Power Path Management, Mar./Apr. 2012 Issue, 8 pgs.
Mao et al. "BeamStar: An Edge-Based Approach to Routing in Wireless Sensors Networks", IEEE Transactions on Mobile Computing, IEEE Service Center, Los Alamitos, CA US, vol. 6, No. 11, Nov. 1, 2007, 13 pgs.
Mascarenas et al. "Experimental Studies of Using Wireless Energy Transmission for Powering Embedded Sensor Nodes," Nov. 28, 2009, Journal of Sound and Vibration, 13 pgs.
Mishra et al. "SIW-based Slot Array Antenna and Power Management Circuit for Wireless Energy Harvesting Applications", IEEE APSURSI, Jul. 2012, 2 pgs.
Nenzi et al. "U-Helix: On-Chip Short Conical Antenna", 2013 7th European Conference on Antennas and Propagation (EUCAP), ISBN:978-1-4673-2187-7, IEEE, Apr. 8, 2013, 5 pgs.
Qing et al. "UHF Near-Field Segmented Loop Antennas with Enlarged Interrogation Zone," 2012 IEEE International Workshop on Antenna Technology (iWAT), Mar. 1, 2012, pp. 132-135, XP055572059, ISBN: 978-1-4673-0035-3.
Singh "Wireless Power Transfer Using Metamaterial Bonded Microstrip Antenna for Smart Grid WSN", Fourth International Conference on Advances in Computing and Communications (ICACC), Aug. 27-29, 2014, Abstract 1 pg.
Smolders "Broadband Microstrip Array Antennas" Institute of Electrical 1-15 and Electronics Engineers, Digest of the Antennas and Propagation Society International Symposium, Seattle, WA, Jun. 19-24, 1994, Abstract 3 pgs.
Van Veen et al., "Beamforming: A Versatile Approach to Spatial Filtering", IEEE, ASSP Magazine, Apr. 1988, pp. 4-24.
Wei et al. "Design of a Wideband Horizontally Polarized Omnidirectional Printed Loop Antenna," IEEE Antennas and Wireless Propagation Letters, vol. II, Jan. 3, 2012, 4pgs.
Zeng et al. "A Compact Fractal Loop Rectenna for RF Energy Harvesting," IEEE Antennas and Wireless Propagation Letters, vol. 16, 4 pgs.
Zhai et al. "A Practical Wireless Charging System Based on Ultra-Wideband Retro-Reflective Beamforming" 2010 IEEE Antennas and Propagation Society International Symposium, Toronto, ON 2010, 4 pgs.
Energous Corp., ISRWO, PCT/US2020/015450, May 18, 2020, 8 pgs.
Energous Corp., IPRP, PCT/US2020/015450, Jul. 27, 2021, 6 pgs.

\* cited by examiner

SYSTEMS AND METHODS FOR MINIATURIZED ANTENNA FOR WIRELESS POWER TRANSMISSIONS

RELATED APPLICATIONS

This application claims priority to U.S. Provisional Patent Application No. 62/797,808 filed Jan. 28, 2019, entitled "Systems and Methods for Miniaturized Antenna for Wireless Power Transmissions," which is hereby incorporated by reference.

TECHNICAL FIELD

The present disclosure relates generally to wireless power transmission, and more particularly, to systems and methods for receiving wireless power transmissions using miniaturized antennas.

BACKGROUND

Portable electronic devices, such as laptop computers, mobile phones, tablets, and other electronic devices, require frequent charging of a power-storing component (e.g., a battery) to operate. Many electronic devices require charging one or more times per day. Often, charging an electronic device requires manually connecting an electronic device to an outlet or other power source using a wired charging cable. In some cases, the power-storing component is removed from an electronic device and inserted into charging equipment. Such charging is time consuming, burdensome, and inefficient because it often requires users to carry around multiple charging cables and/or other charging devices, and frequently requires users to locate appropriate power sources, e.g. wall outlets, to charge their electronic devices. Additionally, conventional charging techniques potentially deprive a user of the ability to use the device while it is charging, and/or require the user to remain next to a wall outlet or other power source to which their electronic device or other charging equipment is connected. One way to address this issue is to wirelessly transmit power to an electronic device.

In addition, building a wireless charging system for consumer devices typically requires complicated, and often, expensive antenna components to receive wirelessly delivered power. Many of these consumer devices are also very small without any spare space for added antenna components. Further, due to the size of existing antennas and ever decreasing size of consumer electronic devices, the number of antennas that can be included in an array of antennas in such consumer devices is limited, which in turn limits any beamforming and power distribution properties of such an antenna array.

In tiny devices with small form factors, such as in-the-ear hearing aid device, viable solutions often lack for adequate wireless power transfer due to the physical limitations of the device. For example, radio frequency (RF) antenna receivers need to fit into such small devices. The functional wavelength of the RF antenna receiver is multitude of any physical dimension of the said small device. When the receiver devices are so tiny, properly functioning antenna is physically not doable.

Further, systems and methods used for receipt of power waves can include electrically small antennas. Electrically small antennas are sometimes defined to be of radiant length (transmission or reception wavelength/$2\pi$), which is approximately 50 mm in 915 MHz frequency. Generally, electrically small antennas are capacitive by nature with low radiation resistance, therefore not self-resonant. In order to match to a reference impedance, e.g. 50 Ohm, to get self-resonant, the electrically small antennas would need additional matching component(s), such as inductors and capacitors, that would add losses and make wireless power transfer/transmission inefficient.

As such, it would be desirable to provide a wireless charging system that addresses the above-mentioned drawbacks.

SUMMARY

There is a need for improved antenna designs that help to address the shortcomings of conventional charging systems described above. In particular, there is a need for a wireless power receiving system in small form factor receiver devices that can efficiently receive wireless power waves. The wireless power receiving systems described herein address these shortcomings with an electrically small antenna loaded with one or more other similar electrically small antennas by placing them to proximity and utilizing the same ground plane for receiving transmitted power waves. By tuning two or more antennas into resonance within the small form factor wireless power receiving system disclosed herein, the system effectively enhances the efficiency, gain and bandwidth of the wireless power receiving system.

The wireless power receiving system in this invention makes it possible to capture energy from a wireless power transmitter without using the lossy matching components in addition to the electrically small antennas.

Compared to conventional wireless receivers which rely on a tiny antenna, and additional lossy components to generate resonance, the wireless power receiving system disclosed herein effectively increases the effectiveness of the wireless charging system. For example, the wireless power receiving system can receive wireless power waves by creating heavy mutual coupling and strong self-resonance on two or more of the electrically small antennas within the small form factor receiver devices, while a conventional wireless power receiver with a tiny antenna and matching lossy components cannot otherwise receive sufficient power. The ability of receiving wireless transmitted power waves without unnecessary lossy components also increases the overall amount of power received by the wireless power receiving system. In addition, the wireless power receiving system described herein can be used in near field transmission applications.

(A1) In some embodiments, a receiver for receiving wireless power transmissions includes an antenna ground plane. The receiver also includes first and second antenna arms coupled to the antenna ground plane and configured to receive a transmitted wireless power wave. And the first and the second antenna arms are mutually coupled to one another.

(A2) In the embodiments of (A1), the first, and the second antenna arms are coupled to one another to at least −3 dB and less than 0 dB.

(A3) In the embodiments of (A1), the receiver further includes a third antenna arm connected to the antenna ground plane, and the first, the second and the third antenna arms are coupled to one another to at least −4.8 dB and less than 0 dB.

(A4) In the embodiments of (A1), the receiver further includes a third and a fourth antenna arms connected to the antenna ground plane, and the first, the second, the third, and the fourth antenna arms are coupled to one another to at least −6 dB and less than 0 dB.

(A5) In the embodiments of any of (A1-A4), the longest dimension of the first or second antenna arms are no greater than one sixth of the wavelength of the transmitted wireless power wave.

(A6) In the embodiments of any of (A1-A5), the longest dimension of the first or second antenna arms is at the radiant length relative to a frequency of the transmitted wireless power wave.

(A7) In the embodiments of any of (A1-A6), a frequency of the transmitted wireless power wave is less than 1 GHz.

(A8) In the embodiments of any of (A1-A7), the first and the second antenna arms operate at a same frequency of the transmitted wireless power wave.

(A9) In the embodiments of any of (A1-A8), the closest gap between the first and second antenna arms is less than a longest diameter of the first and second antenna arms' radiators.

(A10) In the embodiments of any of (A1-A9), the first antenna and the second antenna arms are monopole antennas.

(A11) In the embodiments of any of (A1-A10), the first antenna and the second antenna arms are PIFAs (planar inverted-F antennas).

(A12) In the embodiments of any of (A1-A11), the first antenna and the second antenna arms are the same type of antennas.

(A13) In the embodiments of any of (A1-A12), the first antenna and the second antenna arms are different types of antennas.

(A14) In the embodiments of any of (A1-A13), the antenna ground plane includes a first rectifier connected to the first antenna arm, and a second rectifier connected to the second antenna arm. And the first and the second rectifiers are configured to convert an alternating current of the transmitted wireless power wave to a direct current for providing power to a device.

(A15) In the embodiments of any of (A1-A14), the transmitted wireless power wave is a radio frequency (RF) wave.

(A16) In the embodiments of any of (A1-A15), the receiver further includes a power management integrated circuit connected to a battery and configured to regulate direct current to the battery from a rectifier connected to the power management integrated circuit.

(A17) In the embodiments of any of (A1-A16), the receiver further includes an enclosure to surround the first and second antenna arms and the ground plane.

(A18) In the embodiments of any of (A1-A17), the receiver has a maximum dimension equal or smaller than 10 millimeters.

(A19) In the embodiments of any of (A1-A18), the antenna ground plane is integrated as part an antenna board.

(A20) In the embodiments of any of (A1-A19), each of the antenna arms is disposed above, below, or on the antenna ground plane.

(A21) In the embodiments of any of (A1-A20), the receiver is configured to receive near-field wireless power transmissions.

(A22) In the embodiments of any of (A1-A21), the first and second antenna arms are substantially symmetric to one another.

(A23) In the embodiments of any of (A1-A22), the shapes of the first and second antenna arms are aligned with the enclosure of a device within which the first and second antenna arms are embedded.

(A24) In the embodiments of any of (A1-A23), the device is a hearing aid device fitted into an ear canal.

(A25) In some embodiments, a method for receiving wireless power waves, includes the following steps: providing an antenna ground plane; providing two or more antenna arms coupled to the same antenna ground plane, wherein the two or more antenna arms are close enough to have strong coupling effect at a frequency of a transmitted wireless power wave; loading the two or more antenna arms with each other to create self-resonance at the frequency of the transmitted wireless power wave, and; receiving the transmitted wireless power wave by the two or more antenna arms.

(A26) In the embodiments of (A25), the first, and the second antenna arms are coupled to one another to at least −3 dB and less than 0 dB.

(A27) In the embodiments of any of (A25-A26), the method for receiving wireless power waves, further includes the step of converting an alternating current of the transmitted wireless power wave to a direct current for providing power to a device, by rectifiers coupled to the first and the second antenna arms.

(A28) In the embodiments of any of (A25-A27), the method for receiving wireless power waves, further includes the step of storing power from the transmitted wireless power wave in a battery.

(A29) In the embodiments of any of (A25-A28), a power management integrated circuit is connected to the battery and configured to regulate the direct current to the battery from a rectifier connected to the power management integrated circuit.

(A30) In some embodiments, a wireless power receiving system comprises a receiver component for receiving near-field wireless power transmissions that includes an antenna ground plane. The receiver component also includes first and second antenna arms coupled to the antenna ground plane and configured to receive a transmitted wireless power wave. In some examples, the first and the second antenna arms are mutually coupled to one another to at least −3 dB and less than 0 dB. The wireless power receiving system also comprises a device component powered by a battery.

(A31) In the embodiments of (A30), the device component comprises a wireless earphone, a mobile phone, a laptop, or any other consumer electronic device.

(A32) In the embodiments of (A30-A31), the longest dimension of the wireless power receiving system is no greater than 10 mm.

(A33) In some embodiments, a method of fabricating a wireless power receiving system for receiving wireless power waves, includes the steps of: selecting an antenna ground plane and two or more antenna arms coupled to the same antenna ground plane, the two or more antenna arms configured to receive a transmitted wireless power wave; and positioning the two or more antenna arms close to one another to be heavily coupled to one another.

(A34) In the embodiments of (A33), the method of fabricating a wireless power receiving system further includes providing power converters to convert alternating currents from the two or more antenna arms, and the antenna ground plane to direct currents for charging a battery and/or a client device.

The compact design of the wireless power receiving system disclosed herein utilizes heavy coupling of antennas in proximity to create self-resonance, thereby improving the reception efficiency, gain and bandwith, and overall performance of the wireless power wave receiver. Furthermore, because the wireless power receiving system can receive wireless power waves without using lossy matching components, implementation of the wireless power receiving system can increase the wireless charging coverage area compared with the use of the conventional receivers.

Note that the various embodiments described above can be combined with any other embodiments described herein. The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the inventive subject matter.

BRIEF DESCRIPTION OF THE DRAWINGS

So that the present disclosure can be understood in greater detail, a more particular description may be had by reference to the features of various embodiments, some of which are illustrated in the appended drawings. The appended drawings, however, merely illustrate pertinent features of the present disclosure and are therefore not to be considered limiting, for the description may admit to other effective features.

Figure 1:
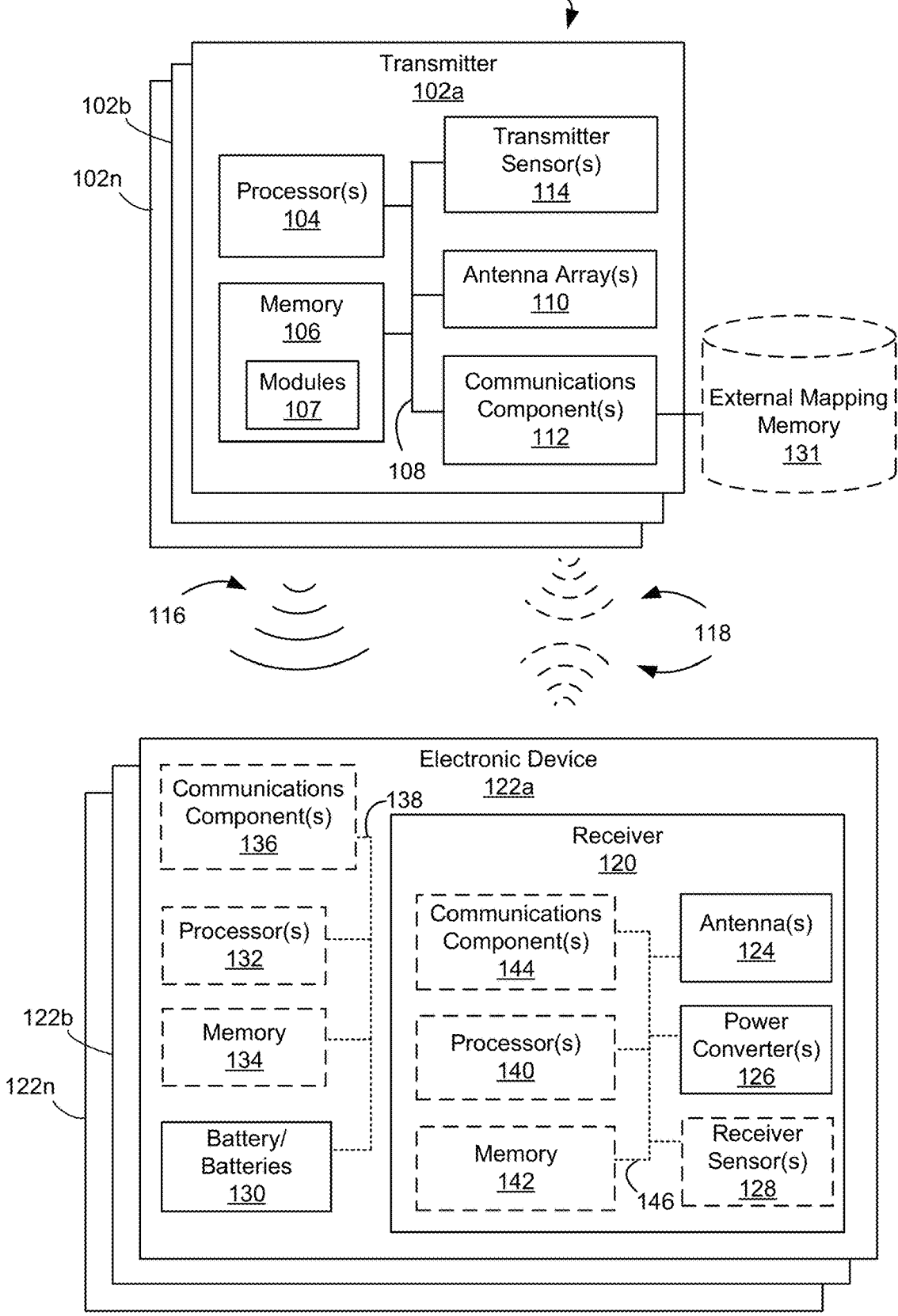
FIG. 1 is a block diagram of components of a representative wireless power transmission system or environment, in accordance with some embodiments.

In accordance with common practice, the various features illustrated in the drawings may not be drawn to scale. Accordingly, the dimensions of the various features may be arbitrarily expanded or reduced for clarity. In addition, some of the drawings may not depict all of the components of a given system, method or device. Finally, like reference numerals may be used to denote like features throughout the specification and figures.

DETAILED DESCRIPTION

Numerous details are described herein in order to provide a thorough understanding of the example embodiments illustrated in the accompanying drawings. However, some embodiments may be practiced without many of the specific details, and the scope of the claims is only limited by those features and aspects specifically recited in the claims. Furthermore, well-known processes, components, and materials have not been described in exhaustive detail so as not to unnecessarily obscure pertinent aspects of the embodiments described herein.

This invention uses highly coupled receiver antennas. In contrast, conventional wireless communications device would not use such highly coupled receiver antennas, because the concept of MIMO (multiple-input multiple-output) or diversity used in wireless communications requires good spatial isolation or de-correlation of radiation characteristics to work properly.

Mutual coupling happens when two antennas are placed very close to each other and is conventionally not desired. When two antennas are coupled, the energy received by one antenna is also absorbed by the other antenna, which reduces the amount of received energy by the first antenna simultaneously increasing the amount of received energy by the second antenna. The loss of the energy absorption as a result of a nearby coupling antenna can be quantified. In some embodiments, when half or more of the power is coupled within a multi-antenna receiver system, the coupling is strong enough to create the self-resonance described in this invention. In this invention, in some embodiments, two antennas are closely coupled or strongly coupled when the coupling is −3 dB or more and at most 0 dB. In some embodiments, three antennas are closely coupled or strongly coupled when the coupling is −4.8 dB or more and at most 0 dB. In some embodiments, four antennas are closely coupled or strongly coupled when the coupling is −6 dB or more and at most 0 dB.

The antennas in this invention are typically conventional monopoles or PIFAs (planar inverted-F antenna) that use the same electrically short ground plane. The antennas would be placed very closely to each other. In addition, because the antennas use the same tiny ground plane, they couple heavily with each other.

This feature is advantageous in wireless power transfer because this configuration increases the antenna "capturing" area of the energy. Other benefit of the mutually coupled antennas tuned to same functional frequency is that the antennas load each other creating self-resonance for both antenna radiators. This configuration removes the disadvantageous mismatch losses and further helps capturing the RF energy radiated by the transmitter antenna.

Closely coupled antennas also improve the frequency bandwidth, in theory roughly doubling the frequency bandwidth according to the below equation (1) from Ollikainen, Vainikainen "Design and Bandwidth Optimization of Dual-Resonant Patch Antennas", Espoo, March 2002 (Herein after "Ollikainen"). "It is possible to derive a simple approximate equation for the optimal relative impedance bandwidth of dual-resonant patch antennas ($B_{dr,opt}$). The optimal bandwidth depends only on the unloaded quality factors of the resonators ($Q_{01}$ and $Q_{02}$) and the maximum allowed voltage standing wave ratio (VSWR<=S). When both $Q_{01}$ and $Q_{02}$ have finite values, the optimal dual-resonant bandwidth" can be calculated from Equation (1), where S is the maximum allowed voltage standing wave ratio (VSWR):

$$B_{dr,opt} = \sqrt{S^2 - 1} \sqrt{\frac{S^2 - 1}{4S^2} \cdot \frac{1}{Q_{01}^2} + \frac{1}{Q_{01} Q_{02}} + \frac{1}{Q_{02}^2}}$$

See Ollikainen at 18.

The optimal dual-resonance depends on the unloaded quality factors of the two resonators and the VSWR criteria. This invention helps to create self-resonant electrically small antennas which otherwise would not be possible.

Various embodiments of systems and methods are described herein that addresses the shortcomings described above in conventional charging systems and with existing antenna designs. In some embodiments, a wireless power receiving system described herein is a component of a receiver of a wireless power transmission environment 100 (e.g., as described with regard to FIG. 1).

In some embodiments, one or more transmitters of a wireless power transmission environment generate power waves to form pockets of energy at target locations and adjust power wave generation based on sensed data to provide safe, reliable, and efficient wirelessly-delivered power to receivers (and devices associated therewith). In some embodiments, a controlled "pocket of energy" (e.g., a region in which available power is high due to constructive interference of power waves) and/or null spaces (e.g., a region in which available power is low or nonexistent due to destructive interference of power waves) may be formed by convergence of the power waves transmitted into a transmission field of the one or more transmitters.

In some embodiments, pockets of energy form at one or more locations in a two- or three-dimensional field due to patterns of constructive interference caused by convergences of transmitted power waves. Energy from the transmitted power waves may be harvested by one or more receivers (i.e., received and converted into usable power) at the one or more locations.

In some embodiments, the one or more receivers include a receiver system described herein that has two or more small antenna elements close to each other to create strong coupling and self-resonance, and those antenna elements are connected to the same ground plane (e.g., in reference to FIGS. 3-12). For example, the receiver system discussed herein may be integrated into consumer devices such as wireless earphones, wireless headsets or glasses, mobile phones, laptops, smart watches or other wearable devices, sound bars, televisions, media entertainment systems, light fixtures, and other consumer devices, to produce a respective receiver that remains compact, and aesthetically appealing, yet still capable of receiving power waves sufficient to charge those electronic devices.

In some embodiments, adaptive pocket-forming is performed, e.g., by adjusting power wave transmission to achieve a target power level for at least some of the power waves transmitted by the one or more transmitters. For example, a system for adaptive pocket-forming includes a sensor. In some embodiments, when the sensor detects an object, such as a sensitive object (e.g., a person, an animal, equipment sensitive to the power waves, and the like) within a predetermined distance (e.g., a distance within a range of 1-5 feet) of a pocket of energy, of one or more of the power waves, or of a transmitter, then a respective transmitter of the one or more transmitters adjusts one or more characteristics of transmitted power waves. Non-limiting examples of the one or more characteristics include: frequency, amplitude, trajectory, direction, phase, and other characteristics used by one or more antennas of the one or more transmitters to transmit the power waves. As one example, in response to receiving information indicating that transmission of power waves by a respective transmitter of the one or more transmitters should be adjusted (e.g., a sensor senses a sensitive object within a predetermined distance of a respective target location), the adaptive pocket-forming process adjusts the one or more characteristics accordingly.

In some embodiments, adjusting the one or more characteristics includes reducing a currently generated power level at a location by adjusting one or more transmitted power waves that converge at the target location. In some embodiments, reducing a currently generated power level includes transmitting a power wave that causes destructive interference with at least one other transmitted power wave. For example, a power wave is transmitted with a first phase that is shifted relative to a second phase of at least one other power wave to destructively interfere with the at least one other power wave in order to diminish or eliminate the currently generated power level at the target location.

In some embodiments, adjusting the one or more characteristics includes increasing a power level for some of the transmitted power waves to ensure that the receiver receives adequate energy sufficient to quickly charge a power-storing component of an electronic device that is associated with the receiver.

In some embodiments, an object is "tagged" (e.g., an identifier of the object is stored in memory in association with a flag) to indicate that the detected object is a sensitive object. In response to detection of a particular object within a predetermined distance of a target location, a determination is made as to whether the particular object is a sensitive object. In some embodiments, this determination includes performing a lookup in the memory to check whether the particular object has been previously tagged and is therefore known as a sensitive object. In response to determining that the particular object is a sensitive object, the one or more characteristics used to transmit the power waves may be adjusted accordingly, e.g., decreased or reduced transmission.

In some embodiments, sensing a sensitive object includes using a series of sensor readings from one or more sensors to determine motion of an object within a transmission field of the one or more transmitters. In some embodiments, sensor output from one or more sensors used to detect motion of the object approaching within a predetermined distance of a pocket of energy or of power waves used to form the pocket of energy. In response to a determination that a sensitive object is approaching (e.g., moving toward and/or within a predefined distance of a pocket of energy), the currently generated power level at the location of the pocket of energy is reduced. In some embodiments, the one or more sensors include sensors that are internal to the one or more transmitters and/or the receiver. In some embodiments, the one or more sensors include sensors that are external to the one or more transmitters and the receiver. In some embodiments, the one or more sensors include thermal imaging, optical, radar, and other types of sensors capable of detecting objects within a transmission field.

Although some embodiments herein include the use of Radio Frequency (RF)-based wave transmission technologies as a primary example, it should be appreciated that the wireless charging techniques that might be employed are not be limited to RF-based technologies and transmission techniques. Rather, it should be appreciated that additional or alternative wireless charging techniques may be utilized, including any suitable technology and technique for wirelessly transmitting energy so that a receiver is capable of converting the transmitted energy to electrical power. Such technologies or techniques may transmit various forms of wirelessly transmitted energy including the following non-limiting examples: ultrasound, microwave, resonant and inductive magnetic fields, laser light, infrared, or other forms of electromagnetic energy.

In the case of ultrasound, for example, one or more transducer elements may be disposed so as to form a transducer array that transmits ultrasound waves toward a receiving device that receives the ultrasound waves and converts them to electrical power. In the case of resonant or inductive magnetic fields, magnetic fields are created in a transmitter coil and converted by a receiver coil into electrical power. In addition, although the exemplary receiver system is shown, in some embodiments, as a single unit comprising potentially multiple components, both for RF reception of power and for other power reception methods mentioned in this paragraph, the receiver system can comprise multiple receivers that are physically spread around a room rather than being in a compact regular structure.

FIG. 1 is a block diagram of components of wireless power transmission environment 100, in accordance with some embodiments. Wireless power transmission environment 100 includes, for example, transmitters 102 (e.g., transmitters 102a, 102b . . . 102n) and one or more receivers 120. In some embodiments, each respective wireless power transmission environment 100 includes a number of receivers 120, each of which is associated with a respective electronic device 122 (e.g., electronic devices 122a, 122b . . . 122n).

An example transmitter 102 (e.g., transmitter 102a) includes, for example, one or more processor(s) 104, a memory 106, one or more antenna arrays 110, one or more communications components 112, and/or one or more transmitter sensors 114. In some embodiments, these components are interconnected by way of a communications bus 108. References to these components of transmitters 102 cover embodiments in which one or more than one of each of these components (and combinations thereof) are included.

In some embodiments, memory 106 stores one or more programs (e.g., sets of instructions) and/or data structures, collectively referred to as "modules" herein. In some embodiments, memory 106, or the non-transitory computer readable storage medium of memory 106 stores the following modules 107 (e.g., programs and/or data structures), or a subset or superset thereof:
  information received from receiver 120 (e.g., generated by receiver sensor 128 and then transmitted to the transmitter 102a);
  information received from transmitter sensor 114;
  an adaptive pocket-forming module that adjusts one or more power waves 116 transmitted by one or more transmitters 102; and/or
  a beacon transmitting module that transmits a communication signal 118 for detecting a receiver 120 (e.g., within a transmission field of the one or more transmitters 102).

The above-identified modules (e.g., data structures and/or programs including sets of instructions) need not be implemented as separate software programs, procedures, or modules, and thus various subsets of these modules may be combined or otherwise re-arranged in various embodiments. In some embodiments, memory 106 stores a subset of the modules identified above. In some embodiments, an external mapping memory 131 that is communicatively connected to communications component 112 stores one or more modules identified above. Furthermore, the memory 106 and/or external mapping memory 131 may store additional modules not described above. In some embodiments, the modules stored in memory 106, or a non-transitory computer readable storage medium of memory 106, provide instructions for implementing respective operations in the methods described below. In some embodiments, some or all of these modules may be implemented with specialized hardware circuits that subsume part or all of the module functionality. One or more of the above-identified elements may be executed by one or more of processor(s) 104. In some embodiments, one or more of the modules described with regard to memory 106 is implemented on memory 104 of a server (not shown) that is communicatively coupled to one or more transmitters 102 and/or by a memory of electronic device 122 and/or receiver 120.

In some embodiments, a single processor 104 (e.g., processor 104 of transmitter 102a) executes software modules for controlling multiple transmitters 102 (e.g., transmitters 102b . . . 102n). In some embodiments, a single transmitter 102 (e.g., transmitter 102a) includes multiple processors 104, such as one or more transmitter processors (configured to, e.g., control transmission of signals 116 by antenna array 110), one or more communications component processors (configured to, e.g., control communications transmitted by communications component 112 and/or receive communications by way of communications component 112) and/or one or more sensor processors (configured to, e.g., control operation of transmitter sensor 114 and/or receive output from transmitter sensor 114).

Receiver 120 (e.g., a receiver of electronic device 122) receives power signals 116 and/or communications 118 transmitted by transmitters 102. In some embodiments, receiver 120 includes one or more antennas 124 (e.g., antenna array including multiple antenna elements), power converter 126, receiver sensor 128 and/or other components or circuitry (e.g., processor(s) 140, memory 142, and/or communication component(s) 144). In some embodiments, these components are interconnected by way of a communications bus 146. References to these components of receiver 120 cover embodiments in which one or more than one of each of these components (and combinations thereof) are included. Receiver 120 converts energy from received signals 116 (e.g., power waves) into electrical energy to power and/or charge electronic device 122. For example, receiver 120 uses power converter 126 to convert captured energy from power waves 116 to alternating current (AC) electricity or direct current (DC) electricity usable to power and/or charge electronic device 122. Non-limiting examples of power converter 126 include rectifiers, rectifying circuits, power management integrated circuits (PMIC), voltage conditioners, among suitable circuitry and devices.

In some embodiments, receiver 120 is a standalone device that is detachably coupled to one or more electronic devices 122. For example, electronic device 122 has processor(s) 132 for controlling one or more functions of electronic device 122 and receiver 120 has processor(s) 140 for controlling one or more functions of receiver 120.

In some embodiments, receiver is a component of electronic device 122. For example, processor(s) 132 controls functions of electronic device 122 and receiver 120.

In some embodiments, electronic device 122 includes processor(s) 132, memory 134, communication component(s) 136, and/or battery/batteries 130. In some embodiments, these components are interconnected by way of a communications bus 138. In some embodiments, communications between electronic device 122 and receiver 120 occur via communications component(s) 136 and/or 144. In some embodiments, communications between electronic device 122 and receiver 120 occur via a wired connection between communications bus 138 and communications bus 146. In some embodiments, electronic device 122 and receiver 120 share a single communications bus.

In some embodiments, receiver 120 receives one or more power waves 116 directly from transmitter 102. In some embodiments, receiver 120 harvests power waves from one or more pockets of energy created by one or more power waves 116 transmitted by transmitter 102.

In some embodiments, after the power waves 116 are received and/or energy is harvested from a pocket of energy, circuitry (e.g., integrated circuits, amplifiers, rectifiers, PMICs and/or voltage conditioner) of the receiver 120 converts the energy of the power waves (e.g., radio frequency electromagnetic radiation) to usable power (i.e., electricity), which powers electronic device 122 and/or is stored to battery 130 of electronic device 122. In some embodiments, a rectifying circuit of the receiver 120 translates the electrical energy from AC to DC for use by electronic device 122. In some embodiments, a voltage conditioning circuit increases or decreases the voltage of the electrical energy as required by the electronic device 122. In some embodiments, an electrical relay conveys electrical energy from the receiver 120 to the electronic device 122.

In some embodiments, receiver 120 is a component of an electronic device 122. In some embodiments, a receiver 120 is coupled (e.g., detachably coupled) to an electronic device 122. In some embodiments, electronic device 122 is a peripheral device of receiver 120. In some embodiments, electronic device 122 obtains power from multiple transmitters 102 and/or using multiple receivers 120. In some embodiments, the wireless power transmission environment 100 includes a plurality of electronic devices 122, each having at least one respective receiver 120 that is used to harvest power waves from the transmitters 102 into usable power for charging the electronic devices 122.

In some embodiments, the one or more transmitters 102 adjust one or more characteristics (e.g., phase, gain, direction, and/or frequency) of power waves 116. For example, a transmitter 102 (e.g., transmitter 102a) selects a subset of one or more antenna elements of antenna array 110 to initiate transmission of power waves 116, cease transmission of power waves 116, and/or adjust one or more characteristics used to transmit power waves 116. In some implementations, the one or more transmitters 102 adjust power waves 116 such that trajectories of power waves 116 converge at a predetermined location within a transmission field (e.g., a location or region in space), resulting in controlled constructive or destructive interference patterns.

In some embodiments, respective antenna arrays 110 of the one or more transmitters 102 may include a set of one or more antennas configured to transmit the power waves 116 into respective transmission fields of the one or more transmitters 102. Integrated circuits (not shown) of the respective transmitter 102, such as a controller circuit and/or waveform generator, may control the behavior of the antennas. For example, based on the information received from the receiver by way of the communications signal 118, a controller circuit may determine a set of one or more characteristics or waveform characteristics (e.g., amplitude, frequency, trajectory, direction, phase, among other characteristics) used for transmitting the power waves 116 that would effectively provide power to the receiver 102 and electronic device 122. The controller circuit may also identify a subset of antennas from the antenna arrays 110 that would be effective in transmitting the power waves 116. As another example, a waveform generator circuit of the respective transmitter 102 coupled to the processor 104 may convert energy and generate the power waves 116 having the waveform characteristics identified by the controller, and then provide the power waves to the antenna arrays 110 for transmission.

In some embodiments, different subsets of antennas from the antenna arrays 110 are used to charge receivers 120 or electronic devices 122 at different locations. In some embodiments, different subsets of antennas with different frequencies from the antenna arrays 110 are used to charge receivers 120 or electronic devices 122 at different locations, e.g., each receiver 120 or electronic device 122 receives a particular frequency from a subset of antennas from the antenna arrays 110. In some embodiments, the frequencies from the different subsets of antennas are non-overlapping. In some embodiments, different subsets of antennas from the antenna arrays 110 are used to form pockets of energy around receivers 120 or electronic devices 122 at different locations.

In some embodiments, constructive interference of power waves occurs when two or more power waves 116 are in phase with one another and converge into a combined wave such that an amplitude of the combined wave is greater than amplitude of a single one of the power waves. For example, the positive and negative peaks of sinusoidal waveforms arriving at a location from multiple antennas "add together" to create larger positive and negative peaks. In some embodiments, a pocket of energy is formed at a location in a transmission field where constructive interference of power waves occurs. In some embodiments, largest dimension of the pocket of energy created by the constructive interference patterns is more than 5 millimeters (mm), more than 10 mm, more than 15 mm, more than 20 mm, more than 50 mm, more than 100 mm, more than 500 mm, more than 1000 mm, more than 2000 mm, or more than 5000 mm. In some embodiments, the largest dimension of the pocket of energy created by the constructive interference patterns for a particular transmitted frequency is more than half of a wavelength, more than one wavelength, more than 5 wavelengths, more than 10 wavelengths, more than 100 wavelengths, more than 1000 wavelengths, or more than 10000 wavelengths.

In some embodiments, destructive interference of power waves occurs when two or more power waves are out of phase and converge into a combined wave such that the amplitude of the combined wave is less than the amplitude of a single one of the power waves. For example, the power waves "cancel one another out," thereby diminishing the amount of energy concentrated at a location in the transmission field. In some embodiments, destructive interference is used to generate a negligible amount of energy or "null" at a location within the transmission field where the power waves converge. In some embodiments, the "null" space is created adjacent to the pockets of energy formed by the constructive interference patterns. In some embodiments, largest dimension of the "null" space created by the destructive interference patterns is more than 5 mm, more than 10 mm, more than 15 mm, more than 20 mm, more than 50 mm, more than 100 mm, more than 500 mm, more than 1000 mm, more than 2000 mm, or more than 5000 mm. In some embodiments, the largest dimension of the "null" space created by the destructive interference patterns for a particular transmitted frequency is more than half of a wavelength, more than one wavelength, more than 5 wavelengths, more than 10 wavelengths, more than 100 wavelengths, more than 1000 wavelengths, or more than 10000 wavelengths.

In some embodiments, the one or more transmitters 102 transmit power waves 116 that create two or more discrete transmission fields (e.g., overlapping and/or non-overlapping discrete transmission fields). In some embodiments, a first transmission field is managed by a first processor 104 of a first transmitter (e.g. transmitter 102a) and a second transmission field is managed by a second processor 104 of a second transmitter (e.g., transmitter 102b). In some embodiments, the two or more discrete transmission fields (e.g., overlapping and/or non-overlapping) are managed by the transmitter processors 104 as a single transmission field.

In some embodiments, communications component 112 transmits communication signals 118 by way of a wired and/or wireless communication connection to receiver 120. In some embodiments, communications component 112 generates communications signals 118 used for triangulation of receiver 120. In some embodiments, communication signals 118 are used to convey information between transmitter 102 and receiver 120 for adjusting one or more characteristics used to transmit the power waves 116. In some embodiments, communications signals 118 include information related to status, efficiency, user data, power consumption, billing, geo-location, relative location, and other types of information.

In some embodiments, receiver 120 includes a transmitter (not shown), or is a part of a transceiver, that transmits communications signals 118 to communications component 112 of transmitter 102.

In some embodiments, communications component 112 (e.g., communications component 112 of transmitter 102a) includes a communications component antenna for communicating with receiver 120 and/or other transmitters 102 (e.g., transmitters 102b through 102n). In some embodiments, these communications signals 118 represent a distinct channel of signals transmitted by transmitter 102, independent from a channel of signals used for transmission of the power waves 116.

In some embodiments, the receiver 120 includes a receiver-side communications component 144 configured to communicate various types of data with one or more of the transmitters 102, through a respective communications signal 118 generated by the receiver-side communications component. The data may include location indicators for the receiver 102 and/or electronic device 122, a power status of the device 122, status information for the receiver 102, status information for the electronic device 122, status information about the power waves 116, and/or status information for pockets of energy. In other words, the receiver 102 may provide data to the transmitter 102, by way of the communications signal 118, regarding the current operation of the system 100, including: information identifying a present location of the receiver 102 or the device 122, an amount of energy received by the receiver 120, and an amount of power received and/or used by the electronic device 122, among other possible data points containing other types of information.

In some embodiments, the data contained within communications signals 118 is used by electronic device 122, receiver 120, and/or transmitters 102 for determining adjustments of the one or more characteristics used by the antenna array 110 to transmit the power waves 116. Using a communications signal 118, the transmitter 102 communicates data that is used, e.g., to identify receivers 120 within a transmission field, identify electronic devices 122, determine safe and effective waveform characteristics for power waves, and/or hone the placement of pockets of energy. In some embodiments, receiver 120 uses a communications signal 118 to communicate data for, e.g., alerting transmitters 102 that the receiver 120 has entered or is about to enter a transmission field, provide information about electronic device 122, provide user information that corresponds to electronic device 122, indicate the effectiveness of received power waves 116, and/or provide updated characteristics or transmission parameters that the one or more transmitters 102 use to adjust transmission of the power waves 116.

As an example, the communications component 112 of the transmitter 102 communicates (e.g., transmits and/or receives) one or more types of data (including, e.g., authentication data and/or transmission parameters) including various information such as a beacon message, a transmitter identifier, a device identifier for an electronic device 122, a user identifier, a charge level for electronic device 122, a location of receiver 120 in a transmission field, and/or a location of electronic device 122 in a transmission field.

In some embodiments, transmitter sensor 114 and/or receiver sensor 128 detect and/or identify conditions of electronic device 122, receiver 120, transmitter 102, and/or a transmission field. In some embodiments, data generated by transmitter sensor 114 and/or receiver sensor 128 is used by transmitter 102 to determine appropriate adjustments to the one or more characteristics used to transmit the power waves 106. Data from transmitter sensor 114 and/or receiver sensor 128 received by transmitter 102 includes, e.g., raw sensor data and/or sensor data processed by a processor 104, such as a sensor processor. Processed sensor data includes, e.g., determinations based upon sensor data output. In some embodiments, sensor data received from sensors that are external to the receiver 120 and the transmitters 102 is also used (such as thermal imaging data, information from optical sensors, and others).

In some embodiments, receiver sensor 128 is a gyroscope that provides raw data such as orientation data (e.g., tri-axial orientation data), and processing this raw data may include determining a location of receiver 120 and/or or a location of receiver antenna 124 using the orientation data.

In some embodiments, receiver sensor 128 includes one or more infrared sensors (e.g., that output thermal imaging information), and processing this infrared sensor data includes identifying a person (e.g., indicating presence of the person and/or indicating an identification of the person) or other sensitive object based upon the thermal imaging information.

In some embodiments, receiver sensor 128 includes a gyroscope and/or an accelerometer that indicates an orientation of receiver 120 and/or electronic device 122. As one example, transmitters 102 receive orientation information from receiver sensor 128 and the transmitters 102 (or a component thereof, such as the processor 104) use the received orientation information to determine whether electronic device 122 is flat on a table, in motion, and/or in use (e.g., next to a user's head).

In some embodiments, receiver sensor 128 is a sensor of electronic device 122 (e.g., an electronic device 122 that is remote from receiver 102). In some embodiments, receiver 120 and/or electronic device 122 includes a communication system for transmitting signals (e.g., sensor signals output by receiver sensor 128) to transmitter 102.

Non-limiting examples of transmitter sensor 114 and/or receiver sensor 128 include, e.g., infrared, pyroelectric, ultrasonic, laser, optical, Doppler, gyro, accelerometer, microwave, millimeter, RF standing-wave sensors, resonant LC sensors, capacitive sensors, and/or inductive sensors. In some embodiments, technologies for transmitter sensor 114 and/or receiver sensor 128 include binary sensors that acquire stereoscopic sensor data, such as the location of a human or other sensitive object.

In some embodiments, transmitter sensor 114 and/or receiver sensor 128 is configured for human recognition (e.g., capable of distinguishing between a person and other objects, such as furniture). Examples of sensor data output by human recognition-enabled sensors include: body temperature data, infrared range-finder data, motion data, activity recognition data, silhouette detection and recognition data, gesture data, heart rate data, portable devices data, and wearable device data (e.g., biometric readings and output, accelerometer data).

In some embodiments, transmitters 102 adjust one or more characteristics used to transmit the power waves 116 to ensure compliance with electromagnetic field (EMF) exposure protection standards for human subjects. Maximum exposure limits are defined by US and European standards in terms of power density limits and electric field limits (as well as magnetic field limits). These include, for example, limits established by the Federal Communications Commission (FCC) for maximum permissible exposure (MPE), and limits established by European regulators for radiation exposure. Limits established by the FCC for MPE are codified at 47 CFR § 1.1310. For electromagnetic field (EMF) frequencies in the microwave range, power density can be used to express an intensity of exposure. Power density is defined as power per unit area. For example, power density can be commonly expressed in terms of watts per square meter ($W/m^2$), milliwatts per square centimeter ($mW/cm^2$), or microwatts per square centimeter ($\mu W/cm^2$). In some embodiments, output from transmitter sensor 114 and/or receiver sensor 128 is used by transmitter 102 to detect whether a person or other sensitive object enters a power transmission region (e.g., a location within a predetermined distance of a transmitter 102, power waves generated by transmitter 102, and/or a pocket of energy). In some embodiments, in response to detecting that a person or other sensitive object has entered the power transmission region, the transmitter 102 adjusts one or more power waves 116 (e.g., by ceasing power wave transmission, reducing power wave transmission, and/or adjusting the one or more characteristics of the power waves). In some embodiments, in response to detecting that a person or other sensitive object has entered the power transmission region, the transmitter 102 activates an alarm (e.g., by transmitting a signal to a loudspeaker that is a component of transmitter 102 or to an alarm device that is remote from transmitter 102). In some embodiments, in response to detecting that a person or other sensitive object has entered a power transmission region, the transmitter 102 transmits a digital message to a system log or administrative computing device.

In some embodiments, antenna array 110 includes multiple antenna elements (e.g., configurable "tiles") collectively forming an antenna array. Antenna array 110 generates power transmission signals, e.g., RF power waves, ultrasonic power waves, infrared power waves, and/or magnetic resonance power waves. In some embodiments, the antennas of an antenna array 110 (e.g., of a single transmitter, such as transmitter 102a, and/or of multiple transmitters, such as transmitters 102a, 102b, . . . , 102n) transmit two or more power waves that intersect at a defined location (e.g., a location corresponding to a detected location of a receiver 120), thereby forming a pocket of energy (e.g., a concentration of energy) at the defined location.

In some embodiments, transmitter 102 assigns a first task to a first subset of antenna elements of antenna array 110, a second task to a second subset of antenna elements of antenna array 110, and so on, such that the constituent antennas of antenna array 110 perform different tasks (e.g., determining locations of previously undetected receivers 120 and/or transmitting power waves 116 to one or more receivers 120). As one example, in an antenna array 110 with ten antennas, nine antennas transmit power waves 116 that form a pocket of energy and the tenth antenna operates in conjunction with communications component 112 to identify new receivers in the transmission field. In another example, an antenna array 110 having ten antenna elements is split into two groups of five antenna elements, each of which transmits power waves 116 to two different receivers 120 in the transmission field.

Figure 2:
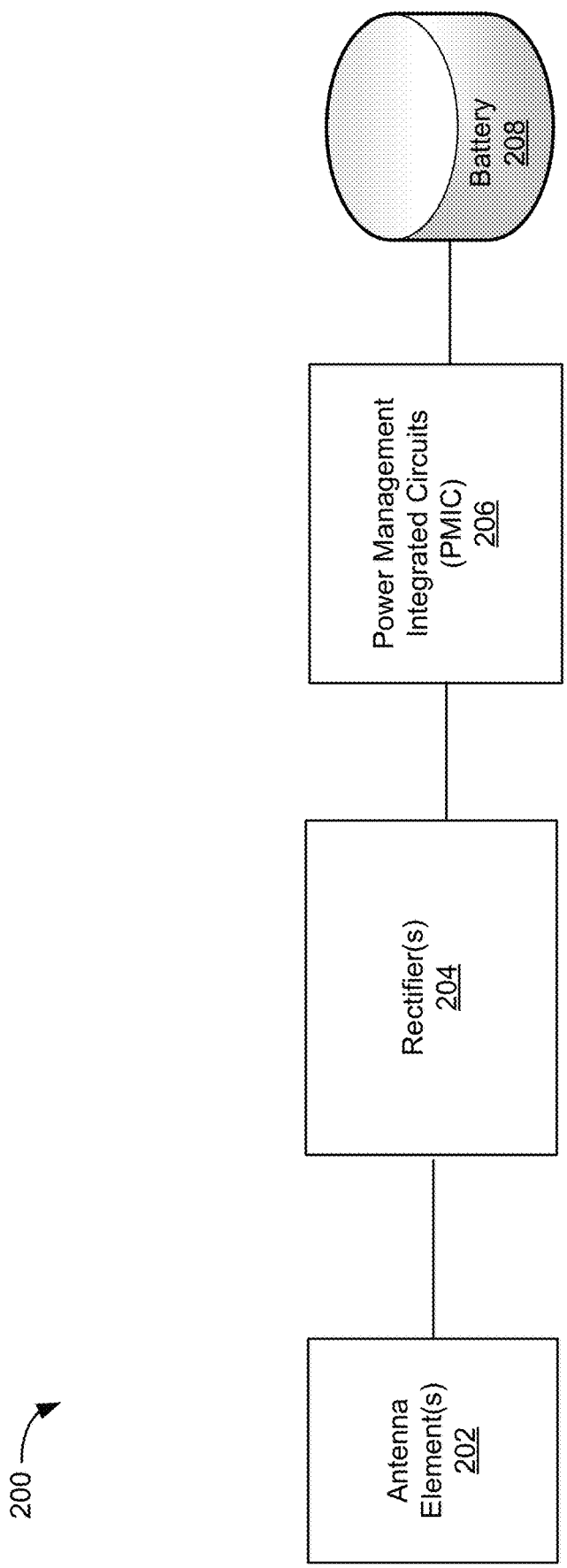
FIG. 2 is a block diagram of an exemplary wireless power receiving system 200, in accordance with some embodiments.

FIG. 2 is a block diagram of an exemplary wireless power receiving system 200, in accordance with some embodiments. In various embodiments, one or more sets of antenna elements 202 connect with their respective rectifiers 204. There can be multiple rectifiers 204 connected to their respective set of antenna elements 202. For example, in different embodiments, two, three, four, eight, or sixteen antenna elements or any other numbers are coupled with one rectifier 204. The antenna elements 202 extract or harvest power wirelessly from the wireless power waves transmitted by one or more wireless power transmitters. The antenna element(s) 202 include(s) antenna arm(s) and antenna ground plane(s), described below in relation to FIGS. 3-12.

The antenna elements 202 comprise any type of antenna capable of transmitting and/or receiving signals in frequency bands used by the transmitter. Furthermore, the antenna element 202 may be directional and/or omni-directional and include flat antenna elements, patch antenna elements, dipole antenna elements, and/or any other suitable antenna for wireless power transmission. The antenna elements 202 may be monopole antennas or inverted-F antennas (IFAs). Suitable antenna types may include, for example, monopoles or IFAs with less than 50 mm aperture size when the transmission power wave frequency is around 915 MHz. Other suitable antenna types may include, for example, patch antennas with heights from about ⅛ inch to about 6 inches and widths from about ⅛ inch to about 6 inches. The shape and orientation of antenna element 202 may vary in dependency of the desired features of receiver system 200; orientation may be flat in X, Y, and/or Z axis, as well as various orientation types and combinations in three dimensional arrangements. Antenna element 202 may be made from any suitable material that allows RF signal transmission with high efficiency, good heat dissipation and the like. The amount of antenna elements 202 may vary in relation with the desired range and power transmission capability of the transmitter; the more antenna elements, the wider the range and the higher the power transmission capability.

Antenna element 202 may include suitable antenna types for operating in frequency bands such as 900 MHz, 2.5 GHz or 5.8 GHz as these frequency bands conform to Federal Communications Commission (FCC) regulations part 18 (industrial, scientific, and medical equipment). Antenna element 202 may operate in independent frequencies, allowing a multichannel operation of pocket-forming.

In addition, antenna element 202 may have at least one polarization or a selection of polarizations. Such polarizations may include vertical, horizontal, circularly, left-hand, right-hand, or a combination of polarizations. The selection of polarizations may vary in dependency of transmitter and receiver characteristics.

In addition, antenna element 202 may be located in various surfaces of receiver 200. Antenna element 202 may operate in single array, pair array, quad array and any other suitable arrangement that may be designed in accordance with the desired application.

In some implementations, the entire side of a printed circuit board PCB or a RF integrated circuit (IC) may be closely packed with antenna element 202. The RFIC may connect to multiple antenna elements. Multiple antenna elements 202 may surround a single RFIC.

Rectifiers 204 of the receiver system 200 may include diodes, resistors, inductors, and/or capacitors to rectify alternating current (AC) voltage generated by antenna elements 204 to direct current (DC) voltage. Rectifiers 204 may be placed as close as is technically possible to antenna elements 204 to minimize losses in electrical energy gathered from power transmission signals. After rectifying AC voltage, the resulting DC voltage may be regulated using power converters (not shown). Power converters can be a DC-to-DC converter that may help provide a constant voltage output, regardless of input, to an electronic device, or as in this exemplary system 200, to a battery 208. Typical voltage outputs can be from about 5 volts to about 10 volts. In some embodiments, power converter may include electronic switched mode DC-DC converters, which can provide high efficiency. In such embodiments, the receiver 200 may comprise a capacitor (not shown) that is situated to receive the electrical energy before power converters. The capacitor may ensure sufficient current is provided to an electronic switching device (e.g., switch mode DC-DC converter), so it may operate effectively. When charging an electronic device, for example a phone or laptop computer, initial high-currents that can exceed the minimum voltage needed to activate operation of an electronic switched mode DC-DC converter, may be required. In such a case, a capacitor (not shown) may be added at the output of receivers 200 to provide the extra energy required. Afterwards, lower power can be provided. For example, 1/80 of the total initial power that may be used while having the phone or laptop still build-up charge.

The current from the rectifiers 204 is provided to a Power Management Integrated Circuit (PMIC) 206. A PMIC 206 is an integrated circuit and/or a system block in a system-on-a-chip device for managing power requirements of the host system. The PMIC 206 may include battery management, voltage regulation, and charging functions. It may include a DC-to-DC converter to allow dynamic voltage scaling. In some implementations, the PMIC 206 may provide up to a 95% power conversion efficiency. In some implementations, the PMIC 206 may integrate with dynamic frequency scaling in a combination. The PMIC 206 may be implemented in a battery-operated device such as mobile phones and/or portable media players. In some implementations, the battery 208 may be replaced with an input capacitor and an output capacitor. The PMIC 206 may be directly connected to the battery 208 and/or capacitors. When the battery 208 is being charged directly, a capacitor may not be implemented. In some implementations, the PMIC 206 may be coiled around the battery 208. The PMIC 206 may comprise a power management chip (PMC) that acts as a battery charger, and is connected to the battery 208. The PMIC 206 can use pulse-frequency modulation (PFM) and pulse-width modulation (PWM). It can use switching amplifier (Class-D electronic amplifier). In some implementations, an output converter, a rectifier, and/or a BLE may also be included in the PMIC 206.

Figure 3:
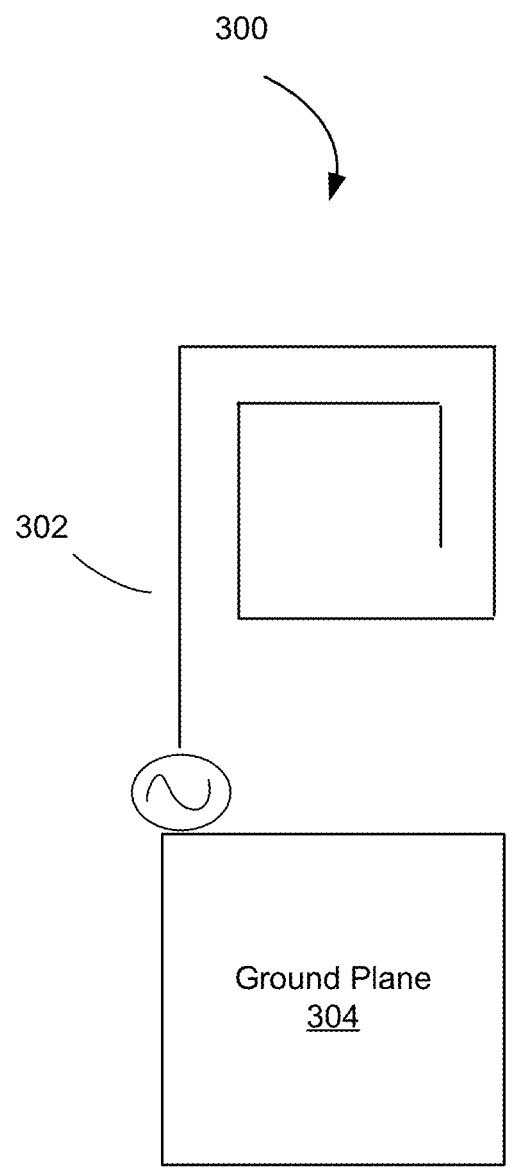
FIG. 3 is an exemplary electrically small antenna or wireless power receiving system 300 with no self-resonance.

FIG. 3 is an exemplary electrically small antenna or wireless power receiving system 300 with no self-resonance. In the wireless power receiving system 300, only one antenna radiator (arm) 302 is attached to a ground plane 304. The total length D of the antenna radiator 302 and the ground plane 304 is very small compared with the transmission or reception wavelength λ, normally D<<λ. The antenna radiator 202 can be monopoles or other antenna types as described above. Electrically small antennas are defined in literature to be of radiant length (λ/2 π), which is, for example, approximately 19 mm in 2.5 GHz frequency, approximately 24 mm in 2 GHz frequency, approximately 32 mm in 1.5 GHz frequency, approximately 48 mm in 1 GHz frequency, approximately 95 mm in 500 MHz frequency, approximately 159 mm in 300 MHz frequency, and approximately 477 mm in 100 MHz frequency. Electrically small antennas are capacitive by nature with low radiation resistance, therefore not self-resonant. In order to get self-resonant, matching components, such as capacitors and/or inductors need to be added to the electrically small antenna system 300 to match to a reference impedance, e.g. 50 Ohm. However, such matching components would add losses and result in power transmission deterioration or losses.

Figure 4:
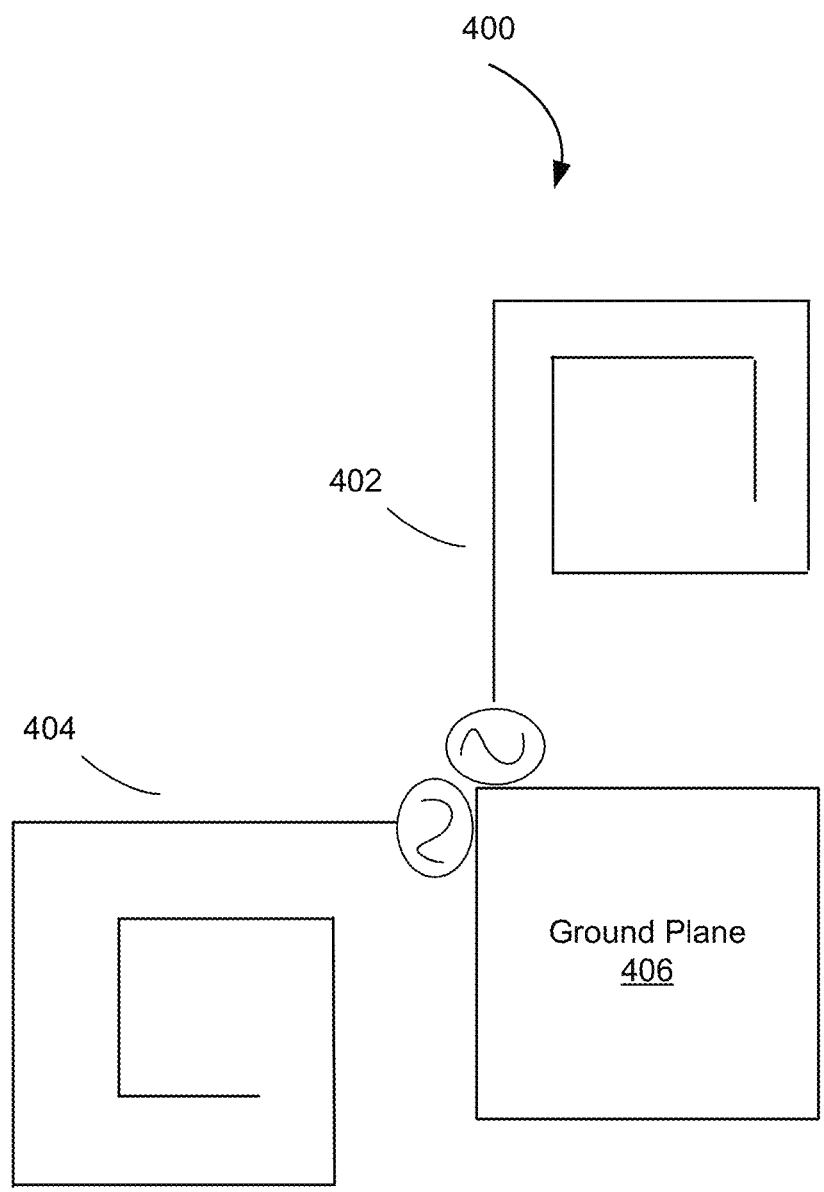
FIG. 4 shows an electrically small antenna or wireless power receiving system 400 with two antenna radiators (arms) 402 and 404 attached to a ground plane 406, in accordance with some embodiments.

FIG. 4 is an exemplary electrically small antenna or wireless power receiving system 400 with two antenna radiators (arms) 402 and 404 attached to a ground plane 406, in accordance with some embodiments. In some embodiments, the two antenna arms 402 and 404 utilizing the same ground plane are in proximity to each other to create a heavy mutual coupling, so that both antenna arms 402 and 404 have self-resonance. The length D1 of the antenna radiator 402, the length D2 of the antenna radiator 404, and the length D3 of the ground plane 406, are all very small compared with the transmission or reception wavelength λ, normally D1<<λ, D2<<λ, and D3<<λ. The antenna radiator 402 and 404 can be monopoles, IFA antennas or other antenna types as described above. In some embodiments, the antenna arms can be spiral monopole antennas. In some embodiments, the antenna types for the two antenna arms 402 and 404 are the same. In some embodiments, the antenna types implemented for the two antenna arms 402 and 404 are different. Electrically small antennas are defined in literature to be of radiant length (λ/2 π), which is approximately 50 mm in 915 MHz frequency.

When the electrically small antennas are close enough to each other, radiator open ends being at the distance of less than 50% of the radiators' longest diameter from each other, the strong coupling between the antennas can create self-resonance to both antennas utilizing the same ground plane. Matching components, such as capacitors and/or inductors that are traditionally added to the electrically small antenna system to create a matching reference impedance can be eliminated or greatly reduced. Therefore, electronic power transmission gain can be improved by eliminating losses traditionally introduced by those lossy matching components. The electrically small antenna arm 402 in wireless power receiving system 400 is loaded with other similar electrically small antenna arms, such as antenna arm 404. In some examples, antenna arms are similar when their electrical lengths are similar. Or in other words, the antennas have similar resonant frequency, for example, the resistive component of the input impedances of the two antennas are within 20% from each other in said resonant frequency. The antenna arms 402 and 404 are close to each other. This arrangement tunes both antenna arms 402 and 404 into resonance. Thus the antenna arms 402 and 404 can capture energy from a wireless power transmitter without additional lossy matching components.

In some embodiments, a wireless power receiving system includes two or more antenna arms utilizing the same ground plane and strongly coupled to one another as described above in FIG. 4. The two or more antenna arms are placed in proximity to each other to be mutually coupled to each other. Therefore, self-resonance can be created on each of the two or more antenna arms to receive power transferred from a wireless power transmitter.

In some examples, the two or more antenna arms can be similar types of antennas or different types of antennas. In some embodiments, the two or more antenna arms have similar physical and/or electronic characteristics, for example, similar size, similar capacitance, conductance, and resistance.

In some embodiments, the wireless power receiving system 400 includes two or more antenna arms adjacent to one another. In some embodiments, the two or more antenna arms are positioned on different sides of the antenna ground plane 406. In some embodiments, the wireless power receiving system 400 includes two antenna arms on the top and bottom sides respectively of the wireless power receiving system 400. In some embodiments, the antenna arms are parallel to one another. In some embodiments, depending on the shape and space of the device container enclosing the antennas, the antenna arms can be positioned at any angle to one another. In some embodiments, at least two of antenna arms are perpendicular to one another. In some embodiments, the two or more antenna arms are generally planar. In some embodiments, the two or more antenna arms have a circular shape. Circular shape can maximize the volume between the two or more antenna arms and improve the reception efficiency. And the circular shape also matches the shapes of most of the small devices such as earphones in which the antenna arms and the ground plane are embedded. In some embodiments, the two or more antenna arms have shapes such as oval, square, rectangle, triangle, and other regular or irregular shapes. In some embodiments, the shapes of the two or more antenna arms are symmetrical to one another. In some embodiments, the positions of the two or more antenna arms are symmetrical to one another. Symmetrical shapes and/or positions of the two or more antenna arms can allow even and predictable reception of the wireless power when the wireless power receiving system 400 is flipped over or turned around. In some embodiments, the shapes of the two or more antenna arms are asymmetrical to one another. In some embodiments, the positions of the two or more antenna arms are asymmetrical to one another. Asymmetrical shapes and/or positions of the two or more antenna arms can fit into the need of specific applications of wireless power reception pertaining to a particular client device's shape and function.

In some embodiments, the antenna ground plane 406 includes printed circuit boards (PCBs). In some embodiments, the ground plane 406 includes one or more rectifiers and/or one or more PMICs, and/or other power regulating circuits.

In some embodiments, a frequency at which the antenna arms receive electromagnetic waves varies based on the size of the antenna arms.

In some embodiments, the antenna arms have dimensions of $\lambda/4$ or smaller, where $\lambda$ is a wavelength that corresponds to a frequency of electromagnetic waves that the antenna arms are configured to receive. In some embodiments, the antenna arms have dimensions of $\lambda/2\pi$ or smaller, In some embodiments, the wireless power receiving system 400 is at a size that can fit into a small size electronic device such as a pacemaker or an earphone. For example, in some embodiments, the size or largest dimension of the wireless power receiving system 400 is at about 10 millimeter (mm). In some embodiments, the size or largest dimension of the wireless power receiving system 400 is smaller than 10 mm. In some embodiments, the size or largest dimension of the wireless power receiving system 400 is at or smaller than 5 mm. In some embodiments, the wireless power receiving system 400 is at a size that can fit into a compact electronic device such as a mobile phone or a remote controller. For example, in some embodiments, the size or largest dimension of the wireless power receiving system 400 is at or smaller than 20 mm. In some embodiments, the size or largest dimension of the wireless power receiving system 400 is at or smaller than 30 mm. In some embodiments, the size or largest dimension of the wireless power receiving system 400 is at or smaller than 40 mm. In some embodiments, the size or largest dimension of the wireless power receiving system 400 is at or smaller than 50 mm. In some embodiments, the wireless power receiving system 400 is at a size that can fit into an electronic device such as a remote key board, a sound bar or a TV. For example, in some embodiments, the size or largest dimension of the wireless power receiving system 400 is at or smaller than 100 mm.

As will be apparent to one of skill in the art, the various features and configurations of each of the antenna arms may be combined or substituted in various ways to produce a variety of additional embodiments, and may also include different types of feed elements, including a dipole element, patch array feed element, and/or split ring feed element. In some embodiments, an array of antenna arms may include different types and/or configurations of individual antenna arms. For example, an array of antenna arms includes individual antenna arms arranged in a linear configuration, a planar configuration, or a non-planar (e.g., cylindrical array) configuration. For example, a linear configuration and a planar configuration of the antenna arms can be used to improve gain when the space within the wireless power receiving system 400 is limited. A non-planar antenna arm (e.g., a rectangularly coiled antenna arm) is used when further enhancement of the reception of wireless wave from different directions is needed.

In some embodiments, the antenna ground plane 406 connects with an antenna board (not shown in FIG. 4) through connections. An antenna ground plane 406 is an electrically conductive surface large in comparison to the wavelength of the transmitted wireless waves which is usually connected to an electrical ground. In some embodiments, an antenna ground plane 406 is a large area of conductive surface on a PCB board. The antenna ground plane 406 is connected to the ground terminal of a power supply and serves as a return path for current from antenna arms such as 402 and 404 and different circuit components on the PCB board. In some embodiments, the largest dimension of the antenna ground plane 406 is at least a half the wavelength of the transmitted wireless wave. In some embodiments, the largest dimension of the antenna ground plane 406 is at least twice the length of the largest dimension of each of the antenna arms 402 and 404.

In some embodiments, the antenna ground plane 406 is substantially planar. In some embodiments, the antenna ground plane 406 is positioned adjacent to the antenna board. In some embodiments, the antenna ground plane 406 is positioned below, above or within the antenna board. In some embodiments, the antenna ground plane 406 is a part of the antenna board. In some embodiments, the antenna ground plane 406 is parallel to the antenna board. In some embodiments, the area of the antenna ground plane is more than a quarter of the antenna board. In some embodiments, the area of the antenna ground plane is less than a quarter of the antenna board. In some embodiments, the shape of the antenna ground plane 406 is any planar shape. In some embodiments, the shape of the antenna ground plane 406 is symmetrical in space.

Various design aspects of the wireless power receiving system 400, such as the dimensions of the antenna board (e.g., cross-sectional area and height of the antenna board), the dimension of the antenna ground plane 406 (e.g., cross-sectional area and height of the antenna ground plane 406), size, shape, spacing, and arrangement of the two or more antenna arms such as 402 and 404, impedance and operating frequency of the antenna arms, and the configuration between the antenna ground plane 406 and antenna arms, size and arrangement of the rectifier are selected (e.g., optimized using a cost or performance function) for obtaining desired wireless wave receiving characteristics. Wireless wave receiving characteristics that vary based on the above design aspects include, e.g., size, volume, materials, weight, cost, fabrication efficiency, radiation efficiency, impedance, and/or frequency range (for transmission and/or reception of electromagnetic waves and other wireless waves by the antenna).

In some embodiments, the wireless power transmission system 400 can operate in the sub-Giga Hz frequency ranges for receiving wireless transmission waves. In some embodiments, the wireless power transmission system 400 mainly operate in the near field ranges for receiving wireless transmission waves. In some embodiments, the wireless power transmission system 400 can operate in the middle field and far field ranges for receiving wireless transmission waves for a particular operating frequency or frequency range. In some embodiments, the wireless power transmission system 300 can operate in the near field, middle field or far field ranges for receiving wireless transmission waves for different frequency ranges. Depending on the frequencies of the transmitted wireless waves, generally, near field refers to the distance that is about less than one wavelength from the transmitting source, far field refers to the distance that is about equal or greater than two wavelengths from the transmitting source, and middle field refers to the distance that is between near field and far field.

In some embodiments, the substantially symmetrical structure of the wireless power receiving system 400, can improve the reception of the system 400. For example, especially in near field reception, when one side of the wireless power receiving system 400 is relatively far from the transmission waves or fields, the side that is closer to the source of the transmission waves or fields will get better reception. A user can flip the device with the receiving system 400 upside down without impacting its performance.

In some embodiments, the compact and circular design of the wireless power receiving system 400 disclosed herein fully utilizes the antenna volume between the two or more antenna arms and the antenna plane ground 406, thereby improving the reception efficiency, gain and bandwidth, and overall performance of the power wave receiver. Furthermore, without additional matching components to introduce losses, implementation of the system 400 can increase the wireless charging coverage area compared with the use of the conventional receivers.

Figure 5:
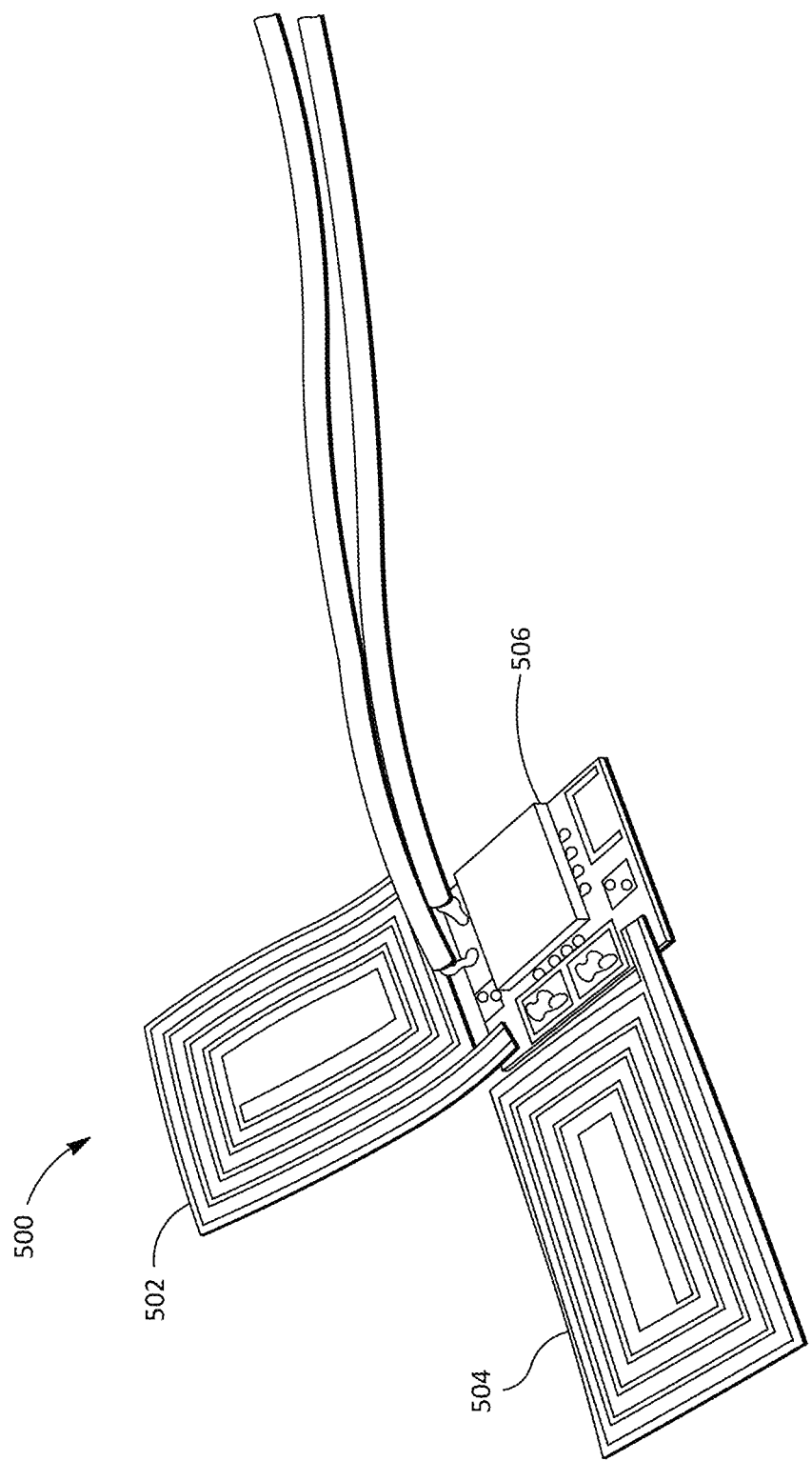
FIG. 5 shows a top-side view of a representative wireless power receiving system 500 with two spiral monopole antenna arms 502 and 504 in proximity to each other, in accordance with some embodiments.

FIG. 5 shows a top-side view of a representative wireless power receiving system 500 with the structures as disclosed in FIG. 4, in accordance with some embodiments. In some embodiments, two or more electrically small monopole or IFA antennas, for example, antenna arms 502 and 504 may be used to couple with each other. Each of the antenna arms 502 and 504 has its own input to a rectifier which converts the RF energy to DC power. For example, the antenna arm 502 connects to a rectifier.

FIG. 5 illustrates an example of using two spiral monopole antenna arms 502 and 504 in proximity to each other. In some embodiments, the two antenna arms 502 and 504 utilize same ground plane 506, i.e. PCB, and have separate RF input ports 508 (not identified in FIGS. 5) and 510 (not identified in FIG. 5) to the rectifier 512 (not identified in FIG. 5).

Figure 6:
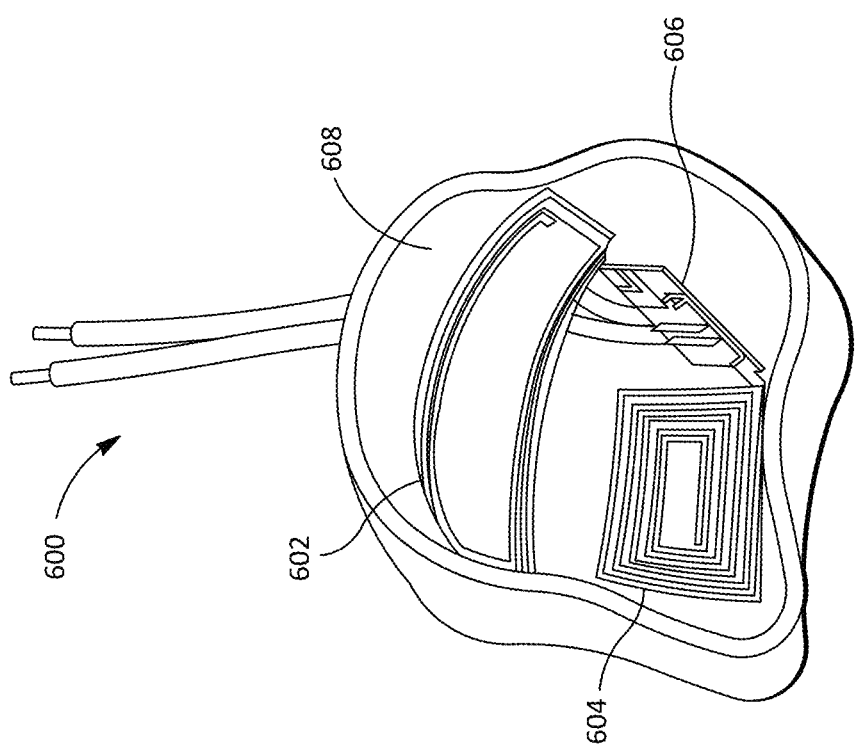
FIG. 6 shows an example of a hearing device 600 containing electrically small mutually coupled antennas 602 and 604, in accordance with some embodiments.

FIG. 6 shows an example of a hearing device 600 containing electrically small mutually coupled antennas 602 and 604, in accordance with some embodiments. Many devices have small physical dimensions, such as less than 1 centimeter (cm), 1-3 cm, or 2-5 cm. Hearing aid devices are around or smaller than 1 cm because they need to be put in a person's ear canals. Two heavily coupled receiver antenna arms 602 and 604 with the structures described in FIGS. 4 and 5 are placed into the physically small devices such as the hearing device 600 with a transparent enclosure 608. The antenna arms 602 and 604 are connected to the same ground plane 606. In one embodiment as illustrated in FIG. 6, in order to accommodate the asymmetric shape of the hearing device 600, the two antenna arms 602 and 604 can be antennas of different sizes and shapes, for example, 602 has a semi-circular size with a larger area than 604, and 604 has a rectangular size. In another embodiment, the two antenna arms 602 and 604 can be antennas of different types. By creating self-resonance to both antenna arms 602 and 604 through the heavy mutual coupling between the antenna arms 602 and 604, the hearing device can be wirelessly powered efficiently without additional matching lossy components. For devices with size restrictions, any additional components for the power receiver would compromise the limited space requirement within the enclosure 608.

Figure 7:
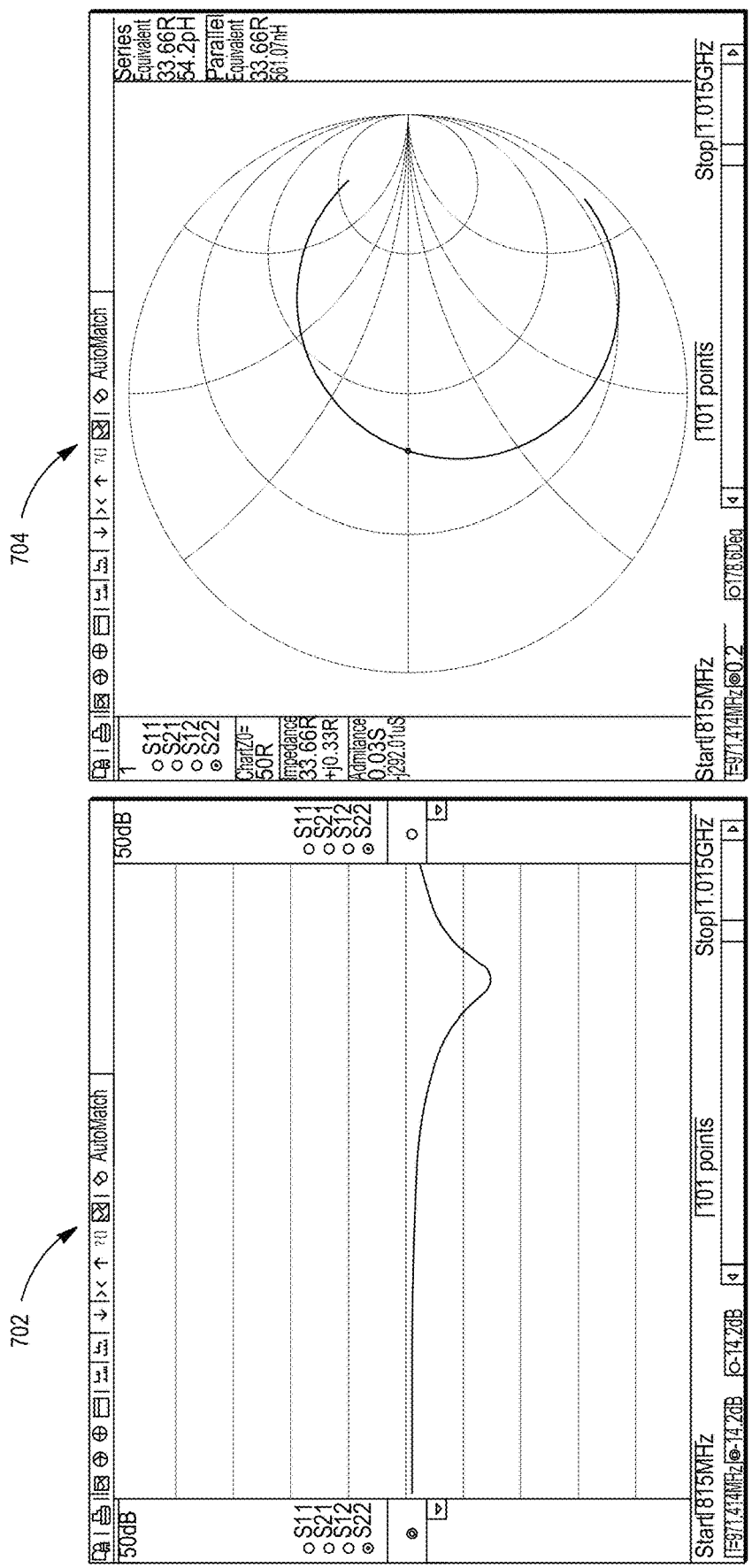
FIG. 7 shows in both Cartesian chart 702 (on the left) and Smith chart 704 (on the right) of spiral non-coupled monopole (already miniaturized radiators) antenna arms, in accordance with some embodiments.

FIG. 7 shows in both Cartesian chart 702 (on the left) and Smith chart 704 (on the right) of spiral non-coupled monopole (already miniaturized radiators) antenna arms, in accordance with some embodiments. FIG. 7 demonstrates the case where two independent (non-coupling) monopoles share the same ground plane, i.e. no coupling locus seen in the Smith chart. In some embodiments, S22 in the FIG. 7 indicates the antenna input impedance, which comes from the data file generated by a network analyzer port 2.

Figure 8:
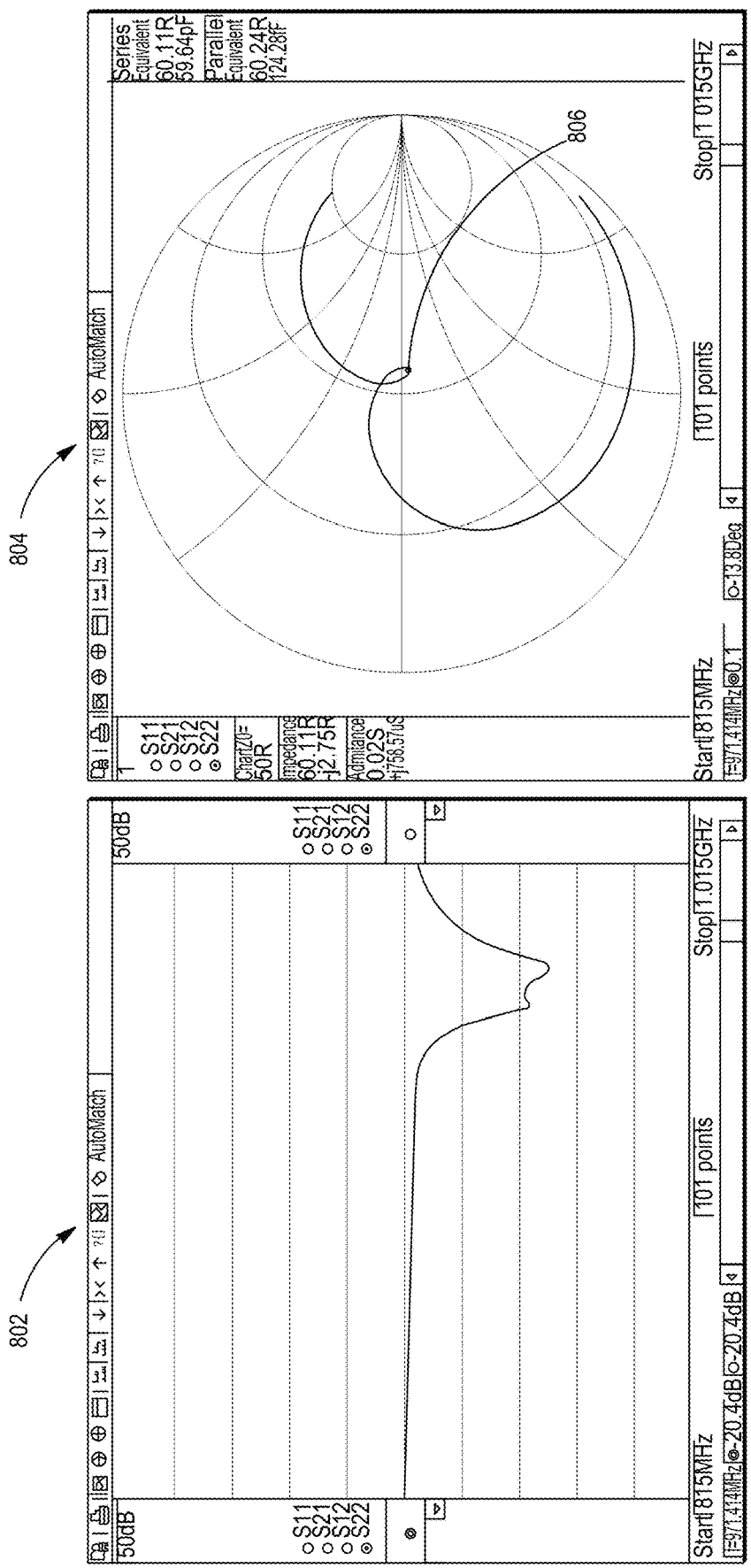
FIG. 8 shows in both Cartesian chart 802 (on the left) and Smith chart 804 (on the right) of spiral coupled monopole antenna arms, in accordance with some embodiments.

FIG. 8 shows in both Cartesian chart 802 (on the left) and Smith chart 804 (on the right) of spiral coupled monopole antenna arms, in accordance with some embodiments. The antenna arms are miniaturized radiators, and the mutual coupling between the monopoles are established but not optimized for bandwidth. Coupling locus 806 can be seen in the Smith chart as a small loop around 50 Ohm center, which on the other hand means nearly perfect antenna match to the feed.

Figure 9:
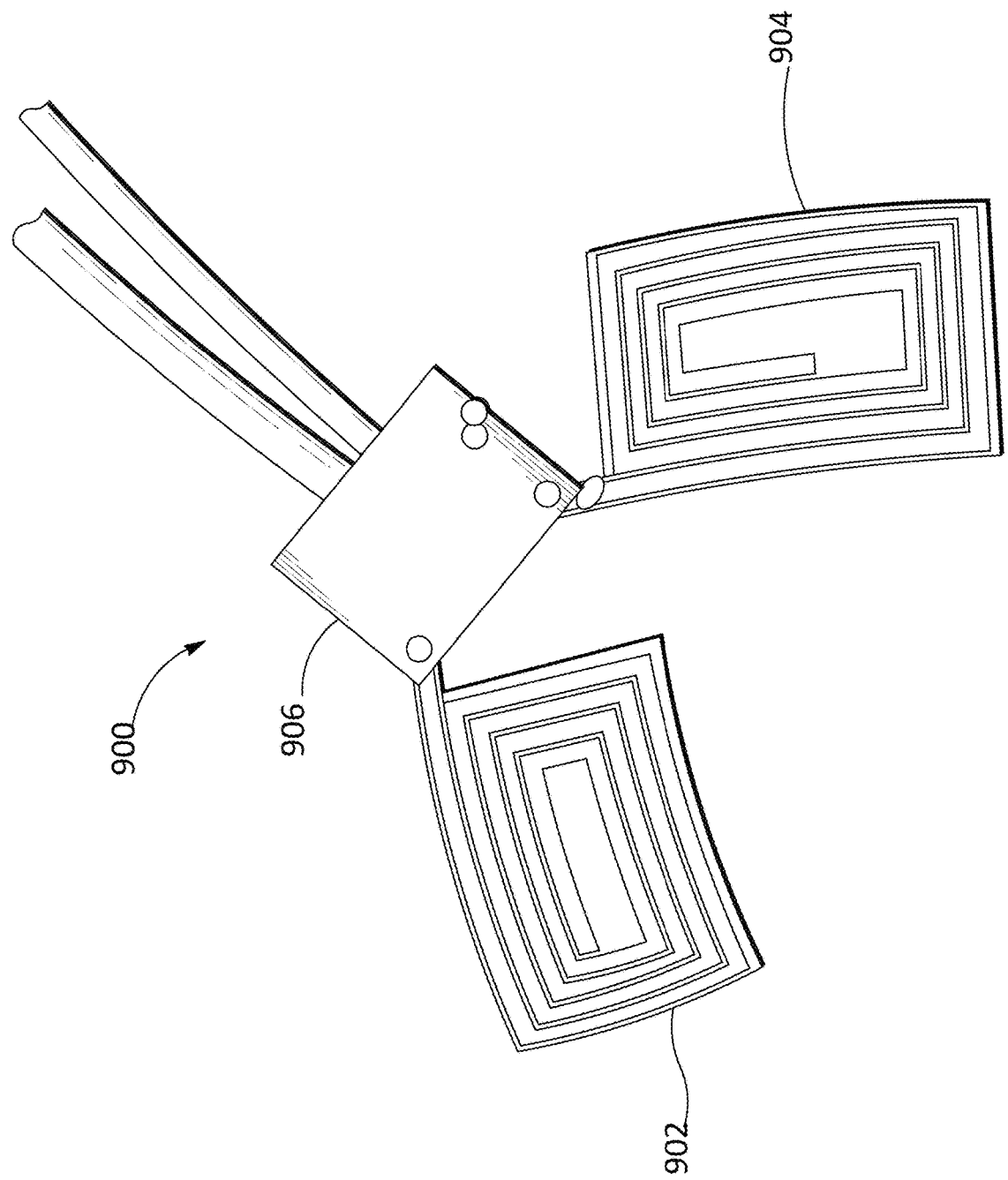
FIG. 9 shows a wireless power receiving system 900 having a non-coupling configuration of two monopoles 902 and 904 sharing the same ground plane 906, in accordance with some embodiments.

FIG. 9 shows a wireless power receiving system 900 having non-coupling configuration of two monopoles 902 and 904 sharing the same ground plane 906, in accordance with some embodiments. The performance of the wireless power receiving system 900 can be similar to the charts described in FIG. 7.

Figure 10:
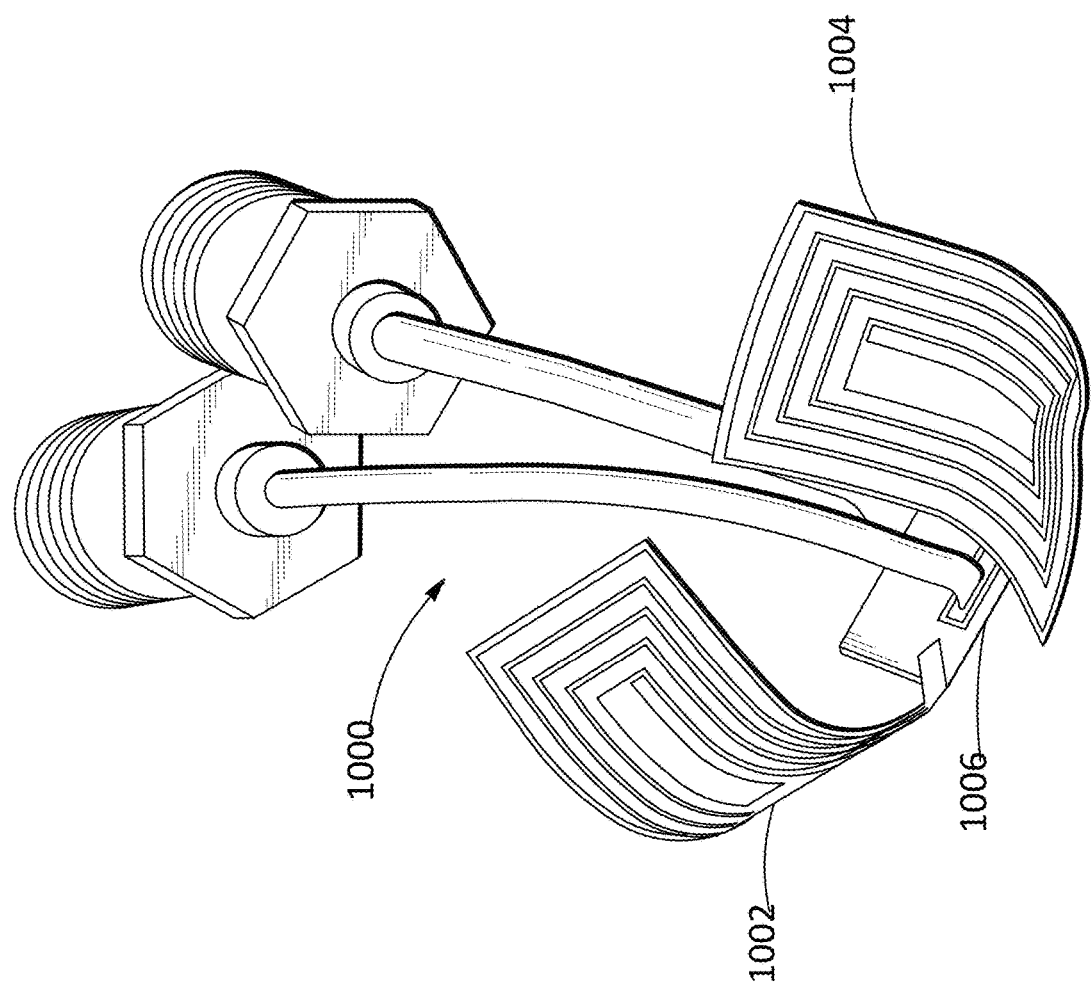
FIG. 10 shows a wireless power receiving system 1000 having a strong mutual coupling configuration of two monopoles 1002 and 1004 sharing the same ground plane 1006.

FIG. 10 shows a wireless power receiving system 1000 having strong mutual coupling configuration of two monopoles 1002 and 1004 sharing the same ground plane 1006. The coupling happens between the two monopoles 1002 and 1004, when the two antenna arms (monopoles) are in close proximity to each other. The coupling of the two monopoles 1002 and 1004 is increased when the open ends of the monopoles 1002 and 1004 are pulled close to each other. When the distance between the open ends of the monopoles 1002 and 1004 is equal or less than the largest dimension of either of the monopole spiral radiators, strong coupling occurs. In some embodiments, the strong coupling is at least −3 dB and less than 0 dB. The performance of the wireless power receiving system 1000 can be similar to the charts described in FIG. 8.

When the receiver antenna elements of a wireless power receiving system have coupling of −3 dB or higher and less than 0 dB, the benefits of this invention become visible. In some embodiments, when half or more of the power is coupled, the coupling between the receiver antenna elements is strong in the range about −3 dB or higher and less than 0 dB.

Transmission wavelength for 1 GHz frequency is about 30 cm. In some embodiments, devices can be as small as 1 cm, and the maximum dimensions of the antenna elements or arms are of the same order. For instance, having to tune from typical (to an electrically small antenna) low resistance and inductive reactance of e.g. 30 Ohm-j100 Ohm (R-jX) to a resonance, 17 nH need to be added in series using some lossy matching components such as inductors which add 2.9 dB losses. Using 13 nH would add 1.9 dB losses, and even 6.1 nH would add 0.5 dB losses, all at 915 MHz frequency. Just for reference, with the above cases, the power received by the wireless power receive system would be 90 mW at 17 nH addition, 60 mW at 13 nH addition, and 50 mW at 6.1 nH addition compared to perfectly matched case of 100 mW reception (with lossless matching or self-resonant antennas).

Further embodiments also include various subsets of the above embodiments including embodiments in FIGS. 1-10 combined or otherwise re-arranged in various embodiments.

Figure 11:
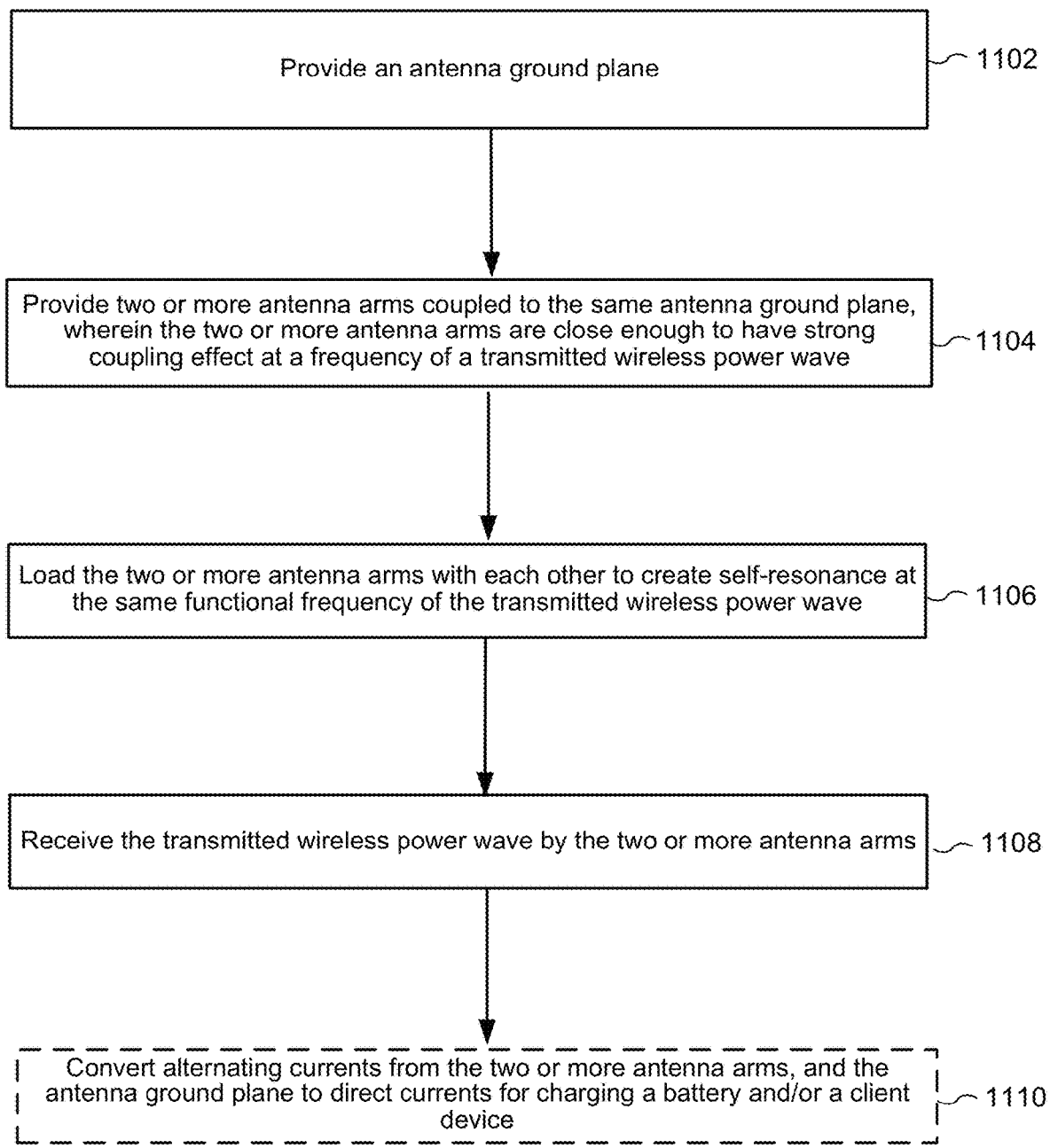
FIG. 11 is a flow diagram showing a method of receiving wireless power transmissions with heavily coupled electrically small antennas, in accordance with some embodiments.

FIG. 11 is a flow diagram showing a method of receiving wireless power transmissions with heavily coupled electrically small antennas, in accordance with some embodiments. Operations (e.g., steps) of the method 1100 may be performed by a wireless power receiver system (e.g. receiver 120 or electronic device 122a, FIG. 1; wireless power receiving system 200, FIG. 2; wireless power receiving system 400, FIG. 4; wireless power receiving system 500, FIG. 5; wireless power receiving system 600, FIG. 6; wireless power receiving system 1000, FIG. 10) and/or by one or more components thereof (e.g. antenna ground plane 406, FIG. 4). At least some of the operations shown in FIG. 11 correspond to instructions stored in a computer memory or computer-readable storage medium (e.g., memory 142 of the receiver 120, FIG. 1).

The method 1100 includes a step 1102 of providing an antenna ground plane (e.g., antenna ground plane 406, FIG. 4; antenna ground plane 506, FIG. 5; antenna ground plane 606, FIG. 6).

The method 1100 also includes a step 1104 of providing two or more antenna arms (e.g., antenna arms 402 and 404, FIG. 4; antenna arms 502 and 504, FIG. 5; antenna arms 602 and 604, FIG. 6; antenna arms 1002 and 1004, FIG. 10) coupled to the same antenna ground plane 406. In some embodiments, the first and the second antenna arms 402 and 404 are substantially perpendicular to one another such as shown in FIG. 5.

In some embodiments, the two or more antenna arms are close enough in space to have strong coupling effect at a frequency of a transmitted wireless power wave. In some embodiments, for two antennas, the coupling is at least −3 dB to 0 dB. In some embodiments, for three antennas, the coupling is at least −4.8 dB to 0 dB. In some embodiments, for four antennas, the coupling is at least −6 dB to 0 dB.

The method 1100 further includes a step 1106 of loading the two or more antenna arms with each other to create self-resonance at the same functional frequency of the transmitted wireless power wave.

The method 1100 further includes a step 1108 of receiving the transmitted wireless power wave by the first 402, and the second 404 antenna arms.

The method 1100 further includes a step 1110 of converting alternating currents from the two or more antenna arms, and the antenna ground plane to direct currents for charging a battery and/or a client device. In some embodiments, the AC to DC conversion is done by a rectifier (also described as 126 in FIG. 1, 204 in FIG. 2) and/or other power converters 126 that include a PMIC (shown as 206 in FIG. 2).

Further embodiments also include various subsets of the above embodiments including embodiments in FIGS. 1-11 combined or otherwise re-arranged in various embodiments.

Figure 12:
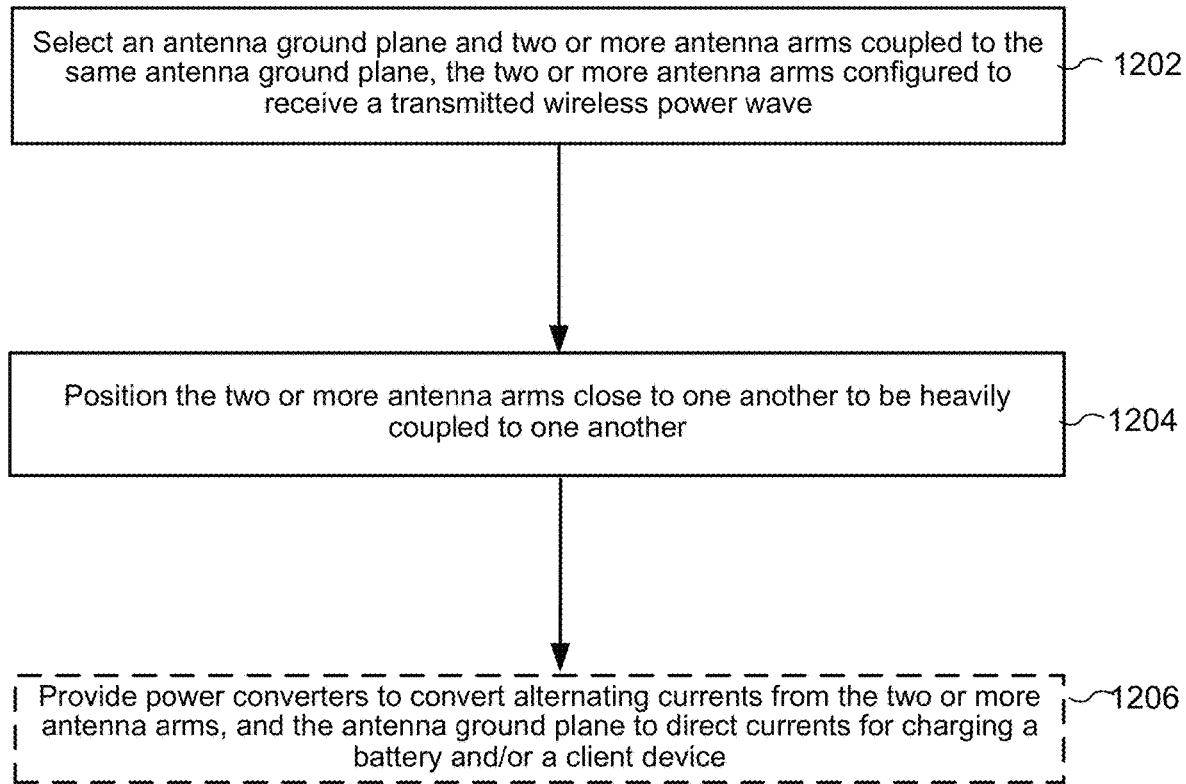
FIG. 12 is a flow diagram showing a method of fabricating a wireless power receiving system with heavily coupled electrically small antennas, in accordance with some embodiments.

FIG. 12 is a flow diagram showing a method of fabricating a wireless power receiving system with heavily coupled electrically small antennas, in accordance with some embodiments. The wireless power receiving system includes a wireless power receiver or a receiver system (e.g. receiver 120 or electronic device 122, FIG. 1; wireless power receiving system 200, FIG. 2; wireless power receiving system 400, FIG. 4; wireless power receiving system 500, FIG. 5; wireless power receiving system 600, FIG. 6; wireless power receiving system 1000, FIG. 10) and/or by one or more components thereof (e.g. antenna ground plane 406, FIG. 4).

The method 1200 includes selecting (1202) an antenna ground plane (e.g., antenna ground plane 406, FIG. 4; antenna ground plane 506, FIG. 5; antenna ground plane 606, FIG. 6) and two or more antenna arms (e.g., antenna arms 402 and 404, FIG. 4; antenna arms 502 and 504, FIG. 5; antenna arms 602 and 604, FIG. 6; antenna arms 1002 and 1004, FIG. 10) coupled to the antenna ground plane 406. In some embodiments, the two or more antenna arms are configured to receive a transmitted wireless power waves.

The method 1200 further includes positioning (1204) the two or more antenna arms 402 and 404 close to one another to be heavily coupled to one another. In some embodiments, for two antennas, the coupling is at least −3 dB to 0 dB. In some embodiments, for three antennas, the coupling is at least −4.8 dB to 0 dB. In some embodiments, for four antennas, the coupling is at least −6 dB to 0 dB.

The method 1200 further includes providing (1206) power converters to convert alternating currents from the two or more antenna arms, e.g. antenna arms 402 and 404, and the antenna ground plane to direct currents for charging a battery and/or a client device. In some embodiments, the AC to DC conversion is done by a rectifier (also described as 126 in FIG. 1, 204 in FIG. 2) and/or other power converters 126 that include a PMIC (shown as 206 in FIG. 2).

Further embodiments also include various subsets of the above embodiments including embodiments in FIGS. 1-12 combined or otherwise re-arranged in various embodiments.

The preceding description of the disclosed embodiments is provided to enable any person skilled in the art to make or use the embodiments described herein and variations thereof. Various modifications to these embodiments will be readily apparent to those skilled in the art, and the generic principles defined herein may be applied to other embodiments without departing from the spirit or scope of the subject matter disclosed herein. Thus, the present disclosure is not intended to be limited to the embodiments shown herein but is to be accorded the widest scope consistent with the following claims and the principles and novel features disclosed herein.

Features of the present invention can be implemented in, using, or with the assistance of a computer program product, such as a storage medium (media) or computer readable storage medium (media) having instructions stored thereon/in which can be used to program a processing system to perform any of the features presented herein. The storage medium (e.g., memory 106, 134, and/or 142) can include, but is not limited to, high-speed random access memory, such as DRAM, SRAM, DDR RAM or other random access solid state memory devices, and may include non-volatile memory, such as one or more magnetic disk storage devices, optical disk storage devices, flash memory devices, or other non-volatile solid state storage devices. Memory (e.g., 106, 134, and/or 142) optionally includes one or more storage devices remotely located from the CPU(s) (e.g., processor(s) 104, 132, and/or 140). Memory (e.g., 106, 134, and/or 142), or alternatively the non-volatile memory device(s) within the memory, comprises a non-transitory computer readable storage medium.

Stored on any one of the machine readable medium (media), features of the present invention can be incorporated in software and/or firmware for controlling the hardware of a processing system (such as the components associated with the transmitters 102 and/or receivers 120), and for enabling a processing system to interact with other mechanisms utilizing the results of the present invention. Such software or firmware may include, but is not limited to, application code, device drivers, operating systems, and execution environments/containers.

Communication systems as referred to herein (e.g., communications components 112, 136, and/or 144) optionally communicate via wired and/or wireless communication connections. Communication systems optionally communicate with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. Wireless communication connections optionally use any of a plurality of communications standards, protocols and technologies, including but not limited to radio-frequency (RF), radio-frequency identification (RFID), infrared, radar, sound, Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), ZigBee, wideband code division multiple access (W-CDMA), code division multiple access (CDMA), time division multiple access (TDMA), Bluetooth, Wireless Fidelity (Wi-Fi) (e.g., IEEE 102.11a, IEEE 102.11ac, IEEE 102.11ax, IEEE 102.11b, IEEE 102.11 g and/or IEEE 102.11n), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of this document.

It will be understood that, although the terms "first," "second," etc. may be used herein to describe various elements, these elements should not be limited by these terms. These terms are only used to distinguish one element from another.

The terminology used herein is for the purpose of describing particular embodiments only and is not intended to be limiting of the claims. As used in the description of the embodiments and the appended claims, the singular forms "a," "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "in response to determining" or "in accordance with a determination" or "upon detecting" or "in response to detecting" that the stated condition precedent is true, depending on the context.

The foregoing description, for purpose of explanation, has been described with reference to specific embodiments. However, the illustrative discussions above are not intended to be exhaustive or to limit the claims to the precise forms disclosed. Many modifications and variations are possible in view of the above teachings. The embodiments were chosen and described in order to best explain principles of operation and practical applications, to thereby enable others skilled in the art.

What is claimed is:

1. A method for receiving wireless power waves, comprising:
    providing a wireless power receiving system comprising an antenna ground plane and two or more antenna arms, wherein a largest dimension of the wireless power receiving system is at or smaller than 30 millimeters, and a first of the two or more antenna arms is on a first flexible substrate and a second of the two or more antenna arms is on a second flexible substrate distinct and separate from the first flexible substrate;

providing the antenna ground plane;

separately coupling each of the two or more antenna arms to the antenna ground plane via the first and second flexible substrates, wherein the two or more antenna arms are strong coupled to one another at a frequency of a transmitted wireless power wave;

loading the two or more antenna arms with each other to create self-resonance at the frequency of the transmitted wireless power wave, wherein the self-resonance is created without coupling matching components to the two or more antenna arms; and receiving the transmitted wireless power wave by the two or more antenna arms.

2. The method of claim 1, wherein the two or more antenna arms are strongly coupled to one another to at least −3 dB and less than 0 dB.

3. The method of claim 1, wherein the self-resonance is created to ensure that the two or more antenna arms are matched to a predetermined reference impedance value.

4. The method of claim 3, wherein the predetermined reference impedance value 50 Ohm.

5. The method of claim 1, wherein a longest dimension of each of the two or more antenna arms is no greater than one-sixth of a wavelength of the transmitted wireless power wave.

6. The method of claim 1, wherein each of the two or more antenna arms is a monopole antenna.

7. The method of claim 1, wherein each of the two or more antenna arms is a planar inverted-F antenna (PIFA).

8. The method of claim 2, further comprising converting an alternating current of the transmitted wireless power wave to a direct current for providing power to a hearing aid, using a power converter that is coupled to one or both of the two or more antenna arms.

9. The method of claim 8, further comprising storing power from the transmitted wireless power wave in a battery of the hearing aid.

10. A hearing aid, comprising:
a receiver for receiving near-field wireless power transmissions, wherein a largest dimension of the receiver is at or smaller than 30 millimeters, the receiver including:
an antenna ground plane; and
first and second antenna arms separately coupled to the antenna ground plane, and configured to receive a transmitted wireless power wave, wherein:
the first antenna arm is on a first flexible substrate and the second antenna arm on a second flexible substrate distinct and separate from the first flexible substrate;
the first and the second antenna arms are mutually coupled to one another to at least −3 dB and less than 0 dB and are loaded with each other to create self-resonance at the frequency of the transmitted wireless power wave, wherein the self-resonance is created without coupling matching components to the two or more antenna arms; and power conversion circuitry configured to convert an alternating current from the transmitted wireless power wave into a direct current; and a battery of the hearing aid, wherein the battery is configured to receive and store the direct current to provide power to the hearing aid.

11. The wireless power receiving system of claim 10, wherein a longest dimension of the wireless power receiving system is no greater than 10 mm.

12. A method of fabricating a wireless power receiving system for receiving wireless power waves, comprising:

separately coupling two or more antenna arms to an antenna ground plane, wherein a largest dimension of the two or more antenna arms and the antenna ground plane is at or smaller than 30 millimeters, a first of the two or more antenna arms is on a first flexible substrate, a second of the two or more antenna arms is on a second flexible substrate distinct and separate from the first flexible substrate, the two or more antenna arms are configured to receive a transmitted wireless power wave having a frequency and a wavelength, and each of the two or more antenna arms has a largest dimension no greater than one-sixth of the wavelength; and positioning the two or more antenna arms close to one another to create a strong coupling at the frequency of the transmitted wireless power wave between the two or more antenna arms, wherein the two or more antenna arms are also loaded with each other to create self-resonance at the frequency of the transmitted wireless power wave, and further wherein the self-resonance is created without coupling matching components to the two or more antenna arms.

13. The method of claim 12, further comprising:

coupling power conversion circuitry to the two or more antenna arms, the power conversion circuitry configured to convert an alternating current from the transmitted wireless power wave to a direct current; and coupling the power conversion circuit to a battery of a hearing aid, the battery of the hearing aid configured to receive and store the direct current for use in providing power to the hearing aid.

* * * * *